US011160886B2

(12) United States Patent
Bolzati et al.

(10) Patent No.: US 11,160,886 B2
(45) Date of Patent: Nov. 2, 2021

(54) METHOD FOR LABELING OF SENSITIVE AND THERMOSENSITIVE TARGETING BIOMOLECULES WITH TECHNETIUM BASED COMPOUNDS

(71) Applicant: BRACCO IMAGING SPA, Milan (IT)

(72) Inventors: Cristina Bolzati, Terre del Reno (IT); Nicola Salvarese, Vicenza (IT); Fiorenzo Refosco, Valdagno (IT); Simona Ghiani, Almese (IT); Alessandro Maiocchi, Monza (IT); Barbara Spolaore, Mirano (IT)

(73) Assignee: BRACCO IMAGING SPA, Milan (IT)

( * ) Notice: Subject to any disclaimer, the term of this patent is extended or adjusted under 35 U.S.C. 154(b) by 0 days.

(21) Appl. No.: 16/469,541

(22) PCT Filed: Dec. 15, 2017

(86) PCT No.: PCT/EP2017/083024
§ 371 (c)(1),
(2) Date: Jun. 13, 2019

(87) PCT Pub. No.: WO2018/109164
PCT Pub. Date: Jun. 21, 2018

(65) Prior Publication Data
US 2020/0078479 A1 Mar. 12, 2020

(30) Foreign Application Priority Data
Dec. 15, 2016 (EP) ..................................... 16204413

(51) Int. Cl.
*A61K 51/04* (2006.01)
*A61K 51/08* (2006.01)

(52) U.S. Cl.
CPC ...... *A61K 51/0497* (2013.01); *A61K 51/0478* (2013.01); *A61K 51/082* (2013.01); *A61K 51/088* (2013.01)

(58) Field of Classification Search
None
See application file for complete search history.

(56) References Cited

U.S. PATENT DOCUMENTS

| 6,270,745 B1 | 8/2001 | Duatti et al. |
| 7,445,765 B2 | 11/2008 | Duatti et al. |
| 8,182,789 B2 | 5/2012 | Tisato et al. |

FOREIGN PATENT DOCUMENTS

| IT | 1397547 B1 | 1/2013 |
| JP | 2008037752 A | 2/2008 |

OTHER PUBLICATIONS

Bolzati et al. The [(99m)Tc(N)(PNP)](2+) metal fragment: a technetium-nitrido synthon for use with biologically active molecules. The N-(2-methoxyphenyl)piperazyl-cysteine analogues as examples. 2003 Bioconjug. Chem. 14: 1231-1242. (Year: 2003).*
Agostini, S., "Universita Degli Studi Di Padova, Scuola Di Dottorato Di Ricerca in Scienze Molecolari Indirizzo Scienze Farmaceutiche Ciclo XX, Il Sistema [MV(N)(PNP)] 2+ (M=Tc-99m, Re-188) Nella Scintigrafia Miocardica E in Medicina Nucleare Molecolare", pp. 1-262 (2008) (English Abstract).
Baxley, G. et al., "Synthesis and catalytic chemistry of two new water-soluble chelating phosphines: comparison of ionic and nonionic functionalities," Journal of Molecular Catalysis A:Chemical, 116:191-198 (1997).
Benešová, M. et al., "Linker Modification Strategies to Control the Prostate-Specific Membrane Antigen (PSMA)-Targeting and Pharmacokinetic Properties of DOTA-Conjugated PSMA Inhibitors," J. Med. Chem. 59:1761-1775 (2016).
Bolzati, C. et al., "SPECT Imaging of αvβ3 Expression by [99mTc(N)PNP43]—Bifunctional Chimeric RGD Peptide not Cross-Reacting with αvβ5," In: 18th European Symposium on Radiopharmacy and Radiopharmaceuticals, Abstract OP07 (2016).
Bolzati, C., et al., "Avidin-biotin system: a small library of cysteine biotinylated derivatives designed for the [99mTc(N)(PNP)]2+ metal fragment", Nuclear Medicine and Biology, 34:511-522 (2006).
Bolzati, C., et al., "Biological in Vitro and in Vivo Studies of a Series of New Asymmetrical Cationic [99mTc(N)(DTC-Ln)(PNP)]+ Complex (DTC-LN = Alicyclic Dithiocarbamate and PNP=Diphosphlnoamine)", Bioconjugate Chem., 21:(5):928-939 (2010).
Bolzati, C., et al., "Synthesis, Characterization, and Biological Evaluation of Neutral Nitrido Technetium(V) Mixed Ligand Complexes Containing Dithiolates and Aminodiphosphines. A Novel System for Linking Technetium to Biomolecules", Bioconjugate Chem., 15(3):628-637 (2004).
Boschi, A., et al., A Novel Approach to the High-Specific-Activity Labeling of Small Peptides with the Technetium-99m Fragment [99mTc(N)(PXP)]2+ (PXP = Diphosphine Ligand), Bioconjugate Chem., 12(6):1035-1042 (2001).
Boschi, A., et al., "Asymmetrical Nitrido Tc-99m Heterocomplexes as Potential Imaging Agents for Benzodiazepine Receptors", Bioconjugate Chem., 14(6):1279-1288 (2003).
Carta, D., et al., ""Assessment of the best N3—donors in preparation of [M(N)(PNP)]-based (M=99mTc-; 188Re) target-specific radiopharmaceuticals: Comparison among succinic dihydrazide (SDH), N-methyl-S-methyl dithiocarbazate (HDTCZ) and PEGylated N-methyl-S-methyl dithiocarbazate (HO2C-PEG600-DTCZ)"", Nuclear Medicine and Biology, 41(7):570-581 (2014).
Decristoforo, C. et al., "Comparison of in vitro and in vivo properties of [99mTc]cRGD peptides labeled using different novel Tc-cores", The Quarterly Journal of Nuclear Medicine and Molecular Imaging, 51(1):33-41 (2007).
European Search Report for European App. No. 16204413.5, dated Oct. 12, 2017.

(Continued)

*Primary Examiner* — Jennifer Lamberski
(74) *Attorney, Agent, or Firm* — VIVICAR Law, PLLC

(57) ABSTRACT

The present invention relates to a labeling procedure for the incorporation, in mild reaction conditions, of sensitive and thermosensitive targeting molecules into a [99m Tc(N)(PNP)]-based compound suitable for a kit formulation.

20 Claims, 15 Drawing Sheets

Specification includes a Sequence Listing.

(56) References Cited

OTHER PUBLICATIONS

International Search Report and Written Opinion for PCT/EP2017/083024, dated Jan. 24, 2018.

Weineisen, M., et al., "Synthesis and preclinical evaluation of DOTAGA-conjugated PSMA ligands for functional Imaging and endoradiotherapy of prostate cancer", EJNMMI Research, 4:63 (2014).

Zaccaro, L. et al., "[99mTc(N)PNP43]-labelled RGDechi peptide: a new radiotracer for the selective SPECT imaging of alpha-v-beta-3 integrin expression," In: XVI Workshop on PharmaBioMetallics, Abstract OC 23 (2016).

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Cys Gly Lys Gly
1
```

METHOD FOR LABELING OF SENSITIVE AND THERMOSENSITIVE TARGETING BIOMOLECULES WITH TECHNETIUM BASED COMPOUNDS

CROSS-REFERENCE TO RELATED APPLICATIONS

This application is the national stage application of corresponding international application number PCT/EP2017/083024, filed Dec. 15, 2017, which claims priority to and the benefit of European application no. 162044115, filed Dec. 15, 2016, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 24, 2020, is named 01122_0063-00000_SL.txt and is 582 bytes in size.

FIELD OF THE INVENTION

The present invention relates to a process for labeling sensitive and thermosensitive active biomolecules with Technetium, in mild conditions, and any obtained compound as active ingredient for radio-diagnostic molecular imaging.

BACKGROUND

Nowadays $^{99m}$Tc represents for its optimal nuclear properties and low cost easy availability, the radioisotope of election in NM being used in different chemical forms in more than 80% of the clinical practices SPECT; it is indispensable for an estimated 70,000 medical imaging procedures that take place daily around the world. The 6 h half-life time ($t_{1/2}$) of $^{99m}$Tc, is sufficiently long allowing completing any radiopharmaceutical synthesis in radiopharmacies, distribution to hospitals, dose preparation, administration and collection of clinically useful images. At the same time, the half-life time is short enough to minimize radiation dose delivered to the patient. The monochromatic 140 keV photons (90% abundance), close to optimal for imaging with commercial gamma cameras, are readily collimated to give images with high spatial resolution. The absence of corpuscular radiation allows the injection of activities of more than 30 mCi (1.1 GBq) with low radiation exposure to the patient. These nuclear properties are combined with easy availability of the $^{99}$Mo/$^{99m}$Tc generator, moderate cost of the isotope and reasonably simple reconstitution of the radiopharmaceutical starting from eluted sodium pertechnetate, Na[$^{99m}$TcO$_4$], with a series of kits provided by several pharmaceutical companies. In addition, the possibility to systematically study the chemistry of this transition metal utilizing the long-lived $^{99g}$Tc isotope ($E_{\beta-}$=292 keV, $t_{1/2}$=2.12×10$^5$ yr) offers the advantage to elucidate the molecular structure of the injected radioactive agent, and eventually, through rational modifications of the molecule, finely tune the biological properties of these compounds.

In past years, the chemistry of potential $^{99m}$Tc radiopharmaceuticals has been expanded due to the introduction of an efficient method for the production, at tracer level, of $^{99m}$Tc species containing the terminal Tc≡N multiple bond, in sterile and pyrogen-free conditions. It was found that the resulting [Tc≡N]$^2$ core could be viewed as a true inorganic functional group exhibiting very high stability under a wide range of experimental conditions. Based on these considerations, extensive studies have been carried out on the synthesis and biological evaluation of different classes of symmetrical and dissymmetrical five-coordinate nitrido technetium complexes of the type [$^{99m}$Tc(N)(L)], where L is a dithiocarbamate, and [$^{99m}$Tc(N)(PNP)(YZ)]$^{0/+}$, where PNP is a polydentate bisphosphinoamine and YZ a π-donor bidentate ligand.

Nitrido dissymmetrical compounds of the type [$^{99m}$Tc(N)(PNP)(YZ)]$^{0/+}$, useful in nuclear medicine applications, are disclosed in several documents, e.g U.S. Pat. Nos. 6,270,745; 7,445,765; JP2008037752; U.S. Pat. No. 8,182,789; PD2009A000110; C. Bolzati, M. Cavazza-Ceccato, S. Agostini, F. Refosco, Y. Yamamichi, S. Tokunaga, D. Carta, N. Salavarese, D. Bernardini, G. Bandoli, Bioconjugate Chem. (2010), 21, 928-939.

In particular, as disclosed for instance in A. Boschi, C. Bolzati, E. Benini, E. Malago, L. Uccelli, A. Duatti, A. Piffanelli, F. Refosco, F. Tisato, Bioconj. Chem. (2001), 12, 1035-1042; C. Bolzati, E. Benini, E. Cazzola, C. M. Jung, F. Tisato, F. Refosco, H. J. Pietzsch, H. Spies, L. Uccelli, A. Duatti, Bioconj. Chem. (2004), 15, 628-637; A. Boschi, L. Uccelli, A. Duatti, C. Bolzati, F. Refosco, F. Tisato, R. Romagnoli, P. G. Baraldi, K. Varani, P. Borea, Bioconj. Chem. (2003), 14, 1279-1288, the [Tc(N)(PNP)]-scaffold is attractive as a platform for radiolabeling bioactive molecules and molecular vectors, for SPECT imaging, providing high stability and high specific activity of the final product.

The focus in the development of Tc-based target specific radiopharmaceuticals lies in the need of having an efficient labeling procedure leaving the biological properties of the native molecule unaltered. Another important requirement is to obtain a radiolabeled compound in high specific activity, possibly in mild reaction conditions. Hence, the radiosynthesis must be performed in aqueous solution under sterile, pyrogen-free conditions and should be completed within 30 min. The yield of the radiotracer must be ≥90% with high solution stability because the injection of a mixture of $^{99m}$Tc-species would decrease the organ specificity. No purification of the final product should be necessary. In addition, for the receptor-based radiotracers, the use of a large amount of the "cold" BFC-BAM conjugate (BFC=bifunctional chelator, BAM=bioactive molecule) may result in receptor site saturation and the blockage of receptor docking for the radiotracer. To avoid this problem, the BFC-BAM conjugate concentration in each kit formulation has to be very low (10$^{-6}$-10$^{-5}$ M). Otherwise, a post-labeling purification is needed to remove the excess of unlabeled receptor ligand, which is very time consuming and not amenable for clinical use.

However, Technetium requires chelation chemistry for radiolabeling a BAM and some complexation reactions can be quite slow, requiring high temperatures and/or drastic pH values over extended times and therefore compromising the use of such radiolabeling methodologies. As described in all the previously cited references, [Tc(N)(PNP)]-labeled targeting molecules can be efficiently prepared by simultaneously adding the appropriate bisphosphinoamine and the selected modified vector to a mixture of Tc(N)-intermediates; ligands coordination is achieved by heating the reaction mixture at 80-100° C. for 30 min.

Therefore, this technique is not suitable for the labeling of (thermo)sensitive biomolecules such as proteins, monoclonal antibodies or fragments of their, demanding mild reaction conditions, e.g. with respect to pH-value and reaction temperature.

The applicant has now found an efficient labeling procedure for the incorporation, in mild reaction conditions, suitable for a kit formulation, of (thermo)sensitive targeting molecules into a [$^{99m}$Tc(N)(PNP)]-based compound.

Definitions

In the present description, and unless otherwise provided, the term "bioactive molecule", refers to a compound which has the capability and the ability to interact at molecular level with species that are express or overexpress, in a specific tissue, in a disease state. Just as an example, the term "bioactive molecule" comprises within its meanings polypeptides, proteins, aptamers, antibodies or fragments of their.

Abu stands for gamma-aminobutiric acid.
CysNAc stands for N-Acetyl-L-cysteine.
cRGDfK stands for cyclo (Arg-Ala-Asp-D-Phe-Lys) pentapeptide.
HDTCZ stands for S-methyl dithiocarbazate.
ApoMb stands for apomioglobin.
Biot stands for biotin.
Cys stands for cysteine.
Gly stands for glycine.
Lys stands for lysine.
Glu stands for glutamic acid.
Ala stands for alanine.
Amc stands for 4-(aminomethyl)cyclohenane.
Fab stands for fragment antigen-binding.
PNP, as used herein, refers to a generally defined bisphosphinoamine.
PNP3OH is a bisphosphinoamine substituted at P atoms by —CH$_2$OH groups.
PNP43 is a bisphosphinoamine substituted at P atoms by —CH$_3$ groups.
PNP3 is a bisphosphinoamine substituted at P atoms by —(CH$_2$)$_3$OCH$_3$ groups.
PNP44 is a bisphosphinoamine substituted at P atoms by —CH$_2$CH$_3$ groups.
H$_2$PN(OMe)PH$_2$ is a bisphosphinoamine substituted at P atoms by —H atoms.
PNP3COOH is a bisphosphinoamine substituted at P atoms by —CH$_2$CH$_2$COOH groups.
PB stands for sodium phosphate buffer.
PBS stands for phosphate buffered saline.
RCY stands for radiochemical yield.
RCP stands for radiochemical purity.
In the present description, RCY and RCP exhibit comparable values as no meaningful radioactivity losses occur during HPLC.
Mild Conditions, Mild Temperature and Mild pH
Mild conditions vary from embodiments to embodiments. For some embodiments, the mild condition refers to mild temperature, while for some embodiments, the mild condition refers to mild pH. Yet for some other embodiments, the mild condition refers to mild temperature and mild pH.
Mild temperature also varies from embodiments to embodiments. For some embodiments, the mild temperature stands for a temperature range of from 15° C. to 60° C. For some other embodiments, the mild temperature stands for temperature ranges of from 15° C. to 50° C., from 20° C. to 45° C., from 20° C. to 40° C., from 20° C. to 35° C., from 20° C. to 30° C., and preferably from 20° C. to 25° C.
Room temperature stands for a temperature range of from 20° C. to 25° C.
Mild pH also varies from embodiments to embodiments. For some embodiments, mild pH stands for a pH range of from 5.5 to 9.0, while for some other embodiments, mild pH stands for pH ranges of from 6.0 to 8.5, from 6.5 to 8.0, and preferably from 7 to 7.5.

About neutral pH stands for a pH range of from 7 to 7.5.

SUMMARY OF THE INVENTION

Figure 1:
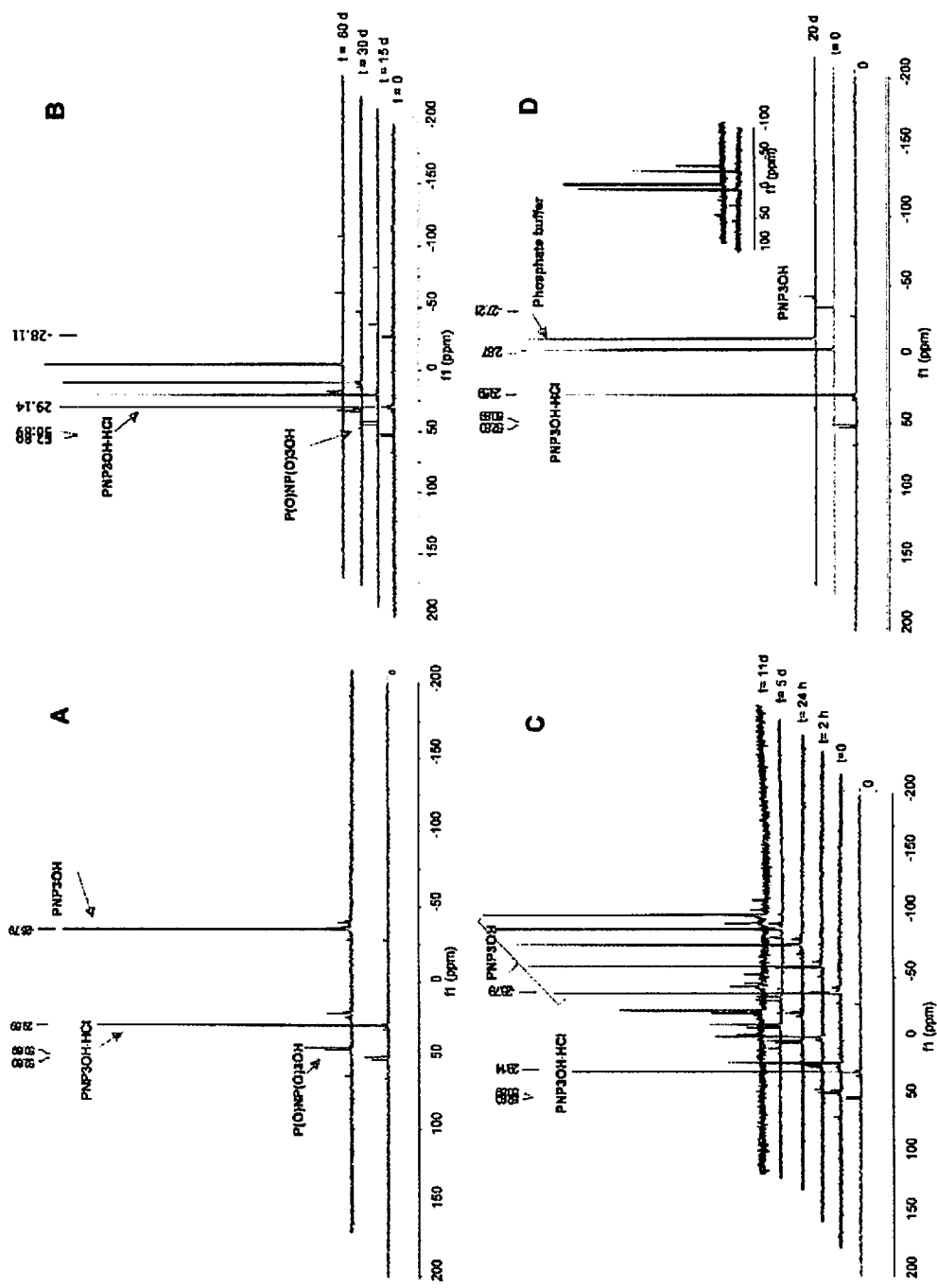
FIG. 1 represents a $^{31}$P NMR spectra of PNP3OH.HCl and of PNP3OH (A) and the oxidative stability of PNP3OH.HCl and PNP3OH over the time in H$_2$O (B), carbonate buffer 0.5 M pH 9 (C), phosphate buffer 0.2 M, pH 7.4 (D).

An aspect of the invention relates to novel Technetium heterocomplexes, of the type [$^{99m}$Tc(N)(PNP)(YZ)]$^{0/+}$, useful in radiopharmaceutical applications, of general formula I:

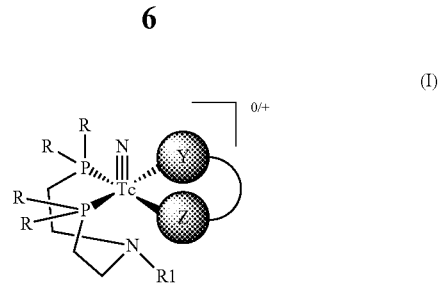

(I)

wherein:

Tc is $^{99m}$Tc;

R is hydrogen (—H) or a group of formula —(CH$_2$)$_n$-A, wherein n is an integer of 1 or 2 and A is selected from the group consisting of hydrogen (—H), hydroxyl (—OH), methyl (—CH$_3$), carboxyl (—COOH), sodium carboxyl (—COONa), amino (—NH$_2$), cyanide (—CN), sulfonyl (—SO$_3$H) and sodium sulfonyl (—SO$_3$Na);

R$_1$ is a group of formula —(CH$_2$)$_m$—R$_2$, wherein m is an integer of 1 to 6 and R$_2$ is selected from the group consisting of alkoxyl (—O-Ak), hydroxyl (—OH), carboxyl (—COOH), and amino (—NH$_2$); and ZY is a bidentate ligand, coordinated with Tc through a combination of electron-donating atoms selected from the group consisting of [O$^-$,S$^-$], [S$^-$,S$^-$], [O$^-$,S], [O,S$^-$], [N,S$^-$], [N$^-$,S], and [N$^-$,S$^-$], wherein ZY is not coordinated with Tc through [N,S$^-$] if R is —CH$_3$ and R$_1$ is —(CH$_2$)$_2$—OCH$_3$.

According to another aspect, the invention refers to a radiopharmaceutical composition suitable for protein targeted SPECT imaging comprising at least one compound of the invention, in admixture with one or more physiologically acceptable carriers, diluents or excipients.

A further aspect of the invention relates to a process for the preparation of the compounds of general formula I consisting in the incorporation, in mild conditions, of targeting molecules into a [$^{99m}$Tc(N)(PNP)]-based compound without impairing the biological activity of the substances.

The invention further relates to a kit suitable for the preparation of the compounds of the invention.

DETAILED DESCRIPTION OF THE INVENTION

In a first aspect, the invention relates to novel Technetium heterocomplexes of general formula I:

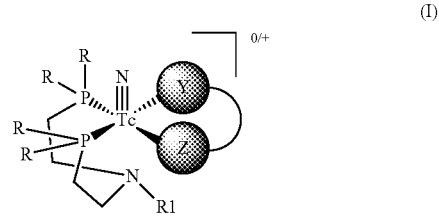

(I)

wherein Tc, R, R$_1$ and ZY are as defined above.

In one embodiment, in the above formula (I), R is selected from the group consisting of hydrogen (—H), methyl (—CH$_3$), hydroxymethyl (—CH$_2$OH), ethyl (—CH$_2$CH$_3$), and carboxyethyl (—CH$_2$CH$_2$COOH).

In another embodiment, the invention relates to compounds of formula (I) in which m is 2 and R$_2$ is methoxyl (—OCH$_3$).

In another embodiment, the invention relates to compounds of formula (I) in which n is 1 and A is hydroxyl (—OH).

In one preferred embodiment the invention relates to water soluble Technetium heterocomplexes according to the above formula (I), of the type [$^{99m}$Tc(N)(PNP3OH)(YZ)]$^{0/+}$, wherein PNP3OH is N,N-bis[(bis-hydroxymethylphosphino)ethyl]methoxyethylamine, and having the formula (II):

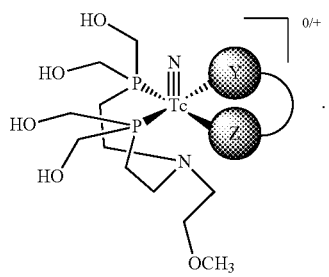

(II)

In another preferred embodiment the invention relates to Technetium heterocomplexes according to the above formula (I), of the type [$^{99m}$Tc(N)(PNP44)(YZ)]$^{0/+}$, wherein PNP44 is N,N-bis[(di-ethylphosphino)ethyl]methoxyethylamine, and having the formula III):

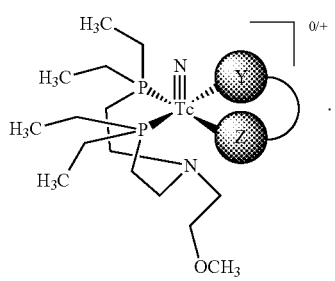

(III)

In another preferred embodiment the invention relates to Technetium heterocomplexes according to the above formula (I), of the type [$^{99m}$Tc(N)(PNP43)(YZ)]$^{0/+}$, wherein PNP43 is N,N-bis[(di-methylphosphino)ethyl]methoxyethylamine, and having the formula (IV):

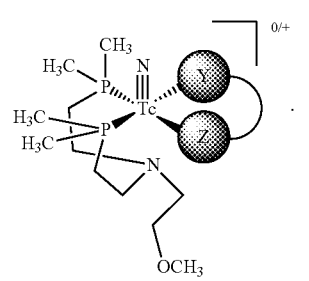

(IV)

In another preferred embodiment the invention relates to Technetium heterocomplexes according to the above formula (I), of the type [$^{99m}$Tc(N)(H$_2$PN(OMe)PH$_2$)(YZ)]$^{0/+}$, wherein H$_2$PN(OMe)PH$_2$ is N,N-bis(phosphinoethyl)methoxyethylamine, and having the formula (V):

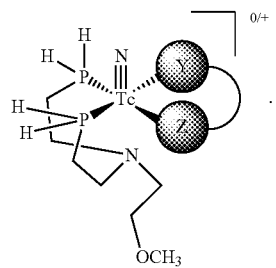

(V)

In another preferred embodiment the invention relates to Technetium heterocomplexes according to the above formula (I), of the type [$^{99m}$Tc(N)(PNP3COOH)(YZ)]$^{0/+}$, wherein PNP3 COOH is N,N-bis[(bis-carboxyethylphosphino)ethyl]methoxyethylamine, and having the formula (VII):

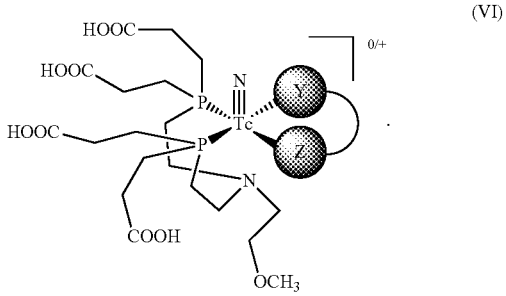

(VI)

In one additional embodiment, preferred are compounds of any one of the above formulas (I), (II), (III), (IV), (V), (VI) in which ZY is coordinated with Tc through a combination of electron-donating atoms selected from the group consisting of [O$^-$,S$^-$], [N,S$^-$], [S$^-$,S$^-$] and [N$^-$,S], wherein ZY is not coordinated with Tc through [N,S$^-$] if R is —CH$_3$ and R$_1$ is —(CH$_2$)$_2$—OCH$_3$.

Preferably, ZY is a cysteine, a cysteine derivative or a dianionic form of the dithiolate derivative.

More preferably, ZY is selected from the group consisting of CysNAc, CysOEt, CysGly, DT-OEt, DT-OH, Cys, Abu-Cys, Cys-Gly-Lys-Gly (SEQ ID NO: 1), and HDTCZ.

The following are preferred examples of compounds of formula (I):
[$^{99m}$Tc(N)(PNP3OH)(CysNAc)], complex 1;
[$^{99m}$Tc(N)(PNP3OH)(CysOEt)]$^+$, complex 2;
[$^{99m}$Tc(N)(PNP3OH)(CysGly)]$^+$, complex 3;
[$^{99m}$Tc(N)(PNP43)(CysGly)]$^+$, complex 4;
[$^{99m}$Tc(N)(PNP3OH)(DT-OEt)], complex 5;
[$^{99m}$Tc(N)(PNP43)(DT-OEt)], complex 6;
[$^{99m}$Tc(N)(PNP3OH)(DT-OH)], complex 7;
[$^{99m}$Tc(N)(PNP43)(DT-OH)], complex 8;
[$^{99m}$Tc(N)(PNP3OH)(Cys)]$^{0/+}$;
[$^{99m}$Tc(N)(PNP43)(Cys)]$^{0/+}$;
[$^{99m}$Tc(N)(PNP3OH)(Abu-Cys)]; and
[$^{99m}$Tc(N)(PNP3OH)(Cys-Gly-Lys-Gly)]$^+$ ("Cys-Gly-Lys-Gly" disclosed as SEQ ID NO: 1).

Even more preferably, ZY is linked to, or is a part of a bioactive molecule, which is preferably thermosensitive.

The bioactive molecule can be Cys-cRGDfK, Biot-Abu-Cys or Glu-Urea-Lys-2-naphthyl-L-Ala-Amc-Cys.

The following are preferred examples of compounds of formula (I), wherein ZY is linked to, or is a part of a bioactive molecule:

[$^{99m}$Tc(N)(PNP3OH)(Cys-cRGDfK)]$^+$, complex 9;
[$^{99m}$Tc(N)(PNP43)(Cys-cRGDfK)]$^+$, complex 10;
[$^{99m}$Tc(N)(PNP3OH)(Biot-Abu-Cys)], complex 11;
[$^{99m}$Tc(N)(PNP3OH)(Glu-Urea-Lys-2-naphthyl-L-Ala-Amc-Cys)]$^+$, complex 12; and
[$^{99m}$Tc(N)(PNP43)(Glu-Urea-Lys-2-naphthyl-L-Ala-Amc-Cys)]$^+$, complex 13.

The bioactive molecule is preferably selected from the group consisting of polypeptides, proteins, antibodies, and aptamers, wherein the antibodies preferably comprise a Fab.

In another aspect, the invention relates to a radiopharmaceutical composition of compounds of formula (I), preferably comprising one or more pharmaceutically acceptable carriers, diluents or excipients.

The radiopharmaceutical composition may be administered by a conventional parenteral mode such as intravenous administration, and the dose thereof is determined depending on a radioactivity level at which imaging is considered possible, in view of the age and body weight of a patient, the condition of disease to be diagnosed, the imager apparatus to be used, etc. The dose is usually 37 MBq to 1.850 MBq, preferably 185 MBq to 740 MBq, in terms of the radioactivity of Tecnetium-99m.

In an additional aspect, the invention relates to the use of the compounds of general formula I, or a radiopharmaceutical composition thereof, for protein targeted SPECT imaging. In a further aspect, the invention relates to a process for the preparation of the compounds of general formula I, using a one-step reaction (Method 2) comprising: reacting, at mild temperature, $^{99m}$Tc-pertechnetate, a reducing agent, a nitrido nitrogen donor, and ZY with a bisphosphinoamine compound of formula (VII)

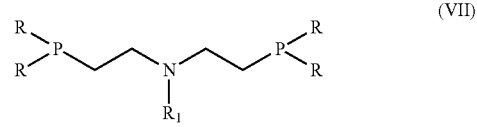

or formula (VIII)

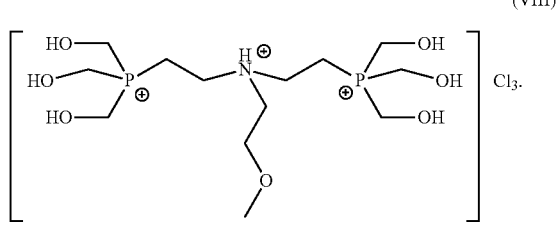

In a preferred embodiment, compounds of the invention may be prepared using a two-step reaction (Method 1), comprising:

a) mixing, at mild temperature, $^{99m}$Tc-pertechnetate, a reducing agent, and a nitrido nitrogen donor, to obtain a reactive $^{99m}$Tc-nitrido precursor [$^{99m}$Tc≡N]$_{int}^{2+}$;
b) converting, at mild temperature and mild pH, the $^{99m}$Tc-nitrido precursor into a heterocomplex by simultaneous addition of a buffer solution containing ZY and a bisphosphinoamine compound of formula (VII) or formula (VIII).

The $^{99m}$Tc-pertechnetate may be a Na[$^{99m}$TcO$_4$] physiological saline solution freshly eluted from a $^{99}$Mo-$^{99m}$Tc generator.

The reducing agent is selected from the group consisting of stannous chloride, sodium hydrogen sulfite, sodium borohydride, tertiary phosphines and tris(m-sulfonatophenyl)phosphine.

The nitrido nitrogen donor is selected from the group consisting of dithiocarbazic acid, dithiocarbazic acid derivatives, hydrazine, hydrazine derivatives and hydrazides derivatives, preferably succinic dihydrazide (SDH).

The buffer is selected from the group consisting of phosphate buffers, sodium phosphate buffers, phosphate buffered saline, and sodium carbonate buffer, preferably sodium phosphate buffers (PB) 0.2 M pH 7.4 or a phosphate buffered saline (PBS) 0.01 M pH 7.4.

For the preparation of the compounds of formula (II), the bisphosphinoamine is preferably provided as N,N-bis[(trishydroxymethylphosphonium)ethyl]methoxyethylamine in a hydrochloride salt form (PNP3OH.HCl), having the formula (VIII), in order to protect the P$^{III}$ toward the oxidation allowing a more convenient purification of the ligand with respect to the corresponding PNP3OH and the storage for long period also under aerobic conditions.

As shown in FIG. 1, the collected data display a high oxidation stability of both PNP3OH.HCl and PNP3OH (weeks). An immediate conversion of the phosphonium salt into PNP3OH is observed after the addition of carbonate buffer or phosphate buffer.

An exemplificative implementation of the above general procedures leading to the compounds of the invention is schematized in the following Scheme:

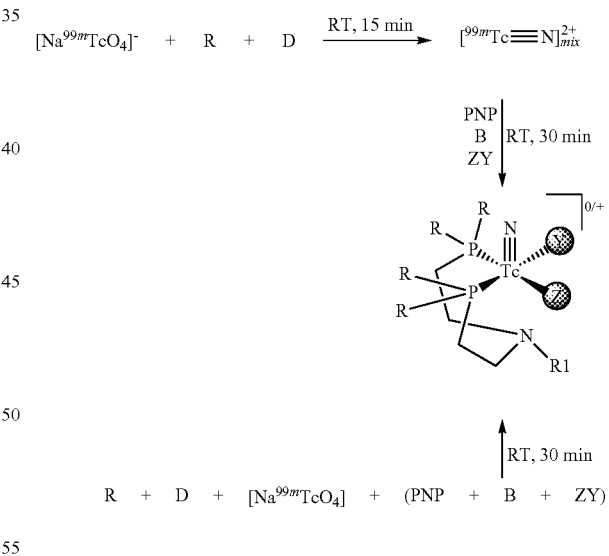

Specific examples of preparation of preferred compounds of formula (I) according to the invention are moreover provided in the following experimental section, constituting a general reference to the operative conditions being employed in the above processes.

Although not willing to be bound by any particular theory, the Applicant considers that the attachment of groups with small steric hindrance or characterized by hydrophilic group (such as HOCH$_2$—, CH$_3$CH$_2$—, CH$_3$—, H—, COOHCH$_2$CH$_2$—) on the P atoms of the PNP ligand dramatically changes the physico-chemical properties of the [$^{99m}$Tc(N)(PNP)]$^{2+}$ building block thus improving its reactivity toward cysteine, cysteine derivatives and dithiol-based co-ligands and allowing the formation of the final radiolabeled compound in high yield after incubation, in physiological solution and in mild reaction conditions. In these conditions, the $^{99m}$Tc-labeling of (thermo)sensitive active biomolecules, such as peptides, polypeptides, pharmacophore groups, proteins, aptamers, antibodies, is efficient.

As shown in the Experimental part, the radiosynthesis of some representative compounds according to the invention has been performed in mild conditions with high yields; instead, the comparative compounds, in the same conditions only changing the groups attached on the P atoms of the PNP, have been formed in low yields.

By using the [$^{99m}$Tc(N)(PNP3OH)]$^{2+}$ building block, to label small, medium or large molecules, the radiochemical yield (RCY) was always higher than 85%, ranging from 85 to 97% as a function of the nature of YZ, and, in all the cases, the radiosynthesis was completed after 30 min at RT, with no significant variation of the RCY by extending the incubation time to 60 min at RT. By using the [$^{99m}$Tc(N)(PNP43)]$^{2+}$ building block, to label small and medium molecules, the RCY was in the range 70-92% as a function of the nature of YZ. In these cases, the radiosynthesis was completed after 30 or 60 min at RT.

Labeling efficiency has also been investigated by varying the concentration of ZY. For complex 1 and complex 2 (FIG. 7), high RCYs were achieved with an amount of ZY in the range of 3-0.05 mg for complex 1 and 3-0.01 mg for complex 2. For complex 7 (Table 9), high RCYs were achieved in a wide range of concentrations of DT-OH. It is worth to note that very high, almost optimal, RCYs were observed with DT-OH concentrations of $1.26 \times 10^{-6}$ M and $6.29 \times 10^{-7}$ M. For complex 9 (FIG. 8), high RCYs were achieved with an amount of Cys-cRGDfK in the range of 0.2-0.05 mg. Thus, both cysteine and dithiolate derivate co-ligands carrying functional group suitable for the coupling with bioactive molecules represent optimal chelating systems for incorporating a molecular vector into [$^{99m}$Tc(N)(PNP)]-scaffold and their absence would prevent the synthesis of the compounds according to the invention (Table 8).

The radiosynthesis was also characterized by high specificity and selectivity, as confirmed by the HPLC profiles of the compounds of formula [$^{99m}$Tc(N)(PNP3OH)(YZ)]$^{o/+}$ (FIG. 4, FIG. 6A, FIG. 6B, FIG. 13, FIG. 14) for the absence of peaks resulting from unbound $^{99m}$Tc(N)-intermediates or [$^{99m}$Tc(N)(PNP3OH)]$^{2+}$ building block. In particular, as shown in FIG. 5, complex 1 and complex 2 were stable within 18 h in the reaction solution at pH 7.4 (only at pH 9, a progressive degradation was observed).

Moreover, transchelation studies have been performed for some compounds monitoring by HPLC the radiochemical purity (RCP) of the complexes in presence of an excess (10 mM) of exchanging ligands, such as glutathione (GSH) or Cys, over the time. Considering the monocationic species (complex 2 and complex 9), a higher stability toward Cys transchelation was proved, with respect to the neutral complexes (complex 1 and complex 11). The % RCP after 3 and 24 h of incubation were 65.93 and 23.32 for complex 2 and 75.93 and 27.31 for complex 9. Nevertheless, in all cases challenge studies carried out with Cys 1 mM showed a reduction of the transchelation rate of the complexes, which suggested a good in vivo stability toward transchelation reaction. For [$^{99m}$Tc(N)(PNP3OH)(Cys-Gly-Lys-Gly-ApoMb)]$^+$ ("Cys-Gly-Lys-Gly" disclosed as SEQ ID NO: 1), challenge experiments with an excess of Cys, GSH and EDTA (10 mM) show that these agents do not affect the stability of the radiolabeled protein and no non-specific bounds between the [$^{99m}$Tc(N)(PNP3OH)]$^{2+}$ moiety and unspecific binding site of the cys-protein conjugate were detected.

The binding to the serum proteins and biotransformation of some radio-complexes in blood and tissue homogenates has been assessed in vitro by incubating the purified compound at 37° C. for 3 h in human and rat sera (complex 1, complex 2, complex 9) as well as in rat liver and rat kidneys homogenates (complex 9) to predict and estimate the in vivo stability and resistance to the proteolytic degradation process. In general, after 15 min incubation 10-15% of the total activity has been found associated with the plasma proteins. No variation of the percentage of the associate radio-complex was observed over the time. For the various compounds, the different affinity for the plasma proteins was in agreement with their high hydrophilic character. Complex 1, complex 2 and complex 9 showed high sera stability with negligible proteolytic degradation caused by endogenous peptidases. For illustrative purpose FIG. 11 displays the HPLC profiles of complex 9 after incubation, at 37° C. for 2 h, in: a) human serum, b) rat serum, c) rat kidneys homogenate and d) rat liver homogenate. All the peaks were found to be coincident with the control to indicate a remarkable in vitro stability of the radiolabeled peptide.

The preliminary evaluation of the binding characteristics of complex 9 and complex 11 has been performed to investigate the impact of the building block on the receptor binding affinity of the bioactive molecules, biotin and RGD peptide. These results (FIG. 9 and FIG. 10) clearly show that the high hydrophilic character and the presence of hydroxymethyl groups on the phosphine donor atoms in the [$^{99m}$Tc(N)(PNP3OH)]$^{2+}$ building block do not affect the binding properties of the bioactive molecule and the radiolabeled compounds are recognized by the corresponding molecular target.

Figure 12:
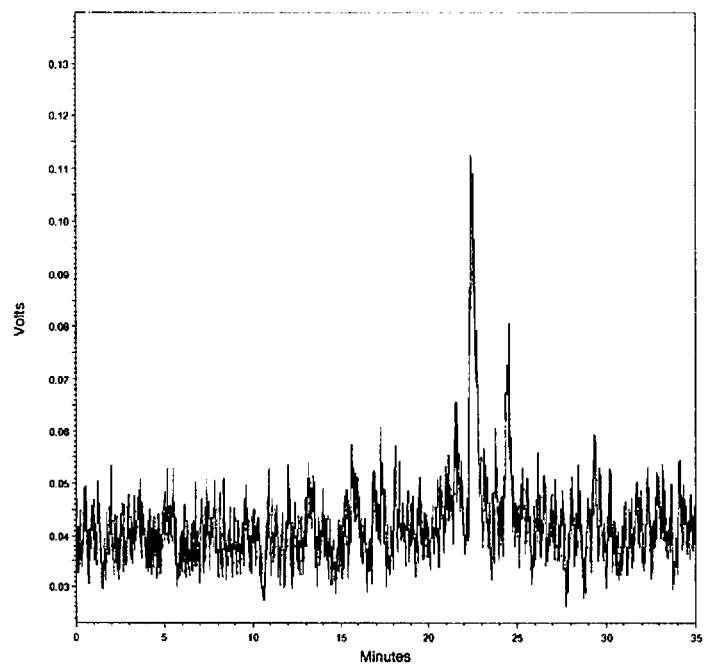
FIG. 12 represents the HPLC profiles of the urine collected at 4 h p.i. complex 9. HPLC analysis was performed with a Reverse Phase Vydac 218TP C18 precolumn (5 µm 4,6×45 mm) and Vydac 218TP C18 column (5 µm 4.6×250 mm). UV detector: $\lambda$=215 m; flow rate of 1 mL/min. Solvents: A H$_2$O TFA 0.1%; B AcCN THF 0.1%. Gradient: 0 min, % B=5; 3-25 min, % B=25; 28-29 min, % B=80; 29-32 min, % B=80; 32-34 min, % B=5; 34-35 min, % B=5.

Ex vivo biodistribution studies of complex 1, complex 2 and complex 9 have been assessed in healthy animals to investigate their pharmacokinetic profiles (organ uptake and excretion pathways) and in vivo stability. Data clearly show favorable pharmacokinetic profiles characterized by a rapid blood clearance and elimination from the non-target tissues within the first 60 min p.i. and excretion properties from the urine (Tables 9 and 10). The effective clearance from the blood and from the other organs reflects the high polarity and water solubility of the complexes, mainly produced by the presence of the new substituents on the P atoms of the PNP ligand. For all the complexes, low $^{99m}$Tc activity was found in the thyroid and in the stomach to indicate that no in vivo decomposition occurred. For complex 9 collected from the in vivo metabolism studies clearly showed that the targeting molecule remained stably incorporated into the structure of the final complex (FIG. 12).

In addition, for complex 9 the in vivo integrin targeting properties have been evaluated in M21 (integrin positive) and M21L (integrin negative) melanoma bearing mice. The organ uptakes expressed as the percentage of injected activity per gram of tissue (% IA/g) and the tumor-to-background ratios obtained at 2 h p.i. are summarized in Table 12. Complex 9 exhibited a good localization in M21 positive tumor (4.38±0.69): the activity was significantly higher with respect to the control (M21L). Thus the high M21-to-M21L ratio along with the high tumor-to-background ratios, clearly showed that the uptake of complex 9 by $\alpha_v\beta_3$ positive cells is receptor-mediated and that the radiolabeled peptide specifically localizes in tumor expressing $\alpha_v\beta_3$ integrin, whereas fails to accumulate in tumor which no express the target.

These results render the compounds of the invention suitable for protein targeted SPECT imaging.

The invention further relates to a kit suitable for preparation of the compounds of general formula I, which comprises a container 1 comprising the reducing agent and the nitrido nitrogen donor, a container 2 comprising ZY and a bisphosphinoamine compound of formula (VII) or formula (VIII), wherein the reducing agent, the nitrido nitrogen donor, ZY and the bisphosphinoamine compound are as defined above.

By using the method of the invention, the $^{99m}$Tc-pertechnetate is placed in the container 1, while the buffer solution is placed in the container 2 to dissolve the contents and a definite amount of the resulting solution is rapidly placed in the vial 1. The vial is shacked and left to react at mildtemperature, whereby the Technetium heterocomplex is obtained.

The kit may, alternatively, comprise three containers, wherein the container 3 comprises a reducing agent and a nitrido nitrogen donor, the container 4 comprises ZY, and the container 5 comprises a bisphosphinoamine compound of formula (VII) or formula (VIII).

The bisphosphinoamine ligand N,N-bis[(bis-carboxyethylphosphino)ethyl]methoxyethylamine (PNP3COOH) can be prepared following the multistep procedure sketched in scheme outline for the PNP43, using in the last step 3-bromo-propionic acid or 3-iodo-propionic acid instead of methyl-iodide. Alternatively, last step can be carried out following the procedure described in Journal of Molecular Catalysis A: Chemical 116 (1997) 191-198. Briefly, PNP3COOH can be prepared by radical addition of allyl carboxylic acid sodium salt to H$_2$PN(OMe)PH$_2$ dissolved in methanol in the presence of VAZO 67, 2,2'-azobis(isobutyronitrile) and heating the solution at 60° C. for 48 h. The reaction mixture is cooled to room temperature. The precipitate is collected on a fritted glass funnel, rinsed with methanol to remove unreacted allyl carboxylic acid sodium salt, and then dried in vacuum.

The bisphosphinoamine ligand N,N-bis(phosphinoethyl) methoxyethylamine (H$_2$PN(OMe)PH$_2$) can be prepared following the first and the second step of the procedure sketched in scheme outlined for the PNP43.

The complex [$^{99m}$Tc(N)(PNP3OH)(DTCZ)]$^+$ can be prepared according to the two-step and one-step procedure (Method 1 and 2). Following the Method 1 with the hydroalcoholic solution in PB, Na[$^{99m}$TcO$_4$] (0.400 ml, 185 MBq) is added to a vial containing SDH (2.5 mg) and SnCl$_2$ (0.1-0.005 mg suspended in 0.100 ml of saline). The vial is kept at room temperature for 15 min giving a mixture of $^{99m}$Tc-nitrido precursors [$^{99m}$Tc≡N]$_{int}^{2+}$. Then PNP3-OH.HCl (1 mg dissolved in 0.200 ml of PB 0.2 M pH 7.4) and HDTCZ (1-0.01 mg in 0.3 ml of EtOH) are added and the reaction mixture is left standing at RT for 60 min. The pH of the reaction mixture, measured at the end of the reaction, should be 7 and the volume should be 1 ml. Following the Method 2 with the hydroalcoholic solution in PB, to a vial containing SDH (2.5 mg) and SnCl$_2$ (0.10 mg suspended in 0.10 ml of saline) is added Na[$^{99m}$TcO$_4$] (0.400 ml; 185 MBq), rapidly followed by PNP3OH.HCl (1 mg in 0.200 ml of PB 0.2 M pH 7.4) and HDTCZ (0.1-0.005 mg in 0.3 ml of EtOH). The reaction mixture is left standing at RT for 60 min. The pH of the reaction mixture, measured at the end of the reaction, should be 7 and the volume should be 1 ml. Following the Method 2 with the hydroalcoholic solution in PBS, to a vial containing SDH (2.5 mg) and SnCl$_2$ (0.10 mg suspended in 0.10 ml of saline) is added Na[$^{99m}$TcO$_4$] (0.100 ml; 185 MBq), rapidly followed by PNP3OH.HCl (1 mg in 1.00 ml of PBS 1×) and HDTCZ (0.1-0.005 mg in 0.3 ml di EtOH). The reaction mixture is left standing at RT for 60 min. The pH of the reaction mixture, measured at the end of the reaction, should be 7 and the volume should be 1.5 ml.

The complex [$^{99m}$Tc(N)(PNP)(DTCZ)]$^+$ (PNP=PNP43, PNP44, PNP3COOH) can be prepared according to the two-step and one-step procedure (Method 1 and 2). Following the Method 1, Na[$^{99m}$TcO$_4$] (0.400 ml, 185 MBq) is added to a vial containing SDH (2.5 mg) and SnCl$_2$ (0.100 mg suspended in 0.100 ml of saline). The vial is kept at room temperature for 15 min giving a mixture of $^{99m}$Tc-nitrido precursors [$^{99m}$Tc≡N]$_{int}^{2+}$. Then PNP (9.96 10$^{-4}$ mmol dissolved in 0.1 ml of EtOH), HDTCZ (0.1-0.005 mg in 0.2 ml di EtOH) and PB (0.200 ml, 0.2 M pH 7.4) are added, and the reaction mixture is left standing at RT for 60 min. The pH measured at the end of the reaction, should be 7 and the volume should be 1 ml. Following the Method 2, to a vial containing SDH (2.5 mg) and SnCl$_2$ (0.10 mg suspended in 0.10 ml of saline) is added Na[$^{99m}$TcO$_4$] (0.400 ml; 185 MBq), rapidly followed by PNP (PNP43, 0.25 mg dissolved in 0.1 ml of EtOH), HDTCZ (1-0.01 mg in 0.2 ml di EtOH) and PB (0.200 ml, 0.2 M pH 7.4). The reaction mixture is left standing at RT for 60 min. The pH measured at the end of the reaction, should be 7 and the volume should be 1 ml.

Other [$^{99m}$Tc(N)(PNP)(YZ)]$^{+/0}$ compounds, containing BAM, can be synthesized through the same or similar processes with the YZ-final molar concentration in the range 10$^{-5}$-10$^{-6}$ M.

Non-limiting examples of preferred compounds of the invention and intermediates for their preparation are reported in the following section, aimed to illustrate the invention in greater detail without limiting its scope.

EXPERIMENTAL EXAMPLES

Synthesis of PNP

Example 1: Synthesis of N,N-bis[(bis-hydroxymethylphosphino)ethyl] methoxyethylamine (PNP3OH)

PNP3OH was obtained by using the following synthetic procedure:

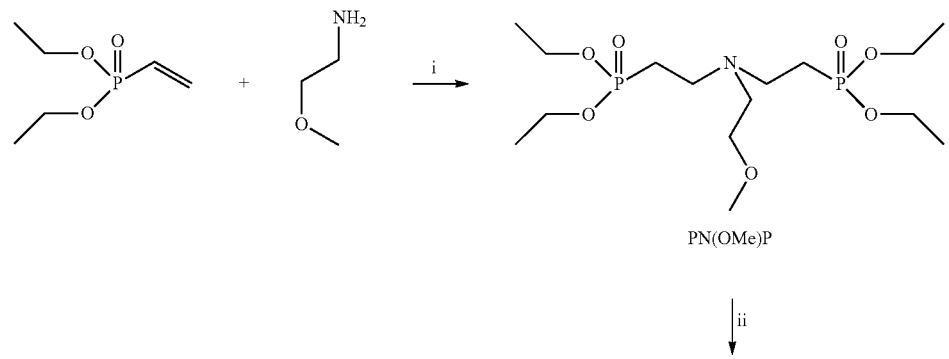

PN(OMe)P

↓ ii

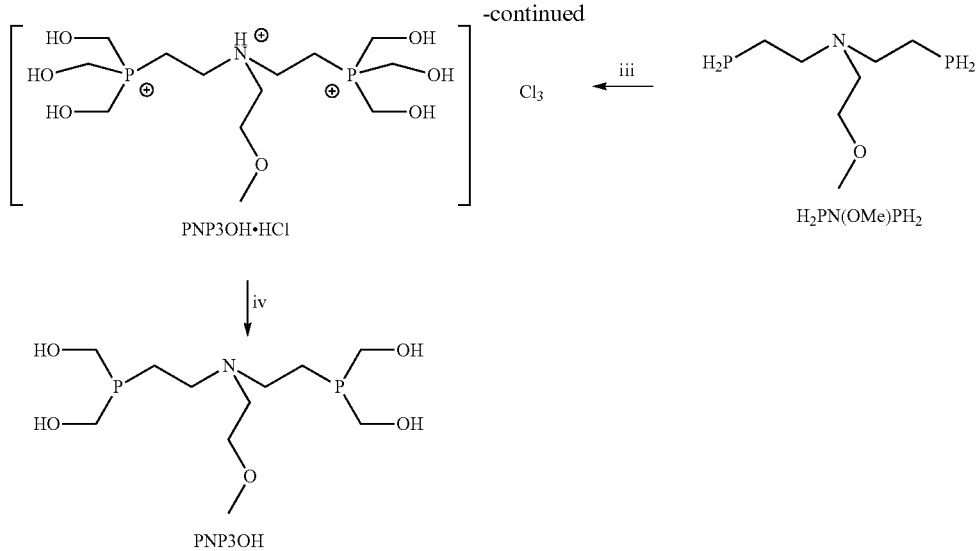

PNP3OH·HCl

PNP3OH

Reagents and conditions: i) LiClO₄, 75° C., 24 h; ii) LiAlH₄, Et₂O dry, 0° C.; iii) EtOH/HCl, CH₂O, iv) Na₂CO₃ 0.5M

Synthesis of PN(OMe)P

In a 10 ml glass vial, methoxyethylamine (0.15 ml, 2.5 mmol), diethylvinylphosphonate (5 mmol) and lithium perchlorate (532 mg, 5 mmol) were added. The vial was filled with di-nitrogen, hermetically capped and immersed completely in an oil bath and heated at 75° C. under stirring for 24 h. After cooling, the vial was opened and the content was treated with chloroform (3×2 ml). The combined organic phases were transferred into a separating funnel and treated with water (2×6 ml). The organic phases were collected and treated with Na₂SO₄ (200 mg) to completely remove the residual water then filtered. The solvent was removed with a rotavapor and the oily residue was left in vacuum (0.1 torr, 40° C.) for 60 min to remove any possible residue of diethylvinylphosphonate. A light yellow oil was obtained. Yield 87%.

$^{31}P\{^{1}H\}$ NMR (121.44 MHz, CDCl₃): δ (ppm)=31.24 (s).

$^{1}H$ NMR (300 MHz, CDCl₃): δ (ppm)=4.08, (m, 8H, (CH₃CH₂O)₂PO); 3.44, (t, 2H, NCH₂CH₂O); 3.33, (s, 3H, NCH₂CH₂OCH₃); 2.82-2.77, (m, 4H, P(O)CH₂CH₂N); 2.64, (t, 2H NCH₂CH₂O); 1.96-1.86, (m, 4H, P(O)CH₂CH₂N); 1.31, (t, 12H, CH₃CH₂OPO).

Synthesis of N,N-bis(phosphinoethyl)methoxyethylamine (H₂PN(OMe)PH₂)

The manipulations were conducted under an inert atmosphere (nitrogen) using standard Schlenk techniques. PN(OMe)P (0.533 g, 1.32 mmol) was weighed in a two-necked round-bottom flask (100 ml). Anhydrous diethylether (5 ml) was added under nitrogen. The flask was cooled at 0° C. and LiAlH₄ 1 M in diethylether (8 ml, 8 mmol) was slowly added through a rubber septum. After the addition, the bath was removed and the mixture was stirred for further 30 min. The mixture was then cooled again at 0° C. and quenched with a degassed Na₂SO₄ saturated solution (3 ml). Further anhydrous Na₂SO₄ was added to completely remove the residual water. The inorganic solid was separated by filtration, washed with diethylether (5 ml×3) and the ethereal solution and washing aliquots were collected in a double neck flask. A colorless liquid remained after solvent elimination by means of a di-nitrogen stream and vacuum. Yield 88%.

$^{31}P\{^{1}H\}$ NMR (121.44 MHz, CDCl₃): δ (ppm)=−145.49.

$^{1}H$ NMR (300 MHz, CDCl₃): δ (ppm)=3.45 (t, H, NCH₂CH₂OCH₃); 3.34 (s, 3H, NCH₂CH₂OCH₃); 2.93, 2.28 (2t, 4H, PH₂CH₂); 2.65 (m, 6H, PH₂CH₂CH₂NCH₂CH₂O); 1.64-1.62 (m, 4H, PH₂CH₂CH₂N).

Synthesis of N,N-bis[(tris-hydroxymethylphosphonium) ethyl]methoxyethylamine hydrochloride (PNP3OH.HCl)

In a two-necked round-bottom flask containing H₂PN(OMe)PH₂ (530 mg, 1.31 mmol), degassed EtOH was added (6 ml) followed by formaldehyde 37% (0.59 ml, 7.86 mmol) and HCl (3 M, 1.5 ml). The reaction mixture was stirred at room temperature for 3 h under di-nitrogen atmosphere. The solution was cleared. The solvent was completely eliminated with a rotavapor and then applying a high vacuum, thus giving a white wax of the phosphonium salt, PNP3OH.HCl. Yield 52%.

$^{31}P\{^{1}H\}$ NMR (121.44 MHz, CDCl₃): δ (ppm)=28.69 (s).

$^{1}H$ NMR (300 MHz, CDCl₃): δ (ppm)=4.70, (s, 12H (HOCH₂)₃P); 3.67, (m, 6H (PCH₂CH₂)₂NCH₂CH₂O); 3.42, (m, 2H, NCH₂CH₂OCH₃); 3.30, (s, 3H, NCH₂CH₂OCH₃); 2.89, (m, 4H PCH₂CH₂N).

ESI-MS (m/z) are consistent with the free PNP3OH (m/z 316, [M+H]⁺).

Synthesis of N,N-bis[(bis-hydroxymethylphosphino) ethyl]methoxyethylamine (PNP3OH)

Free PNP3OH was obtained by dissolving the PNP3OH.HCl salt in 0.2 M sodium phosphate buffer (pH 7.4) or in 0.5 M carbonate buffer (pH 9).

PNP3OH.HCl and PNP3OH were highly soluble in water and soluble in alcohols.

Example 2: Stability Studies of PNP3OH.HCl and PNP3OH

Aqueous stock solutions of PNP3OH.HCl were prepared by dissolving 5 mg of ligand in: i) 1 ml of distillate water; ii) 1 ml of carbonate buffer 0.5 M, pH 9; iii) 1 ml of sodium phosphate buffer 0.2, pH 7.4. These solutions were stirred in open air and aliquots were analyzed by $^{31}$P NMR at various time intervals.

The oxidative stability of PNP3OH.HCl salt and of the corresponding free PNP3OH was assessed by $^{31}$P {$^{1}$H} NMR (FIG. 1).

Example 3: Synthesis of N,N-bis[(di-methylphosphino)ethyl]methoxyethylamine (PNP43)

PNP43 was obtained by using the following synthetic procedure:

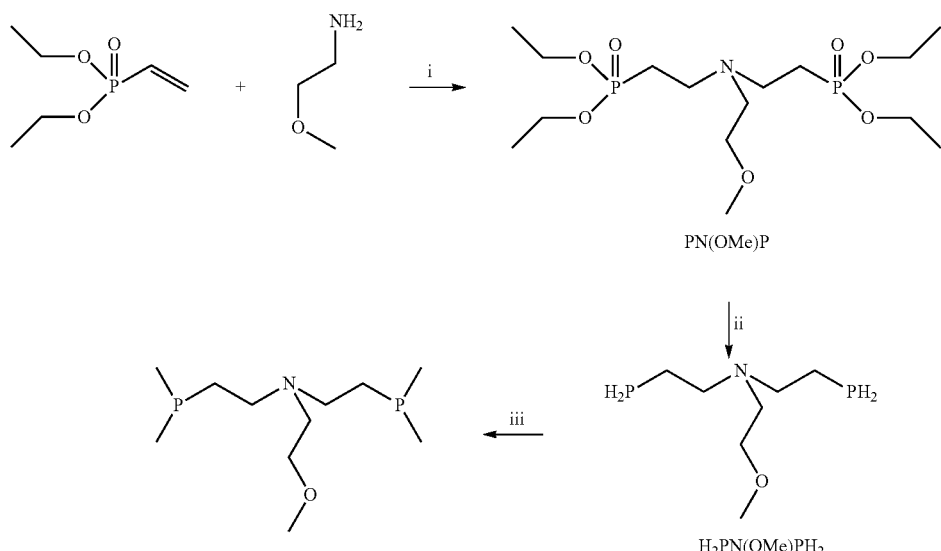

Reagents and conditions: i) LiClO$_4$, 75° C., 24 h; ii) LiAlH$_4$, Et$_2$O dry, 0° C.; iii) n-BuLi, THF -78° C., CH$_3$I.

Synthesis of PN(OMe)P. In a 10 ml glass vial, methoxyetilamine (0.15 ml, 2.5 mmol), diethylvinylphosphonate (0.768 ml, 5 mmol) and lithium perchlorate (691 mg, 5 mmol) were added. The vial was filled with di-nitrogen, hermetically capped and immersed completely in an oil bath and heated at 75° C. under stirring for 24 h. After cooling, the vial was opened and the content was treated with chloroform (3×2 ml). The combined organic phases were transferred into a separating funnel and treated with water (2×6 ml). The organic phases were collected and treated with Na$_2$SO$_4$ (200 mg) to completely remove the residual water then filtered. The solvent was removed with a rotavapor and the oily residue was left in vacuum (0.1 torr, 40° C.) for 60 min to remove any possible residue of diethylvinylphosphonate. A yellow oil was obtained. Yield 87%.

$^{31}$P{$^{1}$H} NMR (121.44 MHz, CDCl$_3$): δ (ppm)=31.24 (s).

$^{1}$H NMR (300 MHz, CDCl$_3$): δ (ppm)=4.08, (m, 8H, (CH$_3$CH$_2$O)$_2$PO); 3.44, (t, 2H, NCH$_2$CH$_2$O); 3.33, (s, 3H, NCH$_2$CH$_2$OCH$_3$); 2.82-2.77, (m, 4H, P(O)CH$_2$CH$_2$N); 2.64, (t, 2H NCH$_2$CH$_2$O); 1.96-1.86, (m, 4H, P(O)CH$_2$CH$_2$N); 1.31, (t, 12H, CH$_3$CH$_2$OPO).

Synthesis of N,N-bis(phosphinoethyl)methoxyethylamine (H$_2$PN(OMe)PH$_2$)

The manipulations were conducted under an inert atmosphere (nitrogen) using standard Schlenk techniques. PN(OMe)P (0.533 g, 1.32 mmol) was weighed in a two-necked round-bottom flask (100 ml). Anhydrous diethylether (5 ml) was added. The flask was cooled at 0° C. and LiAlH$_4$ 1 M in diethylether (8 ml, 8 mmol) was slowly added through a rubber septum. After the addition, the bath was removed and the mixture was stirred for further 30 min. The mixture was then cooled again at 0° C. and quenched with a degassed Na$_2$SO$_4$ saturated solution (3 ml). Further anhydrous Na$_2$SO$_4$ was added to completely remove the residual water. The inorganic solid was separated by filtration, washed with diethylether (5 ml×3) and the ethereal solution and washing aliquots were collected in a double neck flask. A colorless liquid remained after solvent elimination by means of a di-nitrogen stream and vacuum. Yield 88%.

$^{31}$P {$^{1}$H} NMR (121.44 MHz, CDCl$_3$): δ (ppm)=−145.49.

$^{1}$H NMR (300 MHz, CDCl$_3$): δ (ppm)=3.45 (t, H, NCH$_2$CH$_2$OCH$_3$); 3.34 (s, 3H, NCH$_2$CH$_2$OCH$_3$); 2.93, 2.28 (2t, 4H, PH$_2$CH$_2$); 2.65 (m, 6H, PH$_2$CH$_2$CH$_2$NCH$_2$CH$_2$O); 1.64-1.62 (m, 4H, PH$_2$CH$_2$CH$_2$N).

Synthesis of N,N-bis[(di-methylphosphino)ethyl]methoxyethylamine (PNP43)

In a two-necked round-bottom flask H$_2$PN(OMe)PH$_2$ (530 mg, 1.31 mmol) was dissolved in dry THF (10 ml), under di-nitrogen atmosphere. n-BuLi 2.5 M in hexane (1.8 ml, 4.52 mmol) was slowly added. The color turned from yellow to brown. The flask was cooled at −78° C. and through a pressure equalizing funnel methyl-Iodide (1.02 ml, 4.52 mmol), dissolved in THF (10 ml), was slowly added. The solution was cleared, then it was left under stirring until the temperature of the bath reaches −20° C. The clear gold-yellow solution was reduced to ⅓ of the volume under a dinitrogen stream, cooled at 0° C. and quenched with degassed water (5 ml). The mixture was siphoned in a double neck separator funnel and extracted with degassed diethylether (10 ml×3). The organic layers were collected over anhydrous $Na_2SO_4$. The solid was separated by filtration and the solvent was evaporated under a dinitrogen stream and vacuum. Yield 79%.

$^{31}P\{^1H\}$ NMR (121.44 MHz, $CDCl_3$): δ (ppm)= −52.83 (s).

$^1H$ NMR (300 MHz, $CDCl_3$): δ (ppm)=3.51, (t, 2H, $NCH_2CH_2OCH_3$); 3.39 (s, 3H, $NCH_2CH_2OCH_3$) 2.71 (m, 6H ($PCH_2CH_2)_2N$, $NCH_2CH_2O$); 1.43 (m, 4H, $PCH_2CH_2)_2$ N; 1.08 (s, 12H, —$P(CH_3)_4$.

ESI-MS: (m/z 252, $[M+H]^+$).

Example 4: Synthesis of N,N-bis[(di-ethylphosphino)ethyl]methoxyethylamine (PNP44)

PNP44 was obtained by using the following synthetic procedure. In principle N,N-bis(di-ethylphosphinoethyl) methoxyethylamine (PNP44) can be prepared following the multistep procedure sketched in the scheme outlined for PNP43, using in the final step ethyl-bromide (1.02 ml, 4.52 mmol) instead of methyl-iodide.

Thus, the primary phosphine $H_2PN(OMe)PH_2$ (160 mg, 0.822 mmol) was dissolved in dry THF (10 ml), under dinitrogen atmosphere. n-BuLi 2.5 M in hexane (1.480 ml, 3.7 mmol) was slowly added. The color turned to yellow and, after few minutes, the formation of a yellow suspension was observed. The reaction mixture was maintained at RT under agitation for 30 min. Then, the flask was cooled at −78° C. and ethyl-bromide (0.245 ml, 3.29 mmol), dissolved in THF (30 ml), was slowly added through a pressure equalized funnel. The solution cleared, then it was left under stirring until the temperature of the bath reached −20° C. The clear gold-yellow solution was reduced to ⅓ of the volume under a dinitrogen stream, cooled at 0° C. and quenched with degassed water (5 ml). The mixture was siphoned in a double neck separator funnel and extracted with degassed $Et_2O$ (10 ml×3). The organic fractions were combined and treated with anhydrous $Na_2SO_4$. The solid was separated by filtration (G3 frit) under dinitrogen atmosphere and the filtrate was collected in a two-necked 100 ml flask. The solid on the frit was washed with $Et_2O$ (2×10 ml). The combined ethereal phases were evaporated under dinitrogen stream and then under vacuum to afford the final compound. Yield 85%. Purity 80%.

$^{31}P\{^1H\}$ NMR (121.44 MHz, $CDCl_3$): δ (ppm)=−23.59.

$^1H$ NMR (300 MHz, $CDCl_3$): δ (ppm)=3.54 (t, 2H, $NCH_2CH_2OCH_3$); 3.36 (s, 3H, $NCH_2CH_2OCH_3$); 2.77, (m, 2H, $NCH_2CH_2O$; 4H, $PCH_2CH_2N$); 1.61, (m, 4H, $PCH_2CH_2N$); 1.43 (m, 8H, ($CH_3$—$CH_2$-$)_4P$), 1.07 (m, 12H, ($CH_3$—$CH_2$-$)_4P$).

ESI-MS [($CH_3CH_2)_2PCH_2CH_2]_2NCH_2CH_2OCH_3$)], $C_{15}H_{35}NOP_2$, MW=307.22; m/z 308, $[M+H]^+$.

The main side product was characterized as [($CH_3CH_2)_2 PCH_2CH_2]_2N+(CH_2CH_3)(CH_2CH_2OCH_3)$], ESI-MS, $C_{17}H_{40}NOP_2$, MW=336.26; m/z 336, $[M]^+$.

$^{31}P\{^1H\}$ NMR (121.44 MHz, $CDCl_3$): δ (ppm)=−27.67.

Synthesis of Bidentate Ligands ZY

Example 5: Preparation of Cys-Gly-Lys-Gly-ApoMb (SEQ ID NO: 1)

Peptide synthesis. The peptide Cys-Gly-Lys-Gly (SEQ ID NO: 1) was synthesized by the solid-phase method using fluorenyl-methyloxycarbonyl chemistry on a Model PS3 automated synthesizer from Protein Technologies International (Tucson, Ariz., USA). The crude peptide was purified by RP-HPLC using a Vydac C18 semipreparative column (10×250 mm, 10 μm). The RP-HPLC separation was performed by applying a gradient of acetonitrile (AcCN), 0.085% TFA and water, 0.1% TFA of 0% AcCN for 12 min at a flow rate of 2.0 ml/min and from 0 to 80% AcCN in 4 min followed by an isocratic wash at 80% AcCN at a flow rate of 2.5 ml/min. The effluent was monitored by measuring the absorbance at 226 nm. After lyophilisation, Cys-Gly-Lys-Gly (SEQ ID NO: 1) peptide was analyzed by ESI-MS. The amount of purified peptide was estimated by weight measurement. The purified peptide was dissolved in DMSO at a concentration of 50 mM and stored in aliquots at −20° C.

TGase-mediated conjugation of apomyoglobin to Cys-Gly-Lys-Gly (SEQ ID NO: 1) peptide. An aliquot of 1 mg of lyophilized apomyoglobin was dissolved in 20 μl of an aqueous solution of 0.1% TFA and then diluted to 800 μl with 0.1 M sodium phosphate buffer, pH 7.0. After centrifugation, the concentration of ApoMb in the supernatant solution was of 0.77 mg/ml, as determined by measurement of the absorbance at 280 nm. The ApoMb solution of dithiothreitol was added to a final concentration of 194 μM, of Cys-Gly-Lys-Gly (SEQ ID NO: peptide at a molar ratio ApoMb/peptide of 1/30 and of TGase at an enzyme/substrate (E/S) of 1/50 (w/w). The reaction mixture was incubated at 37° C. for 4 hours and then stopped by lowering the pH with an aqueous solution of 1% TFA. Aliquots of the reactions were analyzed by RP-HPLC using a C18 Phenomenex column (150×4.6 mm). The elution was performed by applying a two-step gradient of acetonitrile (AcCN), 0.085% TFA and water, 0.1% TFA from 5 to 40% of AcCN in 5 min and from 40 to 47% in 17 min. The absorbance of the effluent was monitored at 226 nm. Fractions collected from the RP-HPLC analyses were lyophilized and analyzed by ESI-MS. For the purification of ApoMb derivatized with Cys-Gly-Lys-Gly (SEQ ID NO: 1 peptide, semipreparative RP-HPLC was carried out on the same HPLC system but using a Vydac C18 semipreparative column (10×250 mm, 10 μm). The applied gradient was as for the analytical HPLC but at a flow rate of 2 ml/min. Since some fractions of the product contained ApoMb conjugated to a dimer of Cys-Gly-Lys-Gly (SEQ ID NO: 1) peptide due to disulphide bond formation between two peptide molecules (Gly-Lys-Gly-Cys-SS-Cys-Gly-Lys-Gly-ApoMb ("Cys-Gly-Lys-Gly" disclosed as SEQ ID NO: 1)), these samples were reduced and purified by semipreparative RP-HPLC using the same conditions as for the reaction mixture. Reduction was performed by dissolving the ApoMb derivatives (0.5 mg/ml) in an aqueous solution of 0.1% TFA containing 5.9 mM tris(2-carboxyethyl)phosphine (TCEP) followed by incubation at 37° C. for 90 min. The purity of the purified ApoMb derivatives was confirmed by ESI-MS analysis.

Figure 2:
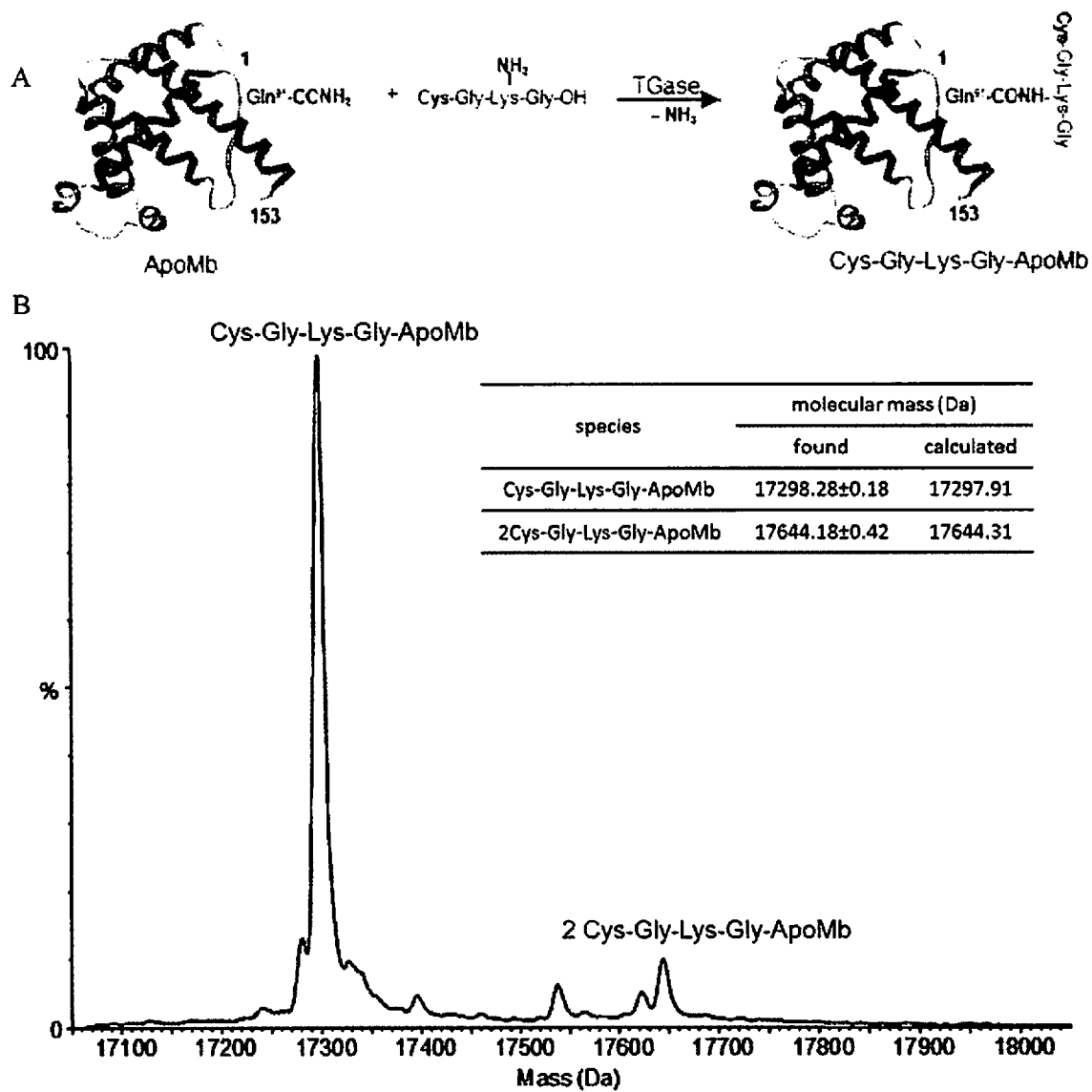
FIG. 2 represents the TGase-mediated conjugation of ApoMb to Cys-Gly-Lys-Gly (SEQ ID NO: 1) peptide. A scheme of the conjugation reaction of ApoMb with Cys-Gly-Lys-Gly (SEQ ID NO: 1) peptide mediated by TGase The three-dimensional structure of ApoMb is constructed from the X-ray structure of horse heart holo myoglobin (PDB file 1YMB) in which the chain segment encompassing helix F (residues 82-97) is represented in a disordered conformation. The image is created using the program WebLab Viewer Pro 4.0 (Molecular Simulations Inc., San Diego, Calif., USA). The approximate position of the amino acid residue Gln91 is indicated. In the TGase mediate reaction, the Lys residue of Cys-Gly-Lys-Gly (SEQ ID NO: 1) peptide is coupled to the Gln91 residue of ApoMb leading to the formation of the product Cys-Gly-Lys-Gly-ApoMb (SEQ ID NO: 1) (A). A deconvoluted ESI mass spectrum of the purified Cys-Gly-Lys-Gly-ApoMb (SEQ ID NO: 1) derivative used for the radiolabeling experiments. The table in the inset reports the calculated and measured molecular masses of the ApoMb derivative (B). "2Cys-Gly-Lys-Gly" discloses "Cys-Gly-Lys-Gly" as SEQ ID NO: 1.
Figure 3A:
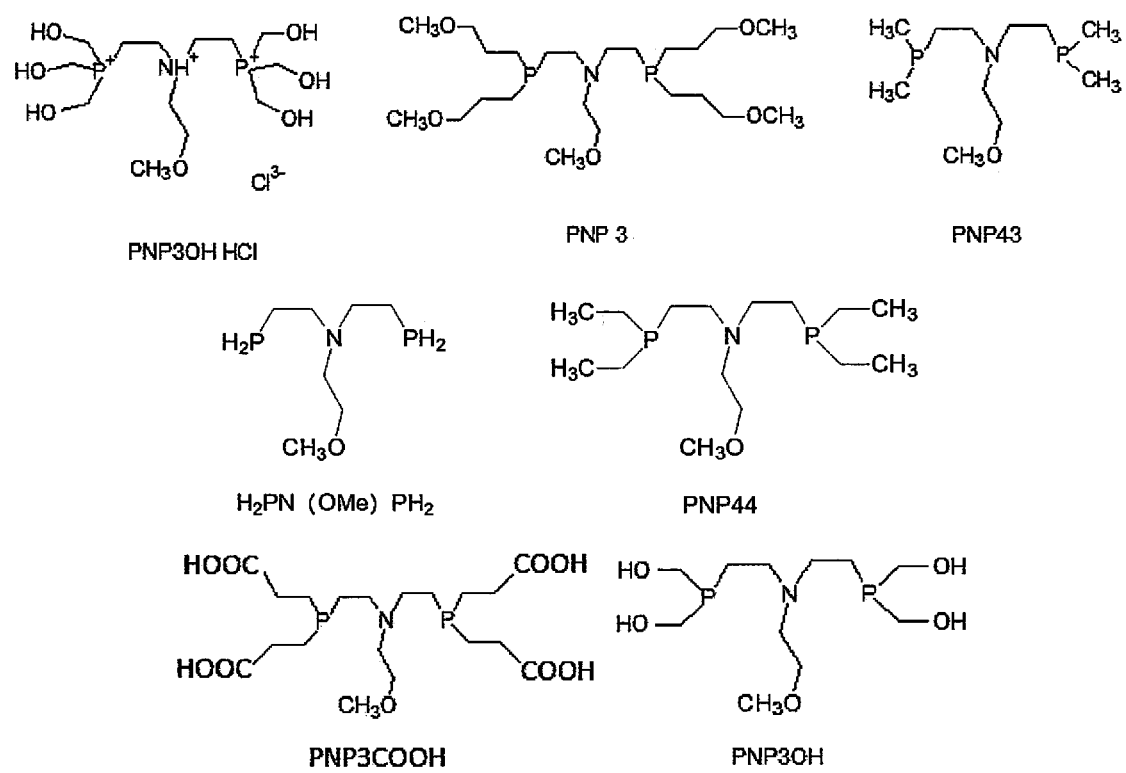
FIG. 3A represents the schematic drawings of the PNP ligands employed in labeling studies.
Figure 3B:
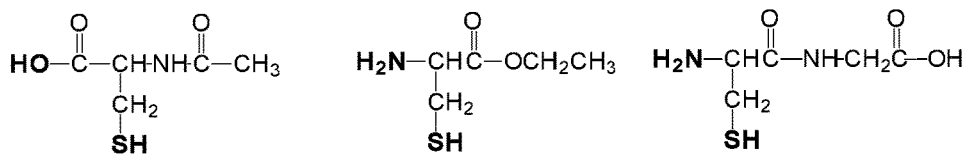
FIG. 3B represents the schematic drawings of the ZY ligands (in the protonated form). Figure discloses SEQ ID NO: 1.
Figure 3B:
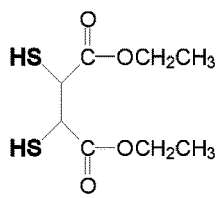
Figure 3B:
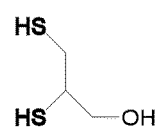
Figure 3B:
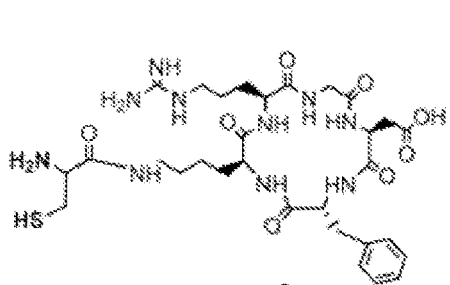
Figure 3B:
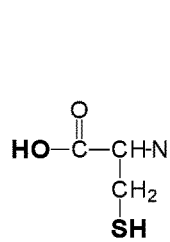
Figure 3B:
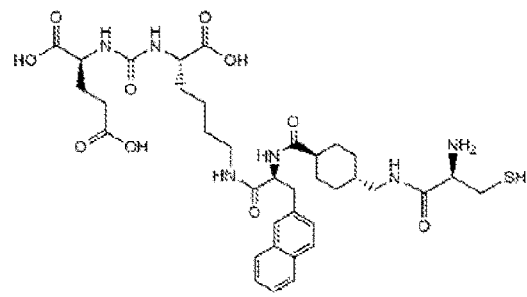
Figure 3B:
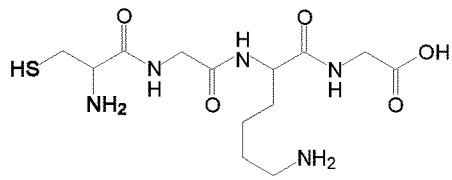
Figure 3B:
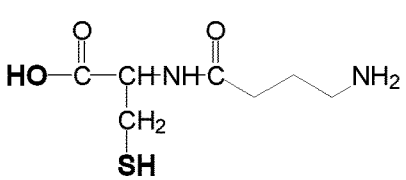
Figure 3B:
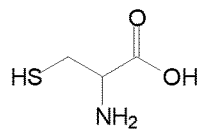
Figure 3B:
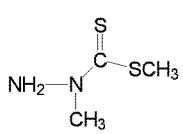

Samples were dissolved in 0.1% formic acid in AcCN: water (1:1) and analyzed in MS positive ion mode. Instrument control, data acquisition and processing were achieved with Masslynx software (Micromass) (FIG. 2).

Example 6: Preparation of Glu-Urea-Lys-2-naphthyl-L-Ala-Amc-Cys

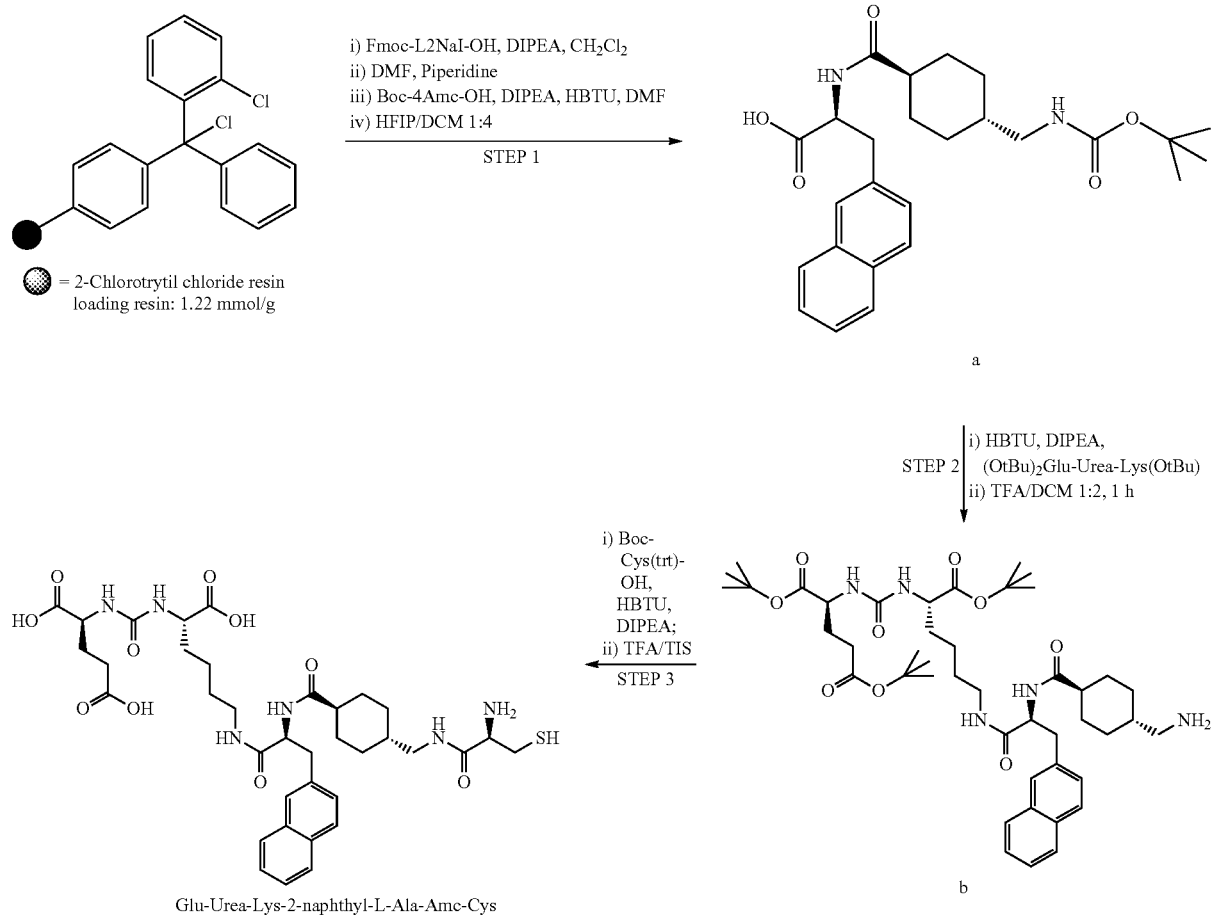

Step 1: 200 mg of a 2-Chlorotrytil chloride resin (loading 1.22 mmol/g) was pre-swelled with 10 ml of $CH_2Cl_2$. The first Fmoc protected AA (Fmoc-L-2Nal-OH) was loaded on the resin during 2.5 h (2 eq., 0.488 mmol, 213.5 mg) with 3 eq. of DIPEA (128 μl). After the anchoring of the first AA, the resin was end-capped with a solution of MeOH/DIPEA 3:0.5 for 30 min. The resin was washed with DMF, and the cleavage solution was added to the reactor (piperidine:DMF 1:4) and stirred for 30 minutes. The resin was washed with DMF and Boc-4-Amc-OH was added (2 eq, 125.6 mg, 0.488 mmol) with 4 eq. of DIPEA (170 μl) and 1.8 eq of HBTU (166.6 mg, 0.439 mmol). After two hours the resin was washed with DMF and the fully protected peptide was cleaved from the resin with a solution of $HFIP/CH_2Cl_2$ 1:4 for 5 minutes. The solvent was evaporated in vacuum and the product a was used in step 2 without further purification.

Step 2: product a (110 mg, 0.244 mmol) was dissolved in $CH_2Cl_2$ and DIPEA (3 eq., 128 μl) and HBTU (0.9 eq., 83 mg) were added to the solution. Then a solution of $(OtBu)_2$ Glu-Urea-Lys(OtBu) (1 eq.) (synthetized as described in Weineisen et al. EJNMMI Research 2014, 4:63) was added to the solution and the reaction mixture was stirred overnight at room temperature. The solvent was evaporated and the crude product was purified by silica gravimetric chromatography. The obtained product was dissolved in 3 ml of $CH_2Cl_2$ at 0° C. 300 μl of TFA were added dropwise and the reaction mixture was stirred for 1 h at 0° C. 10 ml of sat. $NaHCO_3$ were added to the solution and the product was extracted with $CCl_3$. $Et_2O$ was added and the product precipitated. The solvent was evaporated to obtain the fully protected product b.

Step 3: in a round bottom flask 41.5 mg of Boc-Cys(Trt)-OH were dissolved in $CH_2Cl_2$ and 3 eq. of DIPEA and 1 eq. of HBTU were added to the solution. Then, the product b was added to the solution and the reaction mixture was stirred overnight at room temperature. The solution was washed three times with water, then the solvent was evaporated and re-dissolved in a solution of TFA/TIS 95:5 (4 ml). The reaction mixture was stirred overnight at room temperature. The solvent was evaporated and the product precipitated in cold $Et_2O$. The product was purified by preparative HPLC: Atlantis prepD® C18OBD 5 μm (19×100 mm) column. Eluent: (A) 0.1% TFA in $H_2O$, (B) 0.1% TFA in $CH_3CN$. Gradient profile; isocratic at 25% of B for 5.69 min, linear gradient from 25% to 37.5% of B in 2.85 min, linear gradient from 37.5% to 100% in 1.70 min, isocratic at 100% of B for 1.8 min Flow rate; 20 ml/min. 19.8 mg of Glu-Urea-Lys-2-naphthyl-L-Ala-Amc-Cys was isolated; total yield: 4%. The purity of the product was monitored by analytical HPLC, Atlantis DC18 5 μm (4.6×150 mm) column, using the previous gradient profile and mobile phase. Flow rate of 1 ml/min and UV detection at 230 nm. HPLC Purity 99%. qNMR assay: 94% ESI-MS (m/z): calculated mass ($C_{36}H_{51}N_6O_{10}S$): 759.90; found: 759.66. Alternatively, product b can be also prepared by solid-phase synthesis as reported in J. Med. Chem. (2016), 59, 1761-1775. Conjugation of Cys to the immobilized amino function of the peptide sequence can be carried out by solid-phase synthesis. Fully deprotected product can be obtained applying the abovementioned cleavage procedure.

$^{99m}$Tc-Labeling Studies and Characterization
Labeling of Small Size Molecules Example 7: Radiosynthesis of Complex 1, Complex 2, Complex 3, [$^{99m}$Tc(N)(PNP3OH)(ZY)]$^{0/+}$ (ZY=CysNAc; CysOEt; CysGly)

Method 1 (Two-Step) in PB.

Na[$^{99m}$TcO$_4$] (0.500 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3OH.HCl (1 mg dissolved in 0.200 ml of PB 0.2 M pH 7.4) and ZY (0.150-0.005 mg in 0.2 ml of H$_2$O) were added and the reaction mixture was left standing at RT for 60 min. The pH of the reaction mixture, measured at the end of the reaction, was 7.2 and the volume was 1 ml.

Figure 4:
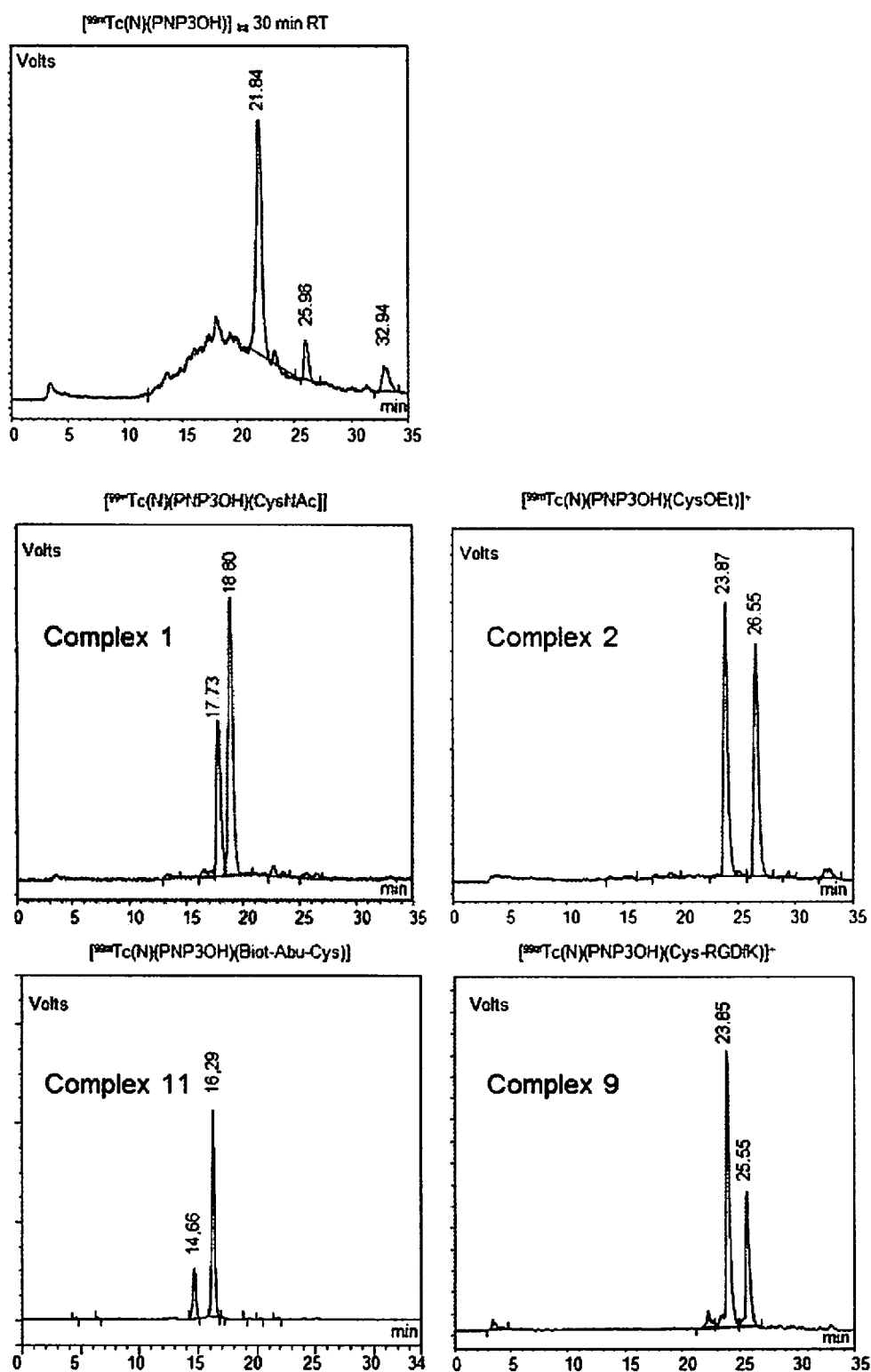
FIG. 4 represents Radiometric HPLC profiles of the obtained complex 1, complex 2, complex 11 and complex 9, collected after 30 min of incubation at RT. RP-HPLC profile of the reaction mixtures indicates the formation, in high yield, of the complexes as a mixture of two syn and anti isomers in different ratios.
Figure 5:
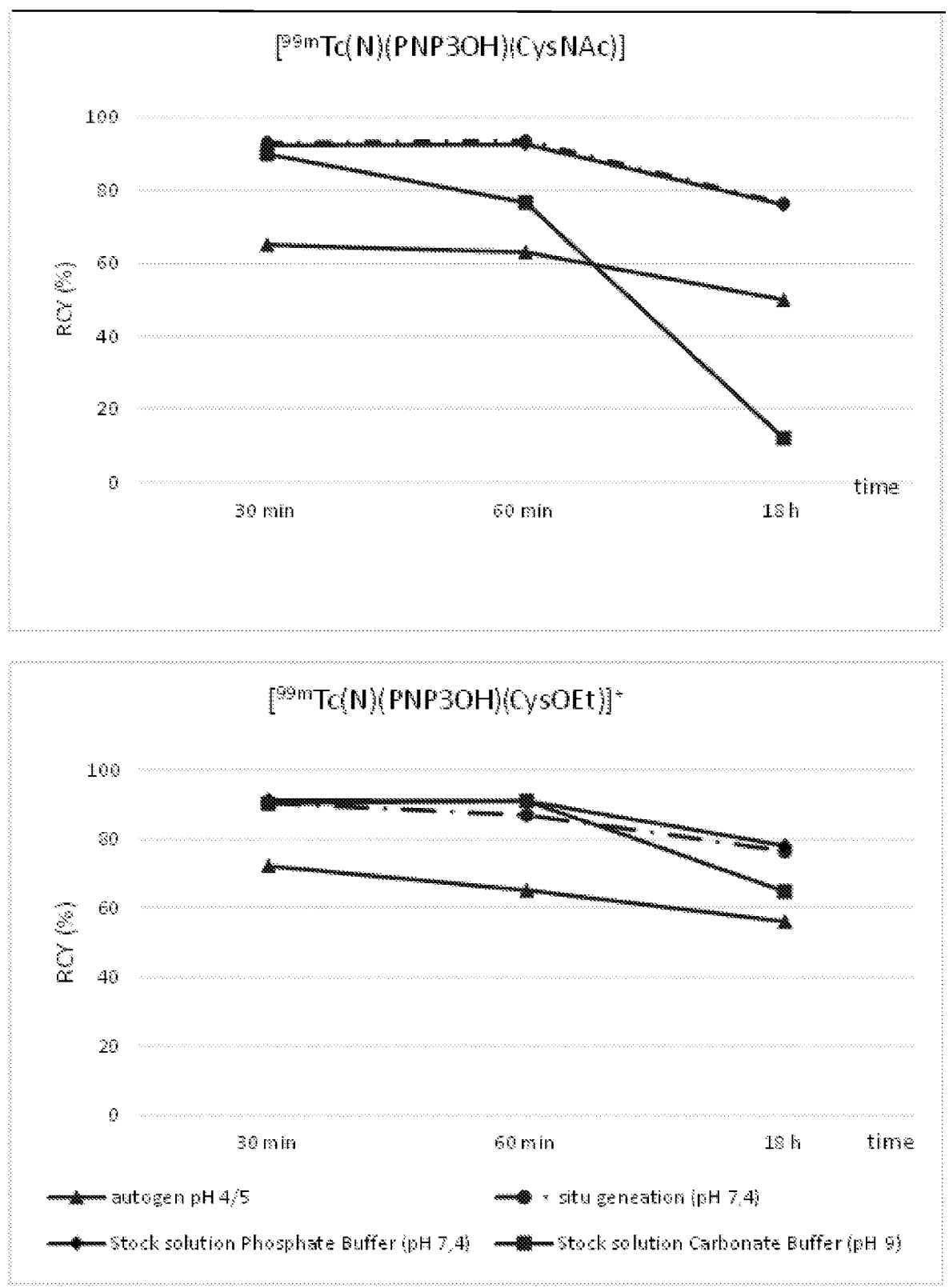
FIG. 5 is the variation over the time of RCY (%) of complex 1 and complex 2 templates as function of the pH.
Figure 6A:
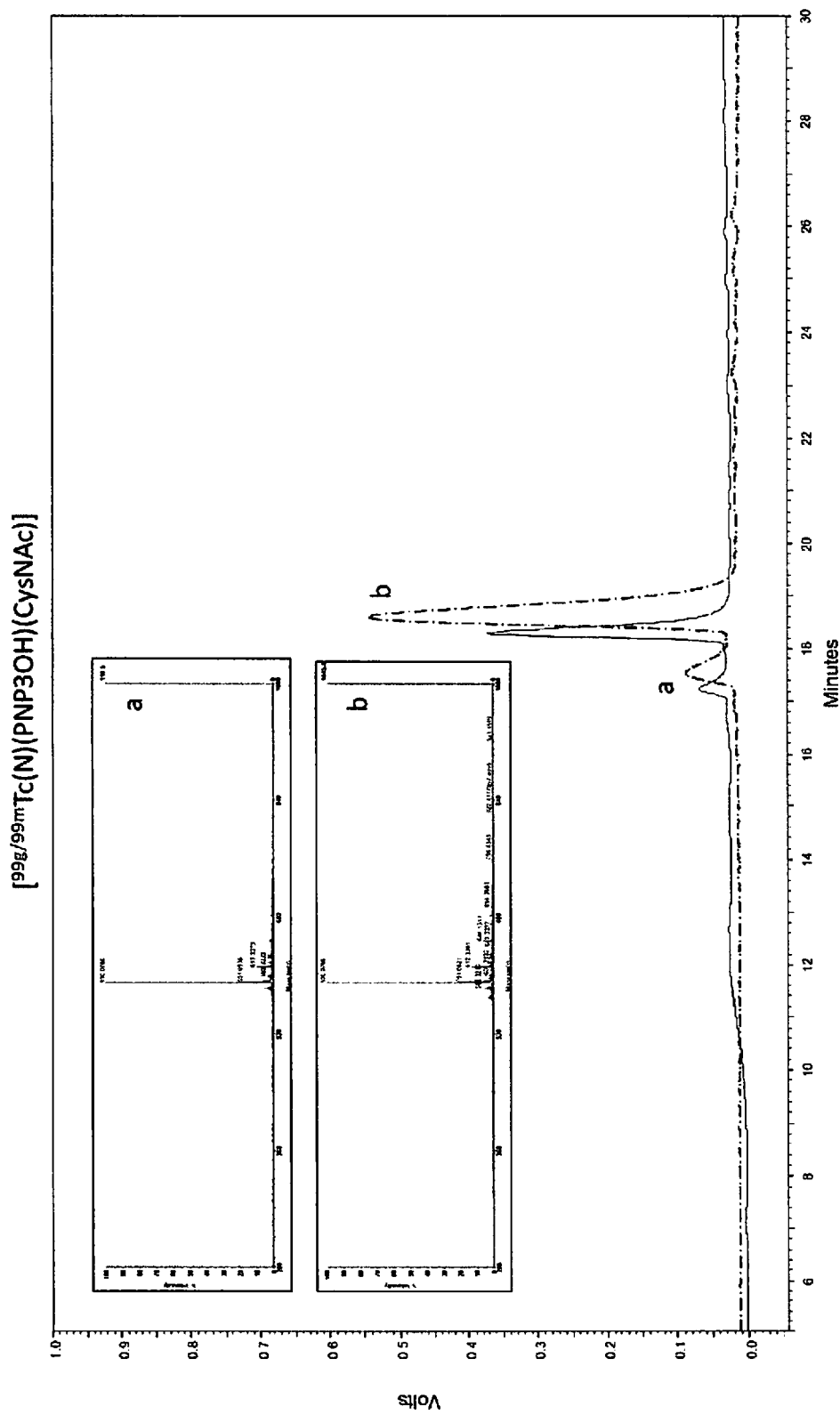
FIG. 6A represents HPLC profiles (UV, Radio) of the template [$^{99g/99m}$Tc(N)(PNP3OH)(CysNAc)] produced in carrier added conditions along with the corresponding ESI-MS spectra.
Figure 6B:
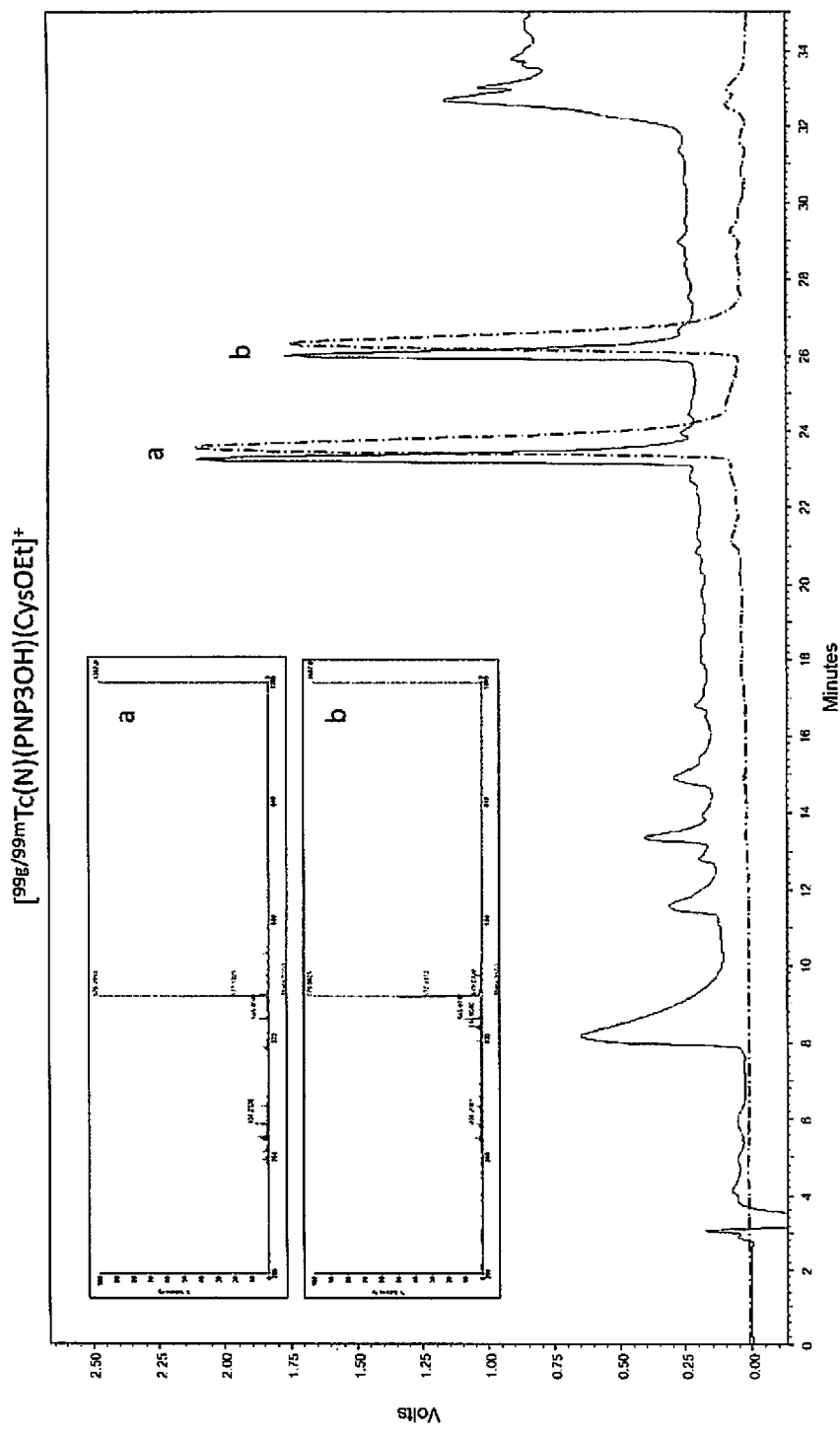
FIG. 6B represents HPLC profiles (UV, Radio) of the template [$^{99g/99m}$Tc(N)(PNP3OH)(CysOEt)]$^+$ produced in carrier added conditions along with the corresponding ESI-MS spectra.

Some of the RP-HPLC profiles of the final complexes collected at 30 min of incubation at RT are shown in FIG. 4.

When the reaction was conducted at 80° C., a significant reduction of the RCY of [$^{99m}$Tc(N)(PNP3OH)(CysGly)]$^+$ was observed (23%).

Method 2 (One-Step) in PB.

To a vial containing SDH (2.5 mg) and SnCl$_2$ (0.100 mg suspended in 0.100 ml of saline) was added Na[$^{99m}$TcO$_4$] (0.500 ml; 185 MBq). The vial was vortexed for 10 seconds. Rapidly PNP3OH.HCl (1 mg in 0.200 ml of PB 0.2 M pH 7.4), ZY (0.150-0.005 mg in 0.2 ml of H$_2$O) were simultaneously added. The reaction mixture was left standing at RT for 60 min. The pH of the reaction mixture, measured at the end of the reaction, was 7.2 and the volume was 1 ml.

When the reaction was conducted at 80° C., a significant reduction of the RCY of [$^{99m}$Tc(N)(PNP3OH)(CysGly)]$^+$ was observed (21.23%).

Method 2 (One-Step) in PBS.

To a vial containing SDH (2.5 mg) and SnCl$_2$ (0.100 mg suspended in 0.100 ml of saline) was added Na[$^{99m}$TcO$_4$] (0.300 ml; 185 MBq). The vial was vortexed for 10 seconds. Rapidly PNP3OH.HCl (1 mg in 1.00 ml of PBS 1×) and ZY (0.150-0.005 mg in 0.1 ml) were simultaneously added. The reaction mixture was left standing at RT for 60 min. The pH of the reaction mixture, measured at the end of the reaction, was 7 and the volume was 1.5 ml.

When the reaction was conducted at 80° C., a significant reduction of the RCY of [$^{99m}$Tc(N)(PNP3OH)(CysGly)]$^+$ was observed (73.85%).

RCYs obtained by the different methods and determined by HPLC chromatography are reported in Table 1.

The variation of (%)RCY of complex 1 and complex 2 over the time (30 min vs 18 h), at different conditions, is shown in FIG. 5. In these preparations, the phosphonium salt PNP3OH.HCl is employed at autogenic pH, or converted in situ into the corresponding free PNP3OH by the addition of phosphate buffer 0.2 M pH 7.4. Alternatively, free PNP3OH was directly used. This latter was obtained dissolving PNP3OH.HCl in phosphate buffer 0.2 M pH 7.4 or in carbonate buffer 0.5 M pH 9, before the use.

Carrier Added Preparation of ($^{99m/99g}$Tc(N)(PNP3OOH)(CysNAc)] and [$^{99m/99g}$Tc(N)(PNP3OH)(CysOEt)]$^+$ for MS Characterization.

To confirm the chemical identity of the radiolabeled compounds, carrier-added syntheses were performed using both long-lived $^{99g}$Tc and short-lived $^{99m}$Tc to prepare [$^{99g/99m}$Tc(N)(PNP3OH)(YZ)]$^{°+}$ templates.

Briefly, Na[$^{99m}$TcO$_4$] (0.400 ml, 50.0 MBq) was added to a vial containing SDH (15.0 mg), SnCl$_2$ (2 mg suspended in 0.100 ml of saline) and NH$_4$[$^{99g}$TcO$_4$] (0.050 mg in 0.100 ml of saline). The vial was kept at room temperature for 30 min giving a mixture of $^{99m}$Tc-nitrido precursors [$^{99m}$Tc≡N]$_{int}^{2+}$. Then a stock solution of PNP3OH (1 mg of PNP3OH.HCl dissolved in 0.200 ml of PB 0.2 M pH 7.4 and the selected cysteine derivative ligand (3 mg dissolved in 0.200 ml of water) were added, and the reaction mixture was left at room temperature for 30 min. The pH of the reaction mixture, measured at the end of the reaction, was 7.

The carrier-added preparations were analyzed by HPLC with dual detector. Chromatographic profiles of both preparations display two superimposable UV and radiometric peaks, which were isolated and analyzed by ESI(+)-MS after complete $^{99m}$Tc-decay. The mass spectra show the expected signals in FIGS. 6A and 6B.

[$^{99g}$Tc(N)(PNP3OH)(CysNAc)] isomer a m/z 590 ([M+H]$^+$, 100%); isomer b m/z 590 (M+H$^+$, 100%);

[99gTc(N)(PNP3OH)(CysOEt)]+ isomer a m/z 576 (M+, 100%); isomer b m/z 576 (M+, 100%).

Example 8: Radiosynthesis of Complex 4, [$^{99m}$Tc(N)(PNP43)(CysGly)]$^+$

The complex was prepared according to the two-step and one-step procedure described in Method 1 and 2 respectively, by using a CysGly amount of 0.010 mg as determined by radiolabeling efficiency studies. The reactions were carried out at RT.

Method 1 (Two-Step) in PB.

Na[$^{99m}$TcO$_4$] (0.500 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP43 (0.25 mg dissolved in 0.1 ml of EtOH), CysGly (0.010 mg in 0.1 ml of H$_2$O) and PB (0.200 ml, 0.2 M pH 7.4) were added, and the reaction mixture was left standing at RT for 60 min. The pH measured at the end of the reaction, was 7 and the volume was 1 ml.

Method 2 (One-Step) in PB.

To a vial containing SDH (2.5 mg) and SnCl$_2$ (0.100 mg suspended in 0.10 ml of saline) was added Na[$^{99m}$TcO$_4$] (0.500 ml; 185 MBq). The vial was vortexed for 10 seconds. Rapidly PNP43 (0.25 mg dissolved in 0.1 ml of EtOH), CysGly (0.010 mg in 0.1 ml of H$_2$O) and PB (0.200 ml, 0.2 M pH 7.4) were added. The reaction mixture was left standing at RT for 60 min. The pH measured at the end of the reaction, was 7.2 and the volume was 1 ml.

RCYs as determined by HPLC chromatography at room temperature are reported in Table 1.

Comparative Example 9: Radiosynthesis of Comparative A, [$^{99m}$Tc(N)(PNP3)(CysGly)]

For comparative purposes, as further example, the small peptide CysGly was labeled by using [$^{99m}$Tc(N)(PNP3)]-scaffold.

The complex was prepared according to the two-step and one-step procedure described in Method 1 and 2 respectively, by using a CysGly amount of 0.010 mg as determined by radiolabeling efficiency studies. The reactions were carried out at RT.

Method 1 (Two-Step) in PB.

Na[$^{99m}$TcO$_4$] (0.500 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3 (1 mg dissolved in 0.1 ml of EtOH), CysGly (0.010 mg in 0.1 ml of H$_2$O) and PB (0.200 ml, 0.2 M pH 7.4) were added, and the reaction mixture was left standing at RT for 60 min. The pH measured at the end of the reaction, was 7 and the volume was 1 ml.

Method 2 (One-Step) in PB.

To a vial containing SDH (2.5 mg) and SnCl$_2$ (0.100 mg suspended in 0.10 ml of saline) was added Na[$^{99m}$TcO$_4$] (0.500 ml; 185 MBq). The vial was vortexed for 10 seconds. Rapidly PNP3 (1 mg dissolved in 0.1 ml of EtOH), CysGly (0.010 mg in 0.1 ml of H$_2$O) and PB (0.200 ml, 0.2 M pH 7.4) were added. The reaction mixture was left standing at RT for 60 min. The pH measured at the end of the reaction, was 7.2 and the volume was 1 ml.

RCYs as determined by HPLC chromatography at room temperature are reported in Table 1.

Example 10: Radiosynthesis of Complex 5, [$^{99m}$Tc(N)(PNP3OH)(DT-OEt)]

Method 1 (Two-Step) Hydroalcoholic Solution in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3OH.HCl (1 mg dissolved in 0.200 ml of PB 0.2 M pH 7.4) and DT-OEt (1.5 mg in 0.3 ml di EtOH) were added and the reaction mixture was left standing at RT for 60 min. The pH of the reaction mixture, measured at the end of the reaction, was 7 and the volume was 1 ml. RCYs as determined by HPLC chromatography are reported in Table 2.

Method 2 (One-Step) Hydroalcoholic Solution in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP3OH.HCl (1 mg in 0.200 ml of PB 0.2 M pH 7.4) and DT-OEt (1.5-0.0075 mg in 0.3 ml di EtOH). The reaction mixture was left standing at RT for 60 min. The pH of the reaction mixture, measured at the end of the reaction, was 7 and the volume was 1 ml. RCYs as determined by HPLC chromatography are reported in Table 2.

Method 2 (One-Step) Hydroalcoholic Solution in PBS.

To a vial containing SDH (2.5 mg) and SnCl$_2$ (0.10 mg suspended in 0.10 ml of saline) was added Na[$^{99m}$TcO$_4$] (0.100 ml; 185 MBq), rapidly followed by PNP3OH.HCl (1 mg in 1.00 ml of PBS 1x) and DT-OEt (0.0075 mg in 0.3 ml di EtOH). The reaction mixture was left standing at RT for 60 min. The pH of the reaction mixture, measured at the end of the reaction, was 7 and the volume was 1.5 ml.

RCYs as determined by HPLC chromatography are reported in Table 2.

Example 11: Radiosynthesis of Complex 6, [$^{99m}$Tc(N)(PNP43)(DT-OEt)]

Method 1 (Two-Step) in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP (PNP43, 0.25 mg dissolved in 0.1 ml of EtOH), DT-OEt (0.0075 mg in 0.2 ml di EtOH) and PB (0.200 ml, 0.2 M pH 7.4) were added, and the reaction mixture was left standing at RT for 60 min. The pH measured at the end of the reaction, was 7 and the volume was 1 ml.

Method 2 (One-Step) in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP43 (0.25 mg dissolved in 0.1 ml of EtOH), DT-OEt (0.0075 mg in 0.2 ml di EtOH) and PB (0.200 ml, 0.2 M pH 7.4). The reaction mixture was left standing at RT for 60 min. The pH measured at the end of the reaction, was 7 and the volume was 1 ml.

RCYs as determined by HPLC chromatography at room temperature are reported in Table 2.

Comparative Example 12: Radiosynthesis of Comparative B, [$^{99m}$Tc(N)(PNP3)(DT-OEt)]

For comparative purposes, the complex was prepared according to the two-step and one-step procedure described in Method 1 and 2 respectively, by using a DT-OEt amount of 0.0075 mg. The reactions were carried out at RT.

Method 1 (Two-Step) in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP (1 mg dissolved in 0.1 ml of EtOH), DT-OEt (0.0075 mg in 0.2 ml di EtOH) and PB (0.200 ml, 0.2 M pH 7.4) were added, and the reaction mixture was left standing at RT for 60 min. The pH measured at the end of the reaction, was 7 and the volume was 1 ml.

Method 2 (One-Step) in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP3 (1 mg dissolved in 0.1 ml of EtOH), DT-OEt (0.0075 mg in 0.2 ml of EtOH) and PB (0.200 ml, 0.2 M pH 7.4). The reaction mixture was left standing at RT for 60 min. The pH measured at the end of the reaction, was 7 and the volume was 1 ml.

RCYs as determined by HPLC chromatography at room temperature are reported in Table 2.

Example 13: Radiosynthesis of Complex 7, [$^{99m}$Tc(N)(PNP3OH)(DT-OH)]

Method 1 (Two-Step) Hydroalcoholic Solution in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3OH.HCl (1 mg dissolved in 0.200 ml of PB 0.2 M pH 7.4) and DT-OH (0.00078 mg in 0.3 ml di EtOH) were added and the reaction mixture was left standing at RT for 60 min, and HPLC-analyzed at 30 and 60 min. The pH of the reaction mixture, measured at the end of the reaction, was 7 and the volume was 1 ml. RCY as determined by HPLC chromatography is reported in Table 3.

Method 2 (One-Step) Hydroalcoholic Solution in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP3OH.HCl (1 mg in 0.200 ml of PB 0.2 M pH 7.4) and DT-OH (0.0078-0.000156 mg in 0.3 ml di EtOH). The reaction mixture was left standing at RT for 60 min and HPLC-analyzed at 30 and 60 min. The pH of the reaction mixture, measured at the end of the reaction, was 7 and the volume was 1 ml. RCY as determined by HPLC chromatography is reported in Table 3.

Method 2 (One-Step) Hydroalcoholic Solution in PBS.

To a vial containing SDH (2.5 mg) and SnCl$_2$ (0.10 mg suspended in 0.10 ml of saline) was added Na[$^{99m}$TcO$_4$] (0.100 ml; 185 MBq), rapidly followed by PNP3OH.HCl (1 mg in 1.00 ml of PBS 1×) and DT-OH (0.00078 mg in 0.3 ml di EtOH). The reaction mixture was left standing at RT for 60 min and HPLC-analyzed at 30 and 60 min. The pH of the reaction mixture, measured at the end of the reaction, was 7 and the volume was 1.5 ml. RCY as determined by HPLC chromatography is reported in Table 3.

Example 14: Radiosynthesis of Complex 8, [$^{99m}$Tc(N)(PNP43)(DT-OH)]

Method 1 (Two-Step) Hydroalcoholic Solution in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP43 (0.25 mg dissolved in 0.1 ml of EtOH), DT-OH (0.00078 mg in 0.2 ml di EtOH) and PB (0.200 ml, 0.2 M pH 7.4) were added, and the reaction mixture was left standing at RT for 60 min (and HPLC-checked at 30 and 60 min). The pH measured at the end of the reaction, was 7 and the volume was 1 ml. RCY as determined by HPLC chromatography at room temperature were reported in Table 3.

Method 2 (One-Step) Hydroalcoholic Solution in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP43 (0.25 mg dissolved in 0.1 ml of EtOH), DT-OH (0.00078 mg in 0.2 ml di EtOH) and PB (0.200 ml, 0.2 M pH 7.4). The reaction mixture was left standing at RT for 60 min (and HPLC-checked at 30 and 60 min). The pH measured at the end of the reaction, was 7 and the volume was 1 ml.

RCYs as determined by HPLC chromatography at room temperature are reported in Table 3.

Comparative Example 15: Radiosynthesis of Comparative C, [$^{99m}$Tc(N)(PNP3)(DT-OH)]

For comparative purposes, the complex was prepared according to the two-step and one-step procedure described in Method 1 and 2 respectively, by using a DT-OH amount of 0.00078 mg. The reactions were carried out at RT.

Method 1 (Two-Step) Hydroalcoholic Solution in PB.

Na[$^{99m}$TcO$_4$] (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3 (1 mg dissolved in 0.1 ml of EtOH), DT-OH (0.00078 mg in 0.2 ml di EtOH) and PB (0.200 ml, 0.2 M pH 7.4) were added, and the reaction mixture was left standing at RT for 60 min (and HPLC-checked at 30 and 60 min). The pH measured at the end of the reaction, was 7 and the volume was 1 ml. RCY as determined by HPLC chromatography at room temperature are reported in Table 3.

Method 2 (One-Step) Hydroalcoholic Solution in PB.

To a vial containing SDH (2.5 mg) and SnCl$_2$ (0.10 mg suspended in 0.10 ml of saline) was added Na[$^{99m}$TcO$_4$] (0.400 ml; 185 MBq), rapidly followed by PNP3 (1 mg dissolved in 0.1 ml of EtOH), DT-OH (0.00078 mg in 0.2 ml di EtOH) and PB (0.200 ml, 0.2 M pH 7.4). The reaction mixture was left standing at RT for 60 min (and HPLC-checked at 30 and 60 min). The pH measured at the end of the reaction, was 7 and the volume was 1 ml.

RCYs as determined by HPLC chromatography at room temperature are reported in Table 3.

Example 16: Radiolabeling Efficiency of DT-OH Ligand

The radiolabeling efficiency of DT-OH is determined following the standardized labeling condition reported in Method 2 (one-step). The amount of PNP3OH.HCl was fixed at 1 mg (2×10$^{-3}$ M), while the amount of DT-OH was progressively decreased in the range 0.78 mg (6.29×10$^{-3}$ M)-0.000078 mg (6.29×10$^{-7}$ M). The mixture was incubated at RT for 30 min. The final pH was 7 and the volume was 1 ml. The RCY was determined by HPLC. Data are summarized in Table 9.

Labeling of Medium Size Molecule

Example 17: Radiosynthesis of Complex 9, [$^{99m}$Tc(N)(PNP3OH)(Cys-cRGDfK)]$^+$ Method 1 (Two-Step) in PB.

Na[$^{99m}$TcO$_4$] (1.0 ml, 50.0 MBq-2.2 GBq) was added to a vial containing SDH (5.0 mg) and SnCl$_2$ (0.1 mg of suspended in 0.1 ml of saline). The vial was kept at room temperature for 15 minutes giving a mixture of $^{99m}$Tc-nitrido precursors, [Tc≡N]$_{int}^{2+}$. PNP3OH.HCl (1.0 mg in 0.2 ml of PB 0.2 M, pH 7.4) and Cys-cRGDfK, (0.050 mg in 0.200 ml of water) were simultaneously added to the reaction vial. The reaction mixture was incubated at room temperature for 30 min. The pH of the reaction mixture, measured at the end of the reaction, was 7.4.

RCYs as determined by HPLC chromatography were summarized in Table 4. HPLC profiles of the final complex at 30 min of incubation at RT are shown in FIG. 4.

Example 18: Radiosynthesis of Complex 10, [$^{99m}$Tc(N)(PNP43)(Cys-cRGDfK)]$^+$ Method 1 (Two-Step).

Na[$^{99m}$TcO$_4$] (0.95 ml, 50.0 MBq-2.2 GBq) was added to a vial containing SDH (5.0 mg) and SnCl$_2$ (0.1 mg of suspended in 0.1 ml of saline). The vial was kept at room temperature for 15 minutes giving a mixture of $^{99m}$Tc-nitrido precursors, [Tc≡N]$_{int}^{2+}$. PNP43 (0.25 mg/0.5 ml γ-cyclodextrin 4 mg/ml) and Cys-cRGDfK, (0.050 mg in 0.050 ml of water) were simultaneously added to the reaction vial. The reaction mixture was incubated at room temperature for 30 min. The pH of the reaction mixture, measured at the end of the reaction, was 7.4.

RCYs as determined by HPLC chromatography are summarized in Table 4.

Comparative Example 19: Radiosynthesis of Comparative D, [$^{99m}$Tc(N)(PNP3)(Cys-cRGDfK)]$^+$ Method 1 (Two-Step).

Na[$^{99m}$TcO$_4$] (0.95 ml, 50.0 MBq-2.2 GBq) was added to a vial containing SDH (5.0 mg) and SnCl$_2$ (0.1 mg of suspended in 0.1 ml of saline). The vial was kept at room temperature for 15 minutes giving a mixture of $^{99m}$Tc-nitrido precursors, [Tc≡N]$_{int}^{2+}$. PNP3 (1 mg/0.5 ml γ-cyclodextrin 4 mg/ml) and Cys-cRGDfK, (0.050 mg in 0.050 ml of water) were simultaneously added to the reaction vial. The reaction mixture was incubated at room temperature for 30 min. The pH of the reaction mixture, measured at the end of the reaction, was 7.4.

RCYs as determined by HPLC chromatography are summarized in Table 4.

Example 20: Radiosynthesis of Complex 11, [$^{99m}$Tc(N)(PNP3OH)(Biot-Abu-Cys)]

Method 1 (Two-Step).

Na[$^{99m}$TcO$_4$] (1.0 ml, 50.0 MBq-2.2 GBq) was added to a vial containing SDH (5.0 mg) and SnCl$_2$ (0.1 mg of suspended in 0.1 ml of saline). The vial was kept at room temperature for 30 minutes giving a mixture of $^{99m}$Tc-nitrido precursors, [Tc≡N]$_{int}^{2+}$. PNP3OH.HCl (2.0-0.625 mg in 0.2 ml of water), sodium phosphate buffer (0.2 ml, 0.2 M, pH 7.4) and Biot-Abu-Cys (0.200 mg in 0.2 ml of water) were simultaneously added to the reaction vial. The reaction mixture was incubated at room temperature for 30 min. The pH of the reaction mixture, measured at the end of the reaction, was 7.4.

RCYs as determined by HPLC chromatography are summarized in Table 5.

Comparative Example 21: Radiosynthesis of Comparative E, [$^{99m}$Tc(N)(PNP3)(Biot-Abu-Cys)]

Method 1 (Two-Step).

Na[$^{99m}$TcO$_4$] (1.0 ml, 50.0 MBq-2.2 GBq) was added to a vial containing SDH (5.0 mg) and SnCl$_2$ (0.1 mg of suspended in 0.1 ml of saline). The vial was kept at room temperature for 30 minutes giving a mixture of $^{99m}$Tc-nitrido precursors, [Tc≡N]$_{int}^{2+}$. PNP3 (1 mg in 0.1 ml of EtOH), sodium phosphate buffer (0.2 ml, 0.2 M, pH 7.4) and Biot-Abu-Cys (0.200 mg in 0.3 ml of water) were simultaneously added to the reaction vial. The reaction mixture was incubated at room temperature for 30 min. The pH of the reaction mixture, measured at the end of the reaction, was 7.4.

RCYs as determined by HPLC chromatography are summarized in Table 5.

Example 22: Radiolabeling Efficiency as Function of Cys-Ligand Amount

The radiolabeling efficiency of the selected Cys-ligand was determined following the standardized labeling condition reported in Method 1. The amount of PNP3OH.HCl was fixed at 1 mg (3.17 10$^{-3}$ mmol), while the concentration of the Cys-ligand was progressively decreased in the range: 3 mg (18,4×10$^{-3}$ mmol)-5 μg (3.06×10$^{-5}$ mmol) for CysNAc; 3 mg (20.10×10$^{-3}$ mmol)-5 μg (3.35×10$^{-5}$ mmol) for CysO-Et.HCl; 0.250 mg (5.77×10$^{-4}$ mmol)-50 μg (1.15×10$^{-4}$ mmol) for Biot-Abu-Cys; 0.200 mg (2.82×10$^{-4}$ mmol)-5 μg (7.07×10$^{-6}$ mmol) for Cys-cRGDfK. The mixture was incubated at room temperature for 30 min. The RCY was determined by HPLC.

Figure 7:
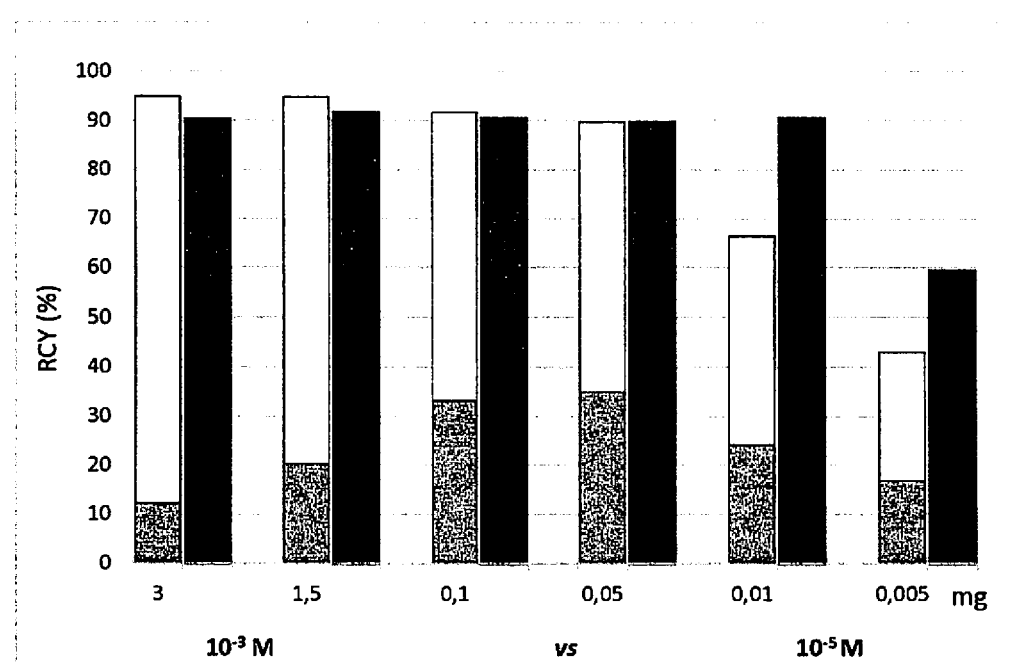
FIG. 7 is the dependence of RCY (%) of complex 1 and complex 2 templates as function of the milligrams amount of the cysteine derivative co-ligands. For each compound the distribution of the two isomer is also shown. ☐ complex 1a, ▨ complex 1b; ■ complex 2a, ■ complex 2b.
Figure 8:
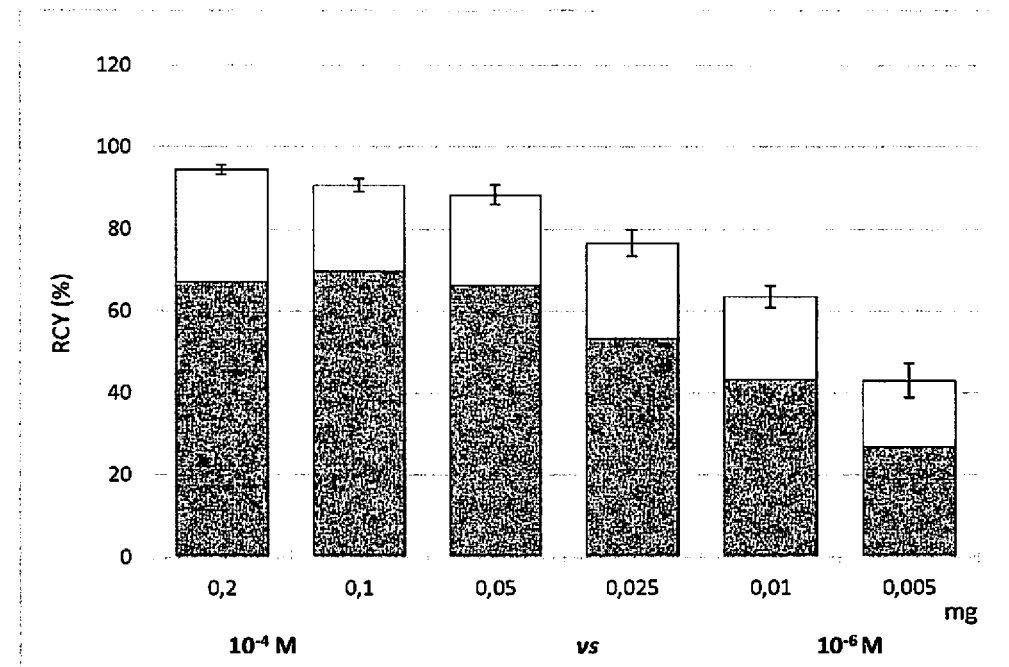
FIG. 8 is the dependence of RCY (%) of complex 9 along with distribution of the two isomers as function of the milligrams amounts of Cys-cRGDfK peptide. ☐ complex 9a, ■ complex 9b.

The dependence of (%)RCY of formation of the complexes along with the distribution of each isomeric form on the concentration of the co-ligands is illustrated in FIG. 7 for the complex 1 and complex 2 and in FIG. 8 for complex 9.

The quantitative formation of complex 2 was threaten by the formation of byproducts generated by the hydrolysis of the ester group [—(CO)OEt] of the co-ligand. Notable, for complex 1 and complex 2, the variation of the isomeric distribution was found to be a function of the co-ligand amounts.

Example 23: Radiosynthesis of Complex 12, [$^{99m}$Tc(N)(PNP3OH)(Glu-Urea-Lys-2-naphthyl-L-Ala-Amc-Cys)]$^+$ Method 1 (Two-Step) in PB.

Na[$^{99m}$TcO$_4$] (0.500 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}$Tc-nitrido precursors [$^{99m}$Tc≡N]$_{int}^{2+}$. Then PNP3OH.HCl (0.5 mg dissolved in 0.200 ml of PB 0.2 M pH 7.4) and and Glu-Urea-Lys-2-naphthyl-L-Ala-Amc-Cys (0.043 mg/0.043 μl DMSO in 0.157 ml of H$_2$O) were added and the reaction mixture was left standing at RT for 60 min. The pH of the reaction mixture, measured at the end of the reaction, was 7.2 and the volume was 1 ml.

RCYs determined by HPLC and TLC chromatography are reported in Table 7.

Method 2 (One-Step) in PB.

To a vial containing SDH (5 mg) and SnCl$_2$ (0.100 mg suspended in 0.100 ml of saline) was added Na[$^{99m}$TcO$_4$] (0.500 ml; 185 MBq). The vial was vortexed for 10 seconds. Rapidly PNP3OH.HCl (0.5 mg in 0.200 ml of PB 0.2 M pH 7.4), and Glu-Urea-Lys-2-naphthyl-L-Ala-Amc-Cys (0.043 mg/0.043 μl DMSO in 0.157 ml of H$_2$O) were simultaneously added. The reaction mixture was left standing at RT for 60 min. The pH of the reaction mixture, measured at the end of the reaction, was 7.2 and the volume was 1 ml.

RCYs determined by HPLC chromatography are reported in Table 7.

Carrier Added Preparation of [$^{99m/99g}$Tc(N)(PNP3OH)(Glu-Urea-Lys-2-Naphthyl-L-Ala-Amc-Cys)]$^+$ and for MS Characterization.

To confirm the chemical identity of the radiolabeled compound, carrier-added syntheses were performed using both long-lived $^{99g}$Tc and short-lived $^{99m}$Tc to prepare [$^{99m/99g}$Tc(N)(PNP3OH)(Glu-Urea-Lys-2-naphthyl-L-Ala-Amc-Cys)]$^+$ compound. To a vial containing SDH (15 mg), SnCl$_2$ (2 mg suspended in 0.100 ml of saline) an aqueous solution containing Na[$^{99m}$TcO$_4$] (0.400 ml, 185 MBq) and NH$_4$[$^{99g}$TcO$_4$] (0.100 mg/0.100 ml) was added. The vial was kept at room temperature for 30 min giving a mixture of $^{99m}$Tc-nitrido precursors [$^{99m/99g}$Tc≡N]$_{int}^{2+}$. Then PNP3OH.HCl (0.5 mg dissolved in 0.200 ml of PB 0.2 M pH 7.4) and Glu-Urea-Lys-2-naphthyl-L-Ala-Amc-Cys (0.5 mg/0.050 μl DMSO in 0.15 ml of H$_2$O) were added and the reaction mixture was left standing at RT for 60 min. The pH of the reaction mixture, measured at the end of the reaction, was 7.2 and the volume was 1 ml.

Purification.

The reaction mixture was diluted 1:9 with milliQ water, then loaded into a Sep Pak C18 cartridge (pre-conditioned with 5 mL EtOH and 5 ml water). The product on the cartridge was washed with 20 ml saline and 3 ml EtOH 10%. The radiocomplex was fractional eluted with 2 ml EtOH/Saline mixture 40/60 (fraction #1: 4 gtt; fraction #2: 25-30 gtt; fraction #3: rest); most of the compound was in fraction #2). The purified product, after the complete 99mTc-decay, was analyzed by LC-MS (Surveyor Plus combined LCQ Fleet Thermo-Scientific ion trap mass spectrometer equipped with a heated electrospray ionization ion source, operating in positive ion mode).

ESI-MS $[^{99g}Tc(N)(PNP3OH)(Glu-Urea-Lys-2-naphthyl-L-Ala-Amc-Cys)]^+$ a MW calculated for $C_{47}H_{76}N_8O_{15}P_2S_2Tc=1186.08$ Found (m/z=593 $[M+H]^{2+}$ (abundance 100%); m/z=1185 $[M]^+$ (abundance 15%).

ESI-MS $[^{99g}Tc(N)(PNP3OH)(Glu-Urea-Lys-2-naphthyl-L-Ala-Amc-Cys)]^+$ b MW calculated for $C_{47}H_{76}N_8O_{15}P_2S_2Tc=1186.08$ Found (m/z=593 $[M+H]^{2+}$ (abundance 30%); m/z=1185 $[M]^+$ (abundance 25%).

Example 24: Radiosynthesis of Complex 13, $[^{99m}Tc(N)(PNP43)(Glu-Urea-Lys-2-Naphthyl-L-Ala-Amc-Cys)]^+$ Method 1 (Two-Step) in PB.

Na$[^{99m}TcO_4]$ (0.400 ml, 185 MBq) was added to a vial containing SDH (2.5 mg), SnCl$_2$ (0.100 mg suspended in 0.100 ml of saline). The vial was kept at room temperature for 15 min giving a mixture of $^{99m}Tc$-nitrido precursors $[^{99m}Tc\equiv N]_{int}^{2+}$. Then PNP43 (0.25 mg dissolved in 0.100 ml of EtOH), Glu-Urea-Lys-2-naphthyl-L-Ala-Amc-Cys (0.043 mg/0.043 μl DMSO in 0.157 ml of H$_2$O) and 0.2 ml of PB (0.2 M, pH 7.4) were added and the reaction mixture was left standing at RT for 60 min. The pH of the reaction mixture, measured at the end of the reaction, was 7.2 and the volume was 1 ml.

RCYs determined by HPLC chromatography are reported in Table 7.

When the reaction was conducted at 80° C. the RCP was 82.06±2.65%.

Labeling of Large Molecules (>15000 Da)

Example 25: Radiosynthesis of $[^{99m}Tc(N)(PNP3OH)(Cys-Gly-Lys-Gly-ApoMb)]^+$ ("Cys-Gly-Lys-Gly" Disclosed as SEQ ID NO: 1)

Method 1 (two-step) in PB. To 40 μl (111 MBq) of $[^{99m}Tc\equiv N]_{m/x}^{2+}$ intermediate prepared as above, PNP3OH—HCl (5 μg in 5 μl of PB 0.2 M, pH 7.4), PB (45 0.2 ml, 0.2 M, pH 7.4) and Cys-Gly-Lys-Gly-ApoMb (SEQ ID NO: 1) (80 μg in 10 μl of TFA 0.01%) were simultaneously added. The reaction mixture was incubated at room temperature for 30 min.

RCYs are summarized in Table 6. Characterization was performed by TLC and HPLC.

Figure 13:
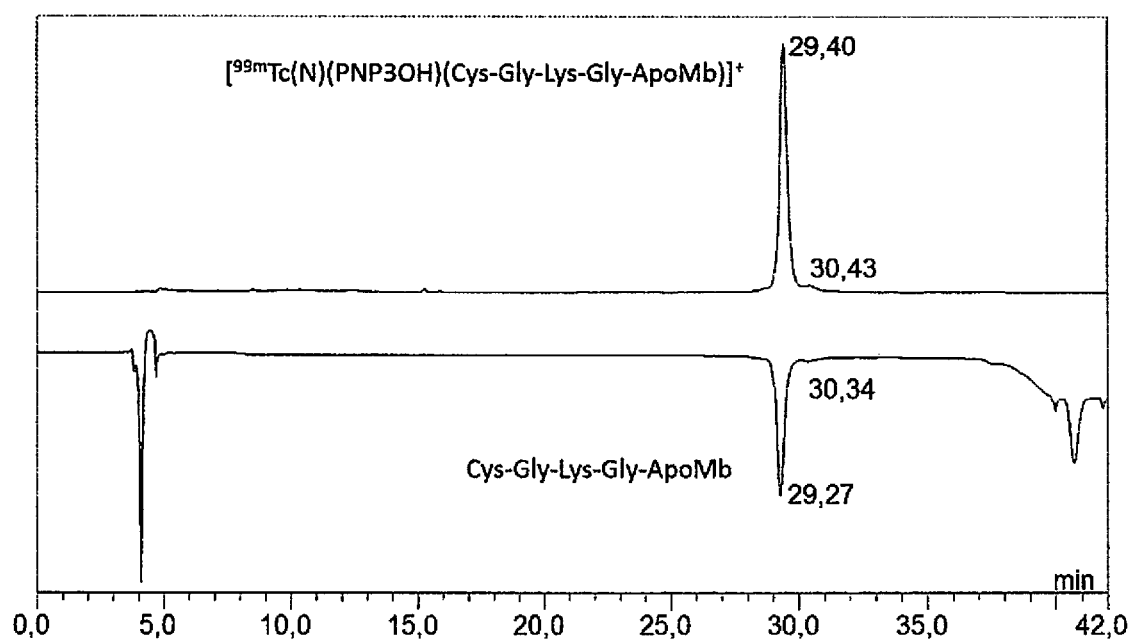
FIG. 13 is the HPLC profile of [$^{99m}$Tc(N)(PNP3OH)(Cys-Gly-Lys-Gly-ApoMb)]$^+$ ("Cys-Gly-Lys-Gly" disclosed as SEQ ID NO: 1); up radio trace, down UV trace.
Figure 14:
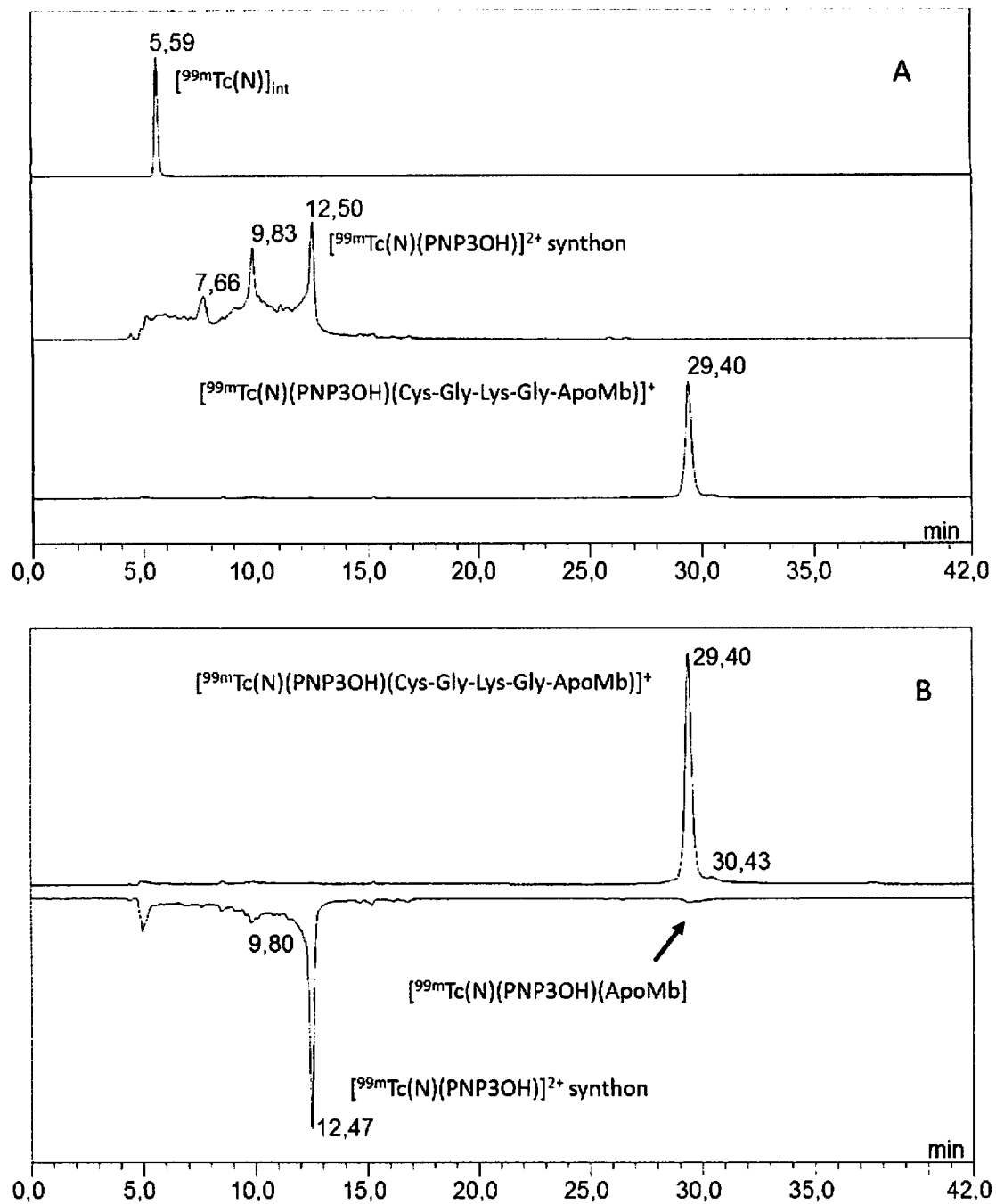
FIG. 14 represents the radio-HPLC comparison of $^{99m}$Tc (N)-intermediates, [$^{99m}$Tc(N)(PNP3OH)]$^{2+}$ building block, [$^{99m}$Tc(N)(PNP3OH)(Cys-Gly-Lys-Gly-ApoMb)]$^+$ ("Cys-Gly-Lys-Gly" disclosed as SEQ ID NO: 1) (A) and the radio-HPLC comparison of [$^{99m}$Tc(N)(PNP3OH)(Cys-Gly-Lys-Gly-ApoMb)]$^+$ ("Cys-Gly-Lys-Gly" disclosed as SEQ ID NO: 1), [$^{99m}$Tc(N)(PNP3OH)(ApoMb)]$^+$, comparative F (B).
Figure 15:
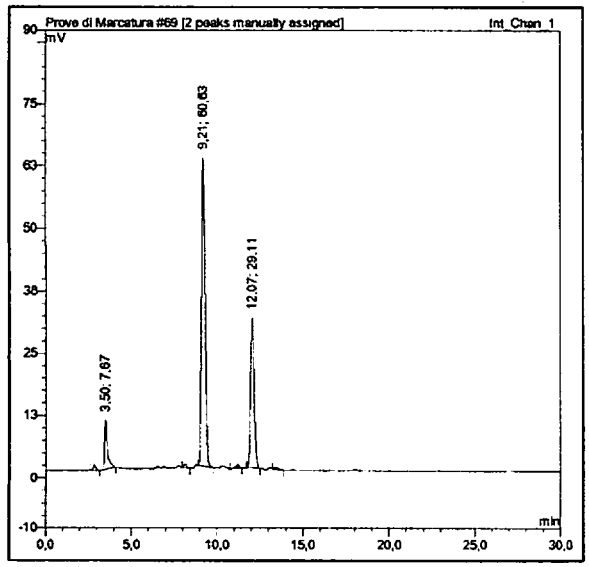
FIG. 15 represents the radio-HPLC profiles of [$^{99m}$Tc(N) (PNP3OH)(Glu-Urea-Lys-2-naphthyl-L-Ala-Amc-Cys)]$^+$ collected at 30 min of incubation at RT. HPLC analysis was performed with a Reverse Phase Symmetry300 RP-C18 precolumn (5 µm, 4.6×45 mm) and Symmetry300 RP-C18 column (5 µm 4.6×250 mm). Flow rate: 1 mL/min. UV detector: $\lambda$=230 nm. Solvents: A=H$_2$O TFA 0.1%; B=CH$_3$CN TFA 0.1%. Gradient: 0 min, % B=25; 1 min, % B=25; 17 min, % B=32; 23 min, % B=32; 24 min, % B=90; 28 min, % B=90; 29 min, % B=25; 30 min, % B=25. RP-HPLC profile of the reaction mixtures indicates the formation, in high yield, of the complexes as a mixture of two syn and anti isomers in different ratios.
Figure 16:
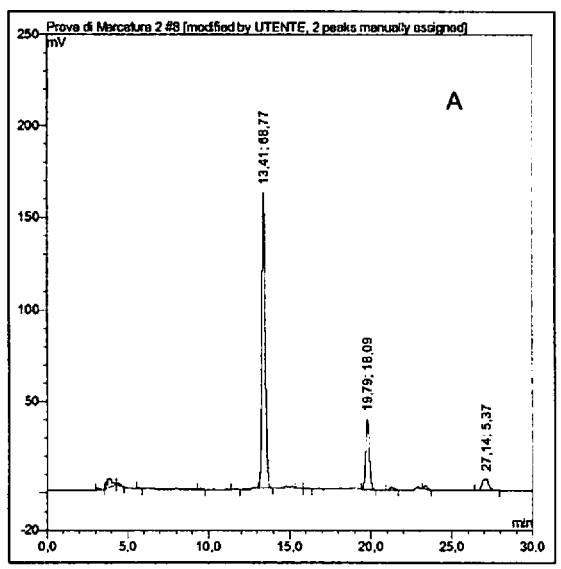
FIG. 16 represents the radio-HPLC profiles of [$^{99m}$Tc(N) (PNP43)(Glu-Urea-Lys-2-naphthyl-L-Ala-Amc-Cys)]$^+$ after 30 min RT (A) and 30 min 80° C. (B). HPLC analysis was performed at the same condition reported for $^{99m}$Tc(N) (PNP3OH)(Glu-Urea-Lys-2-naphthyl-L-Ala-Amc-Cys)]$^+$. RP-HPLC profile of the reaction mixtures indicates the formation, in high yield, of the complexes as a mixture of two syn and anti isomers in different ratios.
Figure 16:
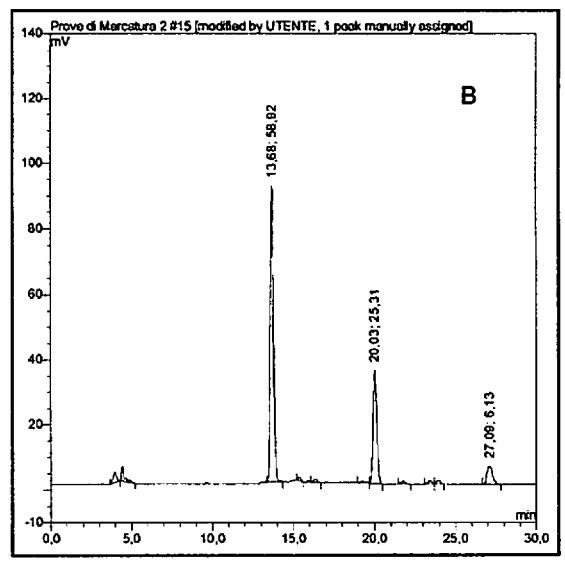

UV-Radio HPLC analyses of the reaction mixture are shown in FIG. 13.

Comparative Example 26: Radiosynthesis of Comparative F, $[^{99m}Tc(N)(PNP3)(Cys-Gly-Lys-Gly-ApoMb)]^-$ ("Cys-Gly-Lys-Gly" Disclosed as SEQ ID NO: 1)

Method 1 (two-step) in PB. To 40 μl (111 MBq) of $[^{99m}Tc\equiv N]_{m/x}^{2+}$ intermediate prepared as above, PNP3 (8 μg in 8 μL of EtOH), PB(42 μl, 0.2 M, pH 7.4) and Cys-Gly-Lys-Gly-ApoMb (SEQ ID NO: 1) (80 μg in 10 μL of TFA 0.01%) were added. The reaction mixture was incubated at room temperature for 30 min.

RCYs are summarized in Table 6.

Comparative Example 27: Radiosynthesis of Comparative G, $[^{99m}Tc(N)(PNP3OH)(ApoMb)]^+$ and Comparative H, $[^{99m}Tc(N)(PNP3OH)(BSA)]^+$ Method 2 (one-step). According to this procedure for comparative purpose a series of reactions were conducted by using, instead of Cys-Gly-Lys-Gly-ApoMb (SEQ ID NO: 1), unmodified apomyoglobin (ApoMb) or human serum albumin (HSA) which do not contain Cys residues suitable or accessible for coordination to the metal fragment.

RCYs are summarized in Table 8.

The radio-chromatogram of $[^{99m}Tc(N)(PNP3OH)(Cys-Gly-Lys-Gly-ApoMb)]^+$ ("Cys-Gly-Lys-Gly" disclosed as SEQ ID NO: 1) is compared with the radio-HPLC profiles of the: a) $^{99m}TC(N)$-intermediates; b)$[^{99m}Tc(N)(PNP3-OH)]^{2+}$ building block(FIG. 14A); and c)test reaction conducted by using the native ApoMb instead of Cys-Gly-Lys-Gly-ApoMb (SEQ ID NO: 1) (FIG. 14B). No peaks resulting from unbound $^{99m}Tc(N)$-intermediates or $[^{99m}Tc(N)(PNP3OH)]^{2+}$ building block were detected to confirm the high specificity and selectivity of these reactions.

Example 28: In Vitro Stability Study

The transchelation studies were performed for some compounds monitoring by HPLC the radiochemical purity (RCP) of the complexes in presence of an excess of exchanging ligands over the time. The experiments were performed in triplicate.

Challenge Reactions.

Challenge experiments were carried out on the purified $[^{99m}Tc(N)(PNP3OH)]$-labeled small size compounds (complex 1, complex 2, complex 9 and complex 10) using an excess of glutathione (GSH) or Cys. An aliquot (50 μl) of an aqueous stock solution of cysteine hydrochloride (10 mM; 1 mM) was added to a propylene test tube containing PB (250 μl, 0.2 M; pH 7.4), water (100 μl) and the selected $[^{99m}Tc(N)(PNP3OH)]$-compound (100 μl). The mixture was vortexed and incubated at 37° C. for 24 h. A control reaction containing an equal volume of water, instead of cysteine hydrochloride, was studied in parallel. At 30 min, 1, 3 and 24 h, aliquots of the reaction mixture were withdrawn and analyzed by HPLC chromatography. A similar procedure was applied using GSH (50 μl, 10 mM) as challenge ligand.

For $[^{99m}Tc(N)(PNP3OH)(Cys-Gly-Lys-Gly-ApoMb)]^+$ ("Cys-Gly-Lys-Gly" disclosed as SEQ ID NO: 1) additional experiments were conducted using EDTA (50 μl, 10 mM) as exchanging ligand.

In general the compounds were found adequately stable toward ligand exchange reactions.

Example 29: Receptor Affinity Studies

Studies were performed to investigate the impact of the $[^{99m}Tc(N)(PNP)]$ building block on the receptor binding affinity of the targeting molecules, biotin and RGD peptide.

Before the experiments for both complex 11 and complex 9, the two isomers were isolated by HPLC and their isomeric conversion was assessed over 24 h at 37° C.

No variation of a vs b and vice versa was observed by incubating complex 11 at 37° C. On the contrary, the reversible a vs b and b vs a conversion was detected for complex 9. Notably, HPLC profile collected immediately after purification of the radiolabeled peptide clearly evidences amounts of the two isomeric species in approximately in 90:10 ratios indicating that a quick conversion of one isomer into another occurred. In addition, a faster b vs a change was noticed. Therefore, for the radiolabeled peptide the mixture of the two isomeric forms in ratio 70/30 was directly utilized for receptor affinity studies.

Avidin Binding. The preliminary evaluation of the binding characteristics of the two separate isomers of complex 11 to avidin was assessed according to the previously reported methods and compared with those of the corresponding already published (Bolzati, C.; Caporale, A.; Agostini, S.; Carta, D.; Cavazza-Ceccato, M.; Refosco, F.; Tisato, F.; Schievano, E.; Bandoli, G. Avidin-biotin system: a small library of cysteine biotinylated derivatives designed for the $[^{99m}Tc(N)(PNp)]^{2+}$ metal fragment. Nucl. Med. Biol (2006), 34, 511-522).

Figure 9:
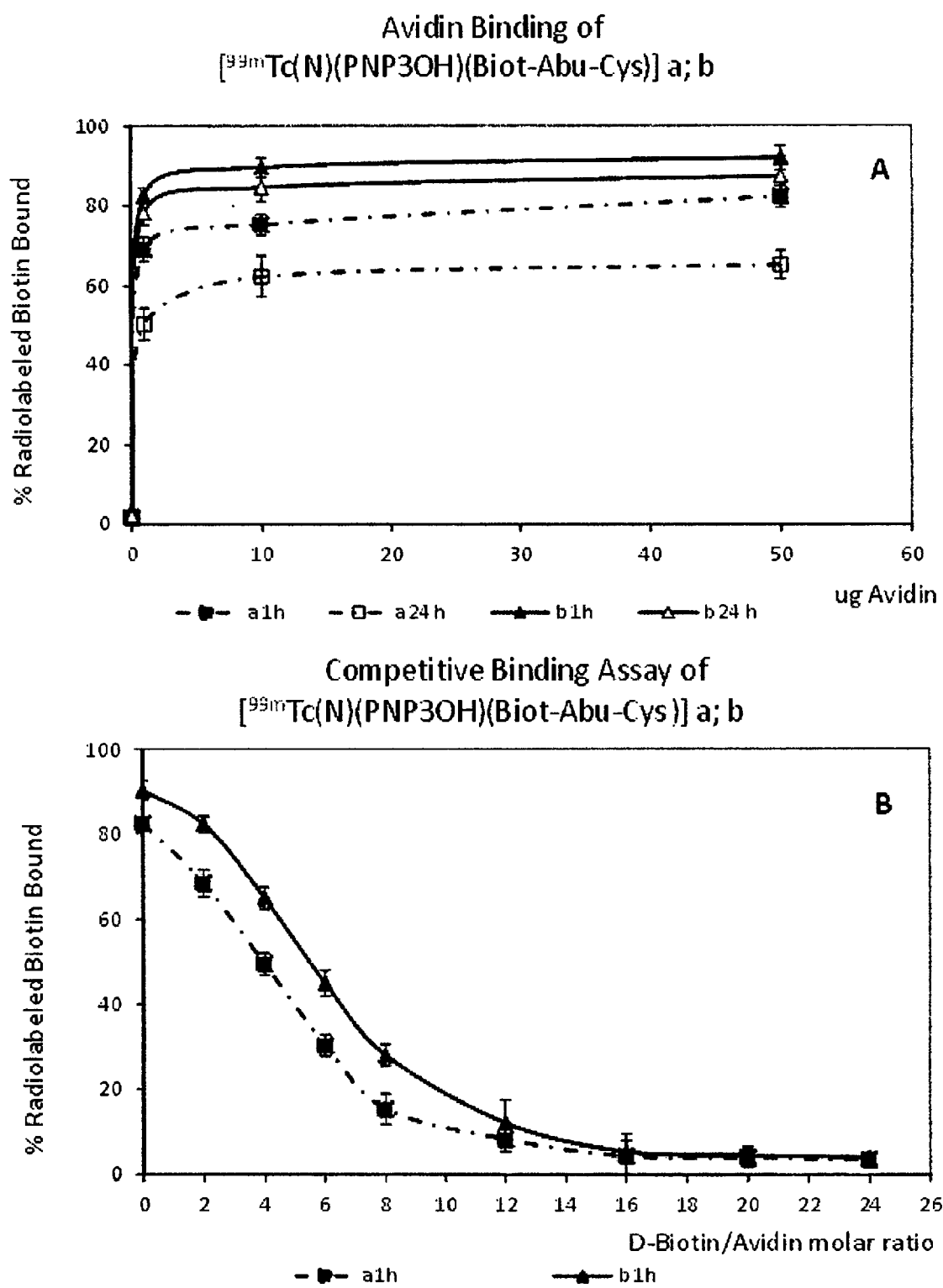
FIG. 9 represents the in vitro binding of complex 11 a,b to avidin, as a function of avidin concentration, evaluated after 1 and 24 h at 37° C. (A) and the saturation curves of complex 11 a,b expressed as % of bound radiolabeled biotin as a function of the D-biotin/avidin molar ratio evaluated after 1 h at 37° C. (B).

The percentage of radiolabeled biotin bound, evaluated after 1 and 24 h of incubation along the saturation curves, is reported in FIG. 9.

Cell Uptake.

Cell Studies of complex 9 were conducted on M21 and M21L cells grown in RPMI1640 (Gibco Life Technologies). Expression of $\alpha_v\beta_3$ and of $\alpha_v\beta_5$ in the cells lines was analyzed by flow cytometry.

Before the cell experiments, the stability of the purified complex 9 in RPMI1640 medium was evaluated. The radiolabeled peptide was found stable. Data were compared with those of the $^{99m}$Tc-HYNIC-RGDfK labeled compound produced according to literature (Decristoforo C, Santos I, Pietzsch H J, Kuenstler J U, Duatti A, Smith C J, Rey A, Alberto R, Von Guggenberg E, Haubner R. Comparison of in vitro and in vivo properties of [99mTc]cRGD peptides labeled using different novel Tc-cores.Q J Nucl Med Mol Imaging. (2007), 51, 33-41).

Thus, to a glass test tube containing 990 μL of cell culture media was added 10 μL of a solution containing 10 μCi of complex 9. The mixture was vortexed and incubated at 37° C. for 2 h. At 30 min, 1 and 2 h, 100 μl of the reaction mixture were withdrawn and analyzed by HPLC chromatography. The radiochemical purity (RCP) of the complexes was found >90%.

Cellular uptakes of the radiolabeled peptide, were assessed in suspension at 37° C. in human melanoma $\alpha_v\beta_3$ positive M21 and negative M21L cell lines. Preliminary studies were performed in order to set the experimental conditions to avoid cell damage and/or death during uptake experiments. With use of these results, the cells were pre-incubated in sterile glass tubes at 37° C. for 30 min in presence or not of the unlabeled c(RGDfK) penta-peptide (50 μl; 1.65 mM). Afterward, 1 ml of the cell suspension ($1\times10^6$ cells/ml) was incubated with intermittent agitation with 10 μCi (10 μL) of $^{99m}$Tc complexes. At 90 min, the tubes were vortexed, the cells were transferred in Eppendorf microcentrifuge tube (1.5 ml) and the incubation was interrupted by centrifugation (3000 rpm for 5 min at 10° C.). The supernatant was separated from the pellet and the bottom tip containing the cell pellet was treated at room temperature with saline acetate buffer ($CH_3COOH$ 0.2 M/NaCl 0.5 M), to remove membrane bound compound. After centrifugation (3000 rpm for 10 min at 10° C.) the supernatant was separated from the pellet, each fraction was collected, placed in a separated counting tube and the activity was determined using a counter (Cobra II, Packard) to determinate both the cell uptake and internalized fraction.

The uptake of complexes is expressed as percentage cell uptake of the total activity on $10^6$ cells (% cell uptake/$10^6$ cells).

All assessments were conducted in triplicate for three experiments.

Figure 10:
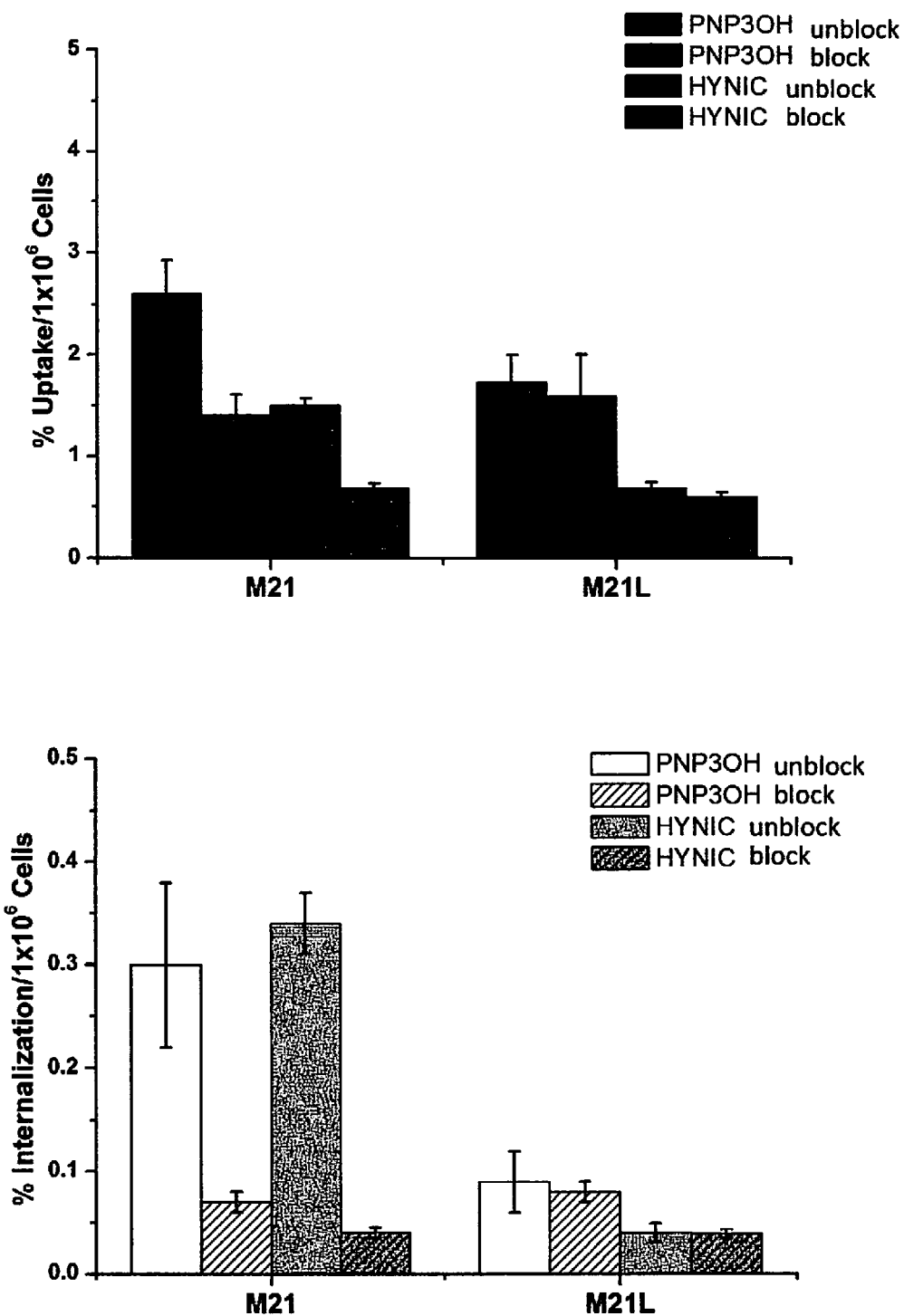
FIG. 10 represents the cellular uptake and internalization data of complex 9 (reported as PNP3OH) compared with those of $^{99m}$Tc-HYNIC-RGDfK (reported as HYNIC) in $\alpha_v\beta_3$ positive M21 and $\alpha_v\beta_3$ negative M21L cell lines.

Data are summarized in FIG. 10.

Example 30. In Vitro Evaluation

Serum Protein binding. The affinity of complex 1, complex 2 and complex 9 to the serum proteins was evaluated by chromatographic methods, using size exclusion chromatography.

In a propylene test tube, 100 μl of the purified complex (50-100 MBq) were added to 900 μl of human or rat serum; at 15, 60, 120 and 240 min of incubation at 37° C., 25 μl of each sample were withdrawn and loaded on a pre-spun (735×g for 2 min) Sephadex G-50 mini-column. The column was centrifuged at 735×g for 1 min. The collected eluate and the column were counted in a NaI-scintillation counter. The protein-bound complex was calculated as the percentage of the total activity.

Sera and Homogenates Stability.

The in vitro stability of complex 1, complex 2, complex 9 and complex 11 was evaluated by monitoring the RCP at different time points using the following procedures. In a propylene test tube 50 μl of purified $[^{99m}Tc(N)(PNP3OH)]$-compound were added to: a) 450 μl of human serum, b) 450 μl of rat serum, c) 450 μl of homogenate of rat liver and d) 450 μl of homogenate of rat kidneys. The resulting mixture was incubated at 37° C. for 4 h.

Figure 11:
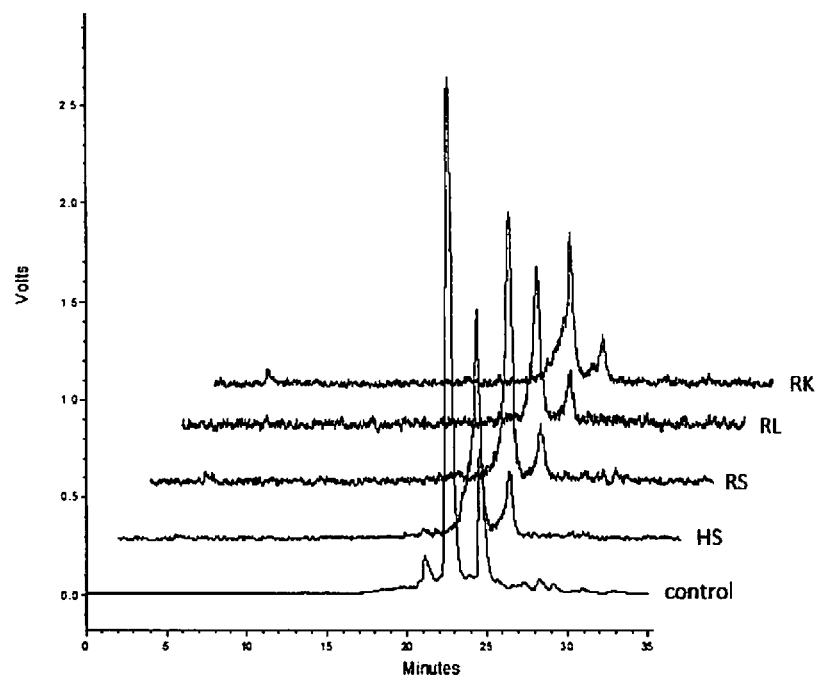
FIG. 11 represents the HPLC profiles of complex 9 after incubation, at 37° C. for 2 h, in: human serum (HS), rat serum (RS), rat liver homogenate (RL) and rat kidneys homogenate (RK); control is the native compound (prior incubation). HPLC analysis was performed with a Reverse Phase Vydac 218TP C18 precolumn (5 µm 4,6×45 mm) and Vydac 218TP C18 column (5 µm 4.6×250 mm). UV detector: $\lambda$=215 m; flow rate of 1 mL/min. Solvents: A H$_2$O TFA 0.1%; B AcCN THF 0.1%. Gradient: 0 min, % B=5; 3-25 min, % B=25; 28-29 min, % B=80; 29-32 min, % B=80; 32-34 min, % B=5; 34-35 min, % B=5.

At 15, 60, 120 and 240 min, (50 μl) of each solution were withdrawn, diluted with 950 μl of PB (0.02 M, pH 7.4) and passed through OASIS HLB extraction cartridge before HPLC injection. The sample was loaded onto a cartridge, preconditioned with MeOH (1 ml) and equilibrated with water (1 ml), and rinsed with MeOH 5% (3 ml). The activity was eluted with a mixture of EtOH/saline 60% (1 ml). Each fraction was collected and the activity measured using a counter (Cobra II, Packard) to determinate the elution profile. 80% of the loaded activity was collected in the elution fraction. An aliquot of this solution (100 μl) was analyzed by HPLC to assess the degradation of the $^{99m}$Tc(N)-complexes (FIG. 11).

Example 31. In Vivo Studies

All animal experiments in rodent models were carried out according to the guidelines of the National Regulations for Animal Welfare. The protocol is approved by the local Ethical Committee for Animal Experiment. The animals were housed under standard conditions in controlled-airflow cabinets with free access to standard food and tap water.

Before injection, $^{99m}$Tc complexes were purified using a reversed-phase C18 Sep-Pack cartridge to remove the excess of unlabeled ligands. After purification, the activity recovered was further diluted with PBS to obtain a final solution that is <0.5% in EtOH content. The RCP and the stability of the purified complexes were evaluated prior to in vivo administration and for the succeeding 18 h.

Biodistribution in healthy rats. Biodistribution in healthy rats was performed on complex 1, complex 2 and complex 9 in order to evaluate their pharmacokinetic profile and elimination pathways as well as their resistance to in vivo metabolism. Female Sprague-Dawley rats weighing 180-200 g were anesthetized with an intramuscular injection of a mixture of Zoletil (40 mg/kg) and xylazine (2 mg/kg). A jugular vein was surgically exposed and 100 μl (300-370 kBq) of the solution containing the selected $[^{99m}Tc(N)(PNP3OH)]$-compound was injected. The rats (n=3) were scarified by cervical dislocation at different times after injection. The blood was withdrawn from the heart with a syringe immediately after death and quantified. Organs were excised, rinsed in saline, weighed, and the activity was counted in a NaI well counter.

The results expressed as the percentage of injected dose per gram (% ID/g) are summarized in Tables 9 and 10.

Metabolites in the Urine.

At 2 and 4 h p.i. the urine was collected directly from the bladder and analyzed by HPLC (FIG. 12).

Distribution in Tumor Bearing Mice.

Tumor uptake studies were performed on complex 9 in NOD/SCID mice to determine the effective capability of the complex to detect in vivo endogenously expressed $\alpha_v\beta_3$ integrins. For induction of tumor xenografts, M21 ($\alpha_v\beta_3$ positive) and M21L ($\alpha_v\beta_3$ negative) cells were subcutaneously injected at a concentration of $5\times10^6$ cells/mouse and allowed to grow until tumor of 3 mm is palpable. The solution containing the purified radiolabeled peptide (15 μCi/200 μL) was injected intravenously into the tail vein. The animals (n=5) were sacrificed by cervical dislocation at 2 h post injection. Tumors and other tissues (blood, heart, lung, liver, kidneys, stomach, intestine, muscle) were removed, weighed, and the activity was counted in a NaI well counter. The results were expressed as the percentage of injected activity per gram of tissue (% IA/g) and tumor to organ ratios were calculated.

Data are summarized in Table 12.

The (%)RCY of formation obtained, both at 30 and 60 minutes, from some representative compounds according to the invention, prepared by Method 1 and Method 2, are summarized and compared with corresponding values measured for some comparative compounds in the following Table 1, Table 2, Table 3, Table 4, Table 5, Table 6, Table 7, Table 8.

The dependence of (%)RCY of formation of some compounds of the invention along with the distribution of each isomeric form on the concentration of the ZY ligands is illustrated in FIG. 7 and FIG. 8.

The dependence of (%)RCY of formation of a compound of the invention along with the concentration of the ZY ligands is reported in Table 9.

The variation of (%)RCY of complex 1 and complex 2 over the time, at different pH conditions, is shown in FIG. 5.

HPLC profiles of some compounds of formula $[^{99m}Tc(N)(PNP3OH)(YZ)]^{0/+}$ are shown in FIG. 4, FIG. 6A, FIG. 6B, FIG. 13, FIG. 14 and FIG. 15.

Receptor affinity studies are summarized in FIG. 9 and FIG. 10, while biodistribution studies in healthy rats and in tumor bearing mice are summarized in Table 10, Table 11, Table 12.

In vitro and in vivo stability of the radiolabeled peptide is illustrated in FIG. 11 and FIG. 12.

These results confirm that the particular selection represented by the compounds of the invention allows the $^{99m}$Tc-labeling of bioactive molecules at room temperature and in mild reaction conditions in high yields.

TABLE 1

Labeling conditions and % RCY for the preparation of $[^{99m}Tc(N)(PNP)(ZY)]^{0/+}$ (ZY = CysNAc; CysOEt; CysGly).

| Complex | HPLC $R_T$ | PNP (mg) | YZ (mg) | % RCY Method 1 Two-step in PB ($V_{fin}$ = 1 ml; $pH_{fin}$ = 7.4) | |
|---|---|---|---|---|---|
| | | | | 30 min | 60 min |
| $[^{99m}Tc(N)]int$ | 3.54 | | | | |
| $[^{99m}Tc(N)(PNP3OH)(X)_2]$ | 23.28[1] | | | | |
| | | PNP3OH•HCl | | | |
| Complex 1 $[^{99m}Tc(N)(PNP3OH)(CysNAc)]$ | 17.75[1] | 1 mg | 0.150 mg (9.12 10$^{-4}$ mmol) | 89.74 | 91.03 |
| | 18.94[1] | | 0.050 mg (3.06 10$^{-4}$ mmol) | | |
| Complex 2 $[^{99m}Tc(N)(PNP3OH)(CysOEt)]^+$ | 24.67[1] | 1 mg | 0.150 (8.10 10$^{-4}$ mmol) | | |
| | 27.62[1] | | 0.010 mg (5.3 10$^{-5}$ mmol) | 91.58 | 91.96 |
| Complex 3 $[^{99m}Tc(N)(PNP3OH)(CysGly)]^+$ | 16.05[1] | 1 mg | 0.010 mg (5.61 10$^{-5}$ mmol) | 92.87 | 92.69 |
| | 16.95[1] | | 0.005 mg (2.89 10$^{-5}$ mmol) | | |
| | | PNP43 | | | |
| Complex 4 $[^{99m}Tc(N)(PNP43)(CysGly)]^+$ | 19.43[1] | 0.250 mg | 0.010 mg (5.61 10$^{-5}$ mmol) | 88.11 | |
| | 22.92[1] | | | | |
| | | PNP3 | | | |
| Comparative A $[^{99m}Tc(N)(PNP3)(CysGly)]^+$ | 19.58[2] | 1 mg | 0.010 mg (5.61 10$^{-5}$ mmol) | 44.69 | |
| | 22.46[2] | | | | |

TABLE 1-continued

Labeling conditions and % RCY for the preparation of
[$^{99m}$Tc(N)(PNP)(ZY)]$^{0/+}$ (ZY = CysNAc; CysOEt; CysGly).

| Complex | % RCY Method 2 One-step in PB ($V_{fin}$ = 1 ml; $pH_{fin}$ = 7.4) | | % RCY Method 2 One-step in PBS ($V_{fin}$ = 1.5 ml; $pH_{fin}$ = 7.4) | |
|---|---|---|---|---|
| | 30 min | 60 min | 30 min | 60 min |
| [$^{99m}$Tc(N)]int [$^{99m}$Tc(N)(PNP3OH)(X)$_2$] | | | | |
| Complex 1 [$^{99m}$Tc(N)(PNP3OH)(CysNAc)] | 91.36 ± 1.67* 89.65 | 91.28 ± 2.30* 86.58 | 87.29 ± 2.00* 84.56 | 90.85 ± 1.27* 86.23 |
| Complex 2 [$^{99m}$Tc(N)(PNP3OH)(CysOEt)]$^+$ | 89.73 89.73 ± 1.91* | 90.31 89.38 ± 2.5* | | |
| Complex 3 [$^{99m}$Tc(N)(PNP3OH)(CysGly)]$^+$ | 94.56 ± 1.20* 94.03 ± 1.07* | 94.73 ± 1.23* 94.13 ± 1.00* | 94.48 ± 2.3* | 94.73 ± 2.51* |
| Complex 4 [$^{99m}$Tc(N)(PNP43)(CysGly)]$^+$ | 87.78 | | | |
| Comparative A [$^{99m}$Tc(N)(PNP3)(CysGly)]$^+$ | 49.07 | | | |

HPLC Analysis: Solvents A H$_2$O TFA 0.1%; B AcCN TFA 0.1%.
[1]gradient: 0 min, % B = 0; 3-28 min, % B = 25; 28-29 min, % B = 80; 29-32 min, % B = 80; 32-33 min, % B = 0; 33-34 min, % B = 0.
[2]gradient: 0 min, % B = 15; 3-28 min, % B = 40; 28-29 min, % B = 80; 29-33 min, % B = 80; 33-34 min, % B = 15; 33-34 min, % B = 15.
*Data are expressed as mean ± standard deviation, n = 3.
HPLC was performed on a Dionex Ultimate 3000 (Thermo Scientific, Rodano, Milan, Italy) equipped with a radioisotope detector (Gabi Raytest). Data were elaborated by Chromeleon 6.8 software. HPLC analysis was performed with a Waters SymmetryShield RP C18 Guard Column, 5.0 μm, 100 Å, 3.9 × 20 mm) and Waters SymmetryShield RP C18 column (5.0 μm, 100 Å, 4.6 × 250 mm). UV detector: λ 216 nm; Flow rate of 1 mL/min. For each compound, retention time of syn and anti isomers is reported,

TABLE 2

Labeling condition and % RCY for the preparation of [$^{99m}$Tc(N)(PNP)(DT-OEt)].

| Complex | HPLC $R_T$ | PNP | % RCY Method 1 Two-step in PB | | % RCY* Method 2 One-step in PB | | % RCY Method 2 One-step in PBS | |
|---|---|---|---|---|---|---|---|---|
| | | | 30 min | 60 min | 30 min | 60 min | 30 min | 60 min |
| [$^{99m}$Tc(N)]int [$^{99m}$Tc(N)(PNP3OH)(X)$_2$] | 3.98; 12.99[1] | | | | | | | |
| | | PNP3OH•HCl | | | | | | |
| Complex 5 [$^{99m}$Tc(N)(PNP3OH)(DT-OEt)] | 20.12[1] 22.73[1] | | 88.87 | 86.58 | 86.13 ± 0.72* | 88.66 ± 0.75* | 85.68 | 88.42 |
| | | PNP43 | | | | | | |
| Complex 6 [$^{99m}$Tc(N)(PNP43)(DT-OEt)] | 23.02[2] 17.25[3] 23.75[2] 17.85[3] | | 68.39 | 71.38 | 73.29 ± 11.30* | 85.71 ± 1.27* | | |
| | | PNP3 | | | | | | |
| Comparative B [$^{99m}$Tc(N)(PNP3)(DT-OEt)] | 29.83[3] 30.45[3] | | 32.73 | 40.61 | 37.57 ± 6.53* | 42.48 ± 5.50* | | |

HPLC Analysis. Solvents A H$_2$O TFA 0.1%; B AcCN TFA 0.1%.
[1]Gradient: 0 min, % B = 10; 3-28 min, % B = 35; 28-29 min, % B = 80; 29-32 min, % B = 80; 32-33 min, % B = 10; 33-34 min, % B = 10.
[2]Gradient: 0 min, % B = 15; 3-28 min, % B = 40; 28-29 min, % B = 80; 29-33 min, % B = 80; 33-34 min, % B = 15; 33-34 min, % B = 15.
[3]Gradient: 0 min, % B = 20; 3-28 min, % B = 45; 28-29 min, % B = 80; 29-32 min, % B = 80; 32-33 min, % B = 20; 33-34 min, % B = 20.
*Data are expressed as mean ± standard deviation, n = 3.
HPLC was performed on a Dionex Ultimate 3000 (Thermo Scientific, Rodano, Milan, Italy) equipped with a radioisotope detector (Gabi Raytest). Data were elaborated by Chromeleon 6.8 software. HPLC analysis was performed with a Waters SymmetryShield RP C18 Guard Column, 5.0 μm, 100 Å, 3.9 × 20 mm) and Waters SymmetryShield RP C18 column (5.0 μm, 100 Å, 4.6 × 250 mm). UV detector: λ 216 nm; Flow rate of 1 mL min. For each compound, retention time of syn and anti isomers is reported,

TABLE 3

Labeling conditions and % RCY for the preparation of [$^{99m}$Tc(N)(PNP)(DT-OH)].

| Complex | HPLC $R_T$ | PNP | % RCY Method 1 Two-steps hydroalcoholic solution | | % RCY Method 2 One-step hydroalcoholic solution in PB | | % RCY Method 2 One-step hydroalcoholic solution in PBS |
|---|---|---|---|---|---|---|---|
| | | | 30 min | 60 min | 30 min | 60 min | 30 min |
| [$^{99m}$Tc(N)(PNP3OH)(X)$_2$] | 22.88[1§] | PNP3OH•HCl | | | | | |
| Complex 7 [$^{99m}$Tc(N)(PNP3OH)(DT-OH)] | 18.60 ± 0.05[1¥] 19.97 ± 0.05[1¥] | | 95.23 | | 96.60 ± 1.59[¥] | | 92.82 ± 1.19[¥] |
| | | PNP43 | | | | | |
| Complex 8 [$^{99m}$Tc(N)(PNP43)(DT-OH)] | 15.00 ± 0.05[2] 15.95 ± 0.05[2] | | 80.53 | 92.25 | 28.66 ± 9.49 | 42.09 ± 8.05[¥] | |
| | | PNP3 | | | | | |
| Comparative C [$^{99m}$Tc(N)(PNP3)(DT-OH)] | 18.25 ± 0.08[3] 19.61 ± 0.09[3] | | 61.11 | | 62.30 ± 2.12 | 68.59 ± 1.50* | |

HPLC Analysis. Solvents A H$_2$O TFA 0.1%; B AcCN TFA 0.1%.
[1]Gradient: 0 min, % B = 0; 3-28 min, % B = 25; 28-29 min, % B = 80; 29-32 min, % B = 80; 32-33 min, % B = 0; 33-34 min.
[2]Gradient: 0 min, % B = 10; 3-28 min, % B = 35; 28-29 min, % B = 80; 29-32 min, % B = 80; 32-33 min, % B = 10; 33-34 min.
[3]Gradient: 0 min, % B = 20; 3-28 min, % B = 45; 28-29 min, % B = 80; 29-32 min, % B = 80; 32-33 min, % B = 20; 33-34 min.
*Except where indicated, no significant increasing of the % RCY is observed at 60 min.
[§]Main peak.
[¥]Data are expressed as mean ± standard deviation, n = 3 at least. HPLC was performed on a Dionex Ultimate 3000 (Thermo Scientific, Rodano, Milan, Italy) equipped with a radioisotope detector (Gabi Raytest). Data were elaborated by Chromeleon 6.8 software. HPLC analysis was performed with a Waters SymmetryShield RP C18 Guard Column, 5.0 μm, 100 Å, 3.9 × 20 mm) and Waters SymmetryShield RP C18 column (5.0 μm, 100 Å, 4.6 × 250 mm). UV detector: λ 216 nm; Flow rate of 1 mL/min. For each compound, retention time of syn and anti isomers is reported,

TABLE 4

Labeling conditions and % RCY for the preparation of [$^{99m}$Tc(N)(PNP)(Cys-cRGDfK)]$^+$ by Method 1.

| Complex | PNP (mg/ml) | Cys-cRGDfK (mg/μl) | V (ml) | % RCY Method 1 Two-step | |
|---|---|---|---|---|---|
| | | | | 30 min | 60 min |
| | PNP3OH•HCl | | | | |
| Complex 9 [$^{99m}$Tc(N)(PNP3OH)(Cys-cRGDfK)]$^+$ | 1 mg/0.2 ml PB 0.2M pH 7.4 | 0.05 mg/50 μl Sal (final conc 4.15 10$^{-5}$M) | 1.5 ml | 93.78 ± 3.81* | 94.02 ± 2.91* |
| | PNP43 | | | | |
| Complex 10 [$^{99m}$Tc(N)(PNP43)(Cys-cRGDfK)]$^+$ | 0.5 mg/0.5 ml γ-cyclodextrin 4 mg/ml | 0.05 mg/50 μl Sal (final conc 4.15 10$^{-5}$M) | 1.5 ml | | 73.80 |
| | PNP3 | | | | |
| Comparative D [$^{99m}$Tc(N)(PNP3)(Cys-cRGDfK)]$^+$ | 1 mg/0.5 ml γ-cyclodextrin 4 mg/ml | 0.05 mg/50 μl Sal (final conc 4.15 10$^{-5}$M) | 1.5 ml | 55.74 | 65.61 |

*Data are expressed as mean ± standard deviation, n = 3.

TABLE 5

Labeling conditions and % RCY for the preparation of [$^{99m}$Tc(N)(PNP)(Biot-Abu-Cys)] by Method 1.

| Complex | PNP | % RCY Method 1 Two-step in PB 30 min |
|---|---|---|
| | PNP3OH•HCl | |
| Complex 11 [$^{99m}$Tc(N)(PNP3OH)(Biot-Abu-Cys)] | | 88.30 |
| | PNP3 | |
| Comparative E [$^{99m}$Tc(N)(PNP3)(Biot-Abu-Cys)] | | 40.02 |

TABLE 6

Labeling conditions and % RCY for the preparation of [$^{99m}$Tc(N)(PNP)(Cys-Gly-Lys-Gly-ApoMb)]$^+$ by Method 1.

| Complex | PNP (M) | Cys-Gly-Lys-Gly-ApoMb (SEQ ID NO: 1) (M) | V (μl) | % RCY Method 1 Two-step in PB 30 min |
|---|---|---|---|---|
| | PNP3OH•HCl | | | |
| [$^{99m}$Tc(N)(PNP3OH)(Cys-Gly-Lys-Gly-ApoMb)]$^+$ ("Cys-Gly-Lys-Gly" disclosed as SEQ ID NO: 1) | 5 μg/5 μl PB 0.2M pH 7.4 (final conc 1.6 $10^{-4}$M) | 80 μg/10 μl TFA 0.1% (final conc 4.6 $10^{-5}$M) | 100 μl | 93.47 |
| | PNP3 | | | |
| Comparative F [$^{99m}$Tc(N)(PNP3)(Cys-Gly-Lys-Gly-ApoMb)]$^+$ ("Cys-Gly-Lys-Gly" disclosed as SEQ ID NO: 1) | 8 μg/8 μl EtOH (final conc 1.6 $10^{-4}$M) | 80 μg/10 μl TFA 0.1% (final conc 4.6 $10^{-5}$M) | 100 μl | 38.31 |

TABLE 7

Labeling condition and % RCY for the preparation of $^{99m}$Tc(N)(PNP3OH)(Glu-Urea-Lys-2-naphthyl-L-Ala-Amc-Cys)]$^+$ and $^{99m}$Tc(N)(PNP43)(Glu-Urea-Lys-2-naphthyl-L-Ala-Amc-Cys)]$^+$

| Complex | HPLC $R_T$ | PNP | % RCY Method 1 Two-step in PB 30 min | 60 min | % RCY Method 2 One-step in PB 30 min | 60 min |
|---|---|---|---|---|---|---|
| [$^{99m}$Tc(N)] int | 3.29 ± 0.05 | | | | | |
| [$^{99m}$Tc(N)(PNP3OH)]$^{2+}$ | 3.79 ± 0.03 | | | | | |
| | | PNP3OH•HCl | | | | |
| Complex 12 $^{99m}$Tc(N)(PNP3OH)(Glu-Urea-Lys-2-naphthyl-L-Ala-Amc-Cys)]$^+$ | 9.15 ± 0.06 12.53 ± 0.08 | | 89.03 ± 1.15 | 90.15 ± 2.2 | 86.74 | 87.5 |
| | | PNP43 | | | | |
| Complex 13 $^{99m}$Tc(N)(PNP43)(Glu-Urea-Lys-2-naphthyl-L-Ala-Amc-Cys)]$^+$ | 13.55 ± 0.11 19.92 ± 0.10 | | 86.59 ± 0.24 | 86.50 ± 0.30 | | |

HPLC Analysis. Solvents A H$_2$O TFA 0.1%; B AcCN TFA 0.1%.
Gradient: 0 min, % B = 25; 1 min, % B = 25; 17 min, % B = 32; 23 min, % B = 32; 24 min, % B = 90; 28 min, % B = 90; 29 min, % B = 25; 30 min, % B = 25. Data are expressed as mean ± standard deviation, n = 3. For each compound, retention time of syn and anti isomers is reported.

TABLE 8

% RCY for [$^{99m}$Tc(N)(PNP3OH)(ApoMb)]$^+$ and [$^{99m}$Tc(N)(PNP3OH)(BSA)]$^+$.

| Complex | % RCY Method 2 One-step 30 min |
|---|---|
| Comparative G [$^{99m}$Tc(N)(PNP3OH)(ApoMb)]$^+$ | 0.91 |
| Comparative H [$^{99m}$Tc(N)(PNP3OH)(BSA)]$^+$ | 0.50 |

TABLE 9

Dependence of RCY of complex 7 on the DT-OH concentration.

| PNP3OH•HCl (mg) | DT-OH (mg) | [DT-OH] | % RCY 30 min |
|---|---|---|---|
| 1 mg | 0.78 | 6.29 × $10^{-3}$M | 74.57 |
| 1 mg | 0.078 | 6.29 × $10^{-4}$M | 89.31 |
| 1 mg | 0.0078 | 6.29 × $10^{-5}$M | 95.34 |
| 1 mg | 0.00078 | 6.29 × $10^{-6}$M | 96.60 ± 1.59* |
| 1 mg | 0.000156 | 1.26 × $10^{-6}$M | 96.29 ± 1.59* |
| 1 mg | 0.000078 | 6.29 × $10^{-7}$M | 95.06 |

*Data are expressed as mean ± standard deviation, n = 3.

TABLE 10

Biodistribution studies of the complex 1 and complex 2 (data are expressed as % IA/g).

Complex 1 [$^{99m}$Tc(N)(PNP3OH)(CysNAc)]

| Organ | 2 min | 10 min | 30 min | 60 min | 120 min |
| --- | --- | --- | --- | --- | --- |
| Blood | 1.68 ± 0.02 | 0.96 ± 0.03 | 0.43 ± 0.09 | 0.11 ± 0.00 | 0.06 ± 0.01 |
| Brain | 0.10 ± 0.01 | 0.05 ± 0.01 | 0.04 ± 0.01 | 0.01 ± 0.00 | 0.01 ± 0.00 |
| Heart | 0.54 ± 0.09 | 0.27 ± 0.01 | 0.17 ± 0.07 | 0.06 ± 0.01 | 0.02 ± 0.00 |
| Lungs | 1.11 ± 0.22 | 0.68 ± 0.03 | 0.38 ± 0.15 | 0.14 ± 0.01 | 0.10 ± 0.01 |
| Liver | 1.73 ± 0.02 | 2.27 ± 0.01 | 1.28 ± 0.03 | 0.99 ± 0.13 | 0.54 ± 0.05 |
| Spleen | 0.40 ± 0.07 | 0.26 ± 0.00 | 0.10 ± 0.01 | 0.10 ± 0.01 | 0.09 ± 0.01 |
| Kidneys | 4.73 ± 0.37 | 4.07 ± 0.67 | 2.47 ± 0.04 | 1.15 ± 0.12 | 0.77 ± 0.26 |
| Intestine | 0.70 ± 0.02 | 2.85 ± 0.67 | 5.46 ± 3.28 | 10.07 ± 0.26 | 0.57 ± 0.05 |
| Stomach | 0.39 ± 0.05 | 0.41 ± 0.09 | 0.35 ± 0.02 | 0.24 ± 0.12 | 0.25 ± 0.06 |
| Muscle | 0.32 ± 0.02 | 0.14 ± 0.01 | 0.11 ± 0.00 | 0.08 ± 0.03 | 0.02 ± 0.00 |
| Urine | — | 31.28 ± 4.07 | — | 58.89 ± 2.27 | 55.74 ± 14.87 |

Complex 2 [$^{99m}$(N)(PNP3OH)(CysOEt]$^+$

| Organ | 2 min | 10 min | 30 min | 60 min | 120 min |
| --- | --- | --- | --- | --- | --- |
| Blood | 0.99 ± 0.18 | 0.62 ± 0.11 | 0.62 ± 0.06 | 0.24 ± 0.06 | 0.09 ± 0.09 |
| Brain | 0.05 ± 0.00 | 0.07 ± 0.01 | 0.05 ± 0.03 | 0.02 ± 0.01 | 0.01 ± 0.01 |
| Heart | 0.41 ± 0.07 | 0.26 ± 0.01 | 0.23 ± 0.02 | 0.09 ± 0.03 | 0.06 ± 0.06 |
| Lungs | 0.87 ± 0.17 | 0.50 ± 0.04 | 0.43 ± 0.00 | 0.19 ± 0.05 | 0.15 ± 0.14 |
| Liver | 0.99 ± 0.28 | 1.56 ± 0.06 | 1.85 ± 0.13 | 1.83 ± 0.05 | 0.29 ± 0.77 |
| Spleen | 0.23 ± 0.01 | 0.17 ± 0.00 | 0.15 ± 0.00 | 0.11 ± 0.05 | 0.07 ± 0.04 |
| Kidneys | 5.38 ± 0.22 | 6.20 ± 0.51 | 6.43 ± 2.44 | 2.63 ± 1.43 | 1.67 ± 1.04 |
| Intestine | 0.39 ± 0.09 | 1.35 ± 0.19 | 1.26 ± 0.42 | 2.92 ± 0.26 | 6.23 ± 0.35 |
| Stomach | 0.49 ± 0.05 | 0.44 ± 0.08 | 0.32 ± 0.02 | 0.20 ± 0.12 | 0.31 ± 0.16 |
| Muscle | 0.19 ± 0.07 | 0.17 ± 0.04 | 0.21 ± 0.01 | 0.07 ± 0.04 | 0.04 ± 0.04 |
| Urine | 16.32 ± 0.00 | 25.65 ± 16.29 | 17.06 ± 0.00 | 40.14 ± 0.00 | 20.10 ± 6.28 |

TABLE 11

Biodistribution studies of the radiolabeled RGD peptide complex 9 in healthy rats (data are expressed as % IA/g).

Complex 9 [$^{99m}$Tc(N)(PNP3OH)(Cys-cRGDfK)]$^+$

| Organ | 30 min | 60 min | 120 min | 240 min |
| --- | --- | --- | --- | --- |
| Blood | 0.46 ± 0.17 | 0.25 ± 0.03 | 0.16 ± 0.11 | 0.12 ± 0.01 |
| Heart | 0.25 ± 0.06 | 0.15 ± 0.00 | 0.13 ± 0.05 | 0.22 ± 0.13 |
| Lungs | 0.62 ± 0.15 | 0.49 ± 0.01 | 0.37 ± 0.15 | 0.42 ± 0.06 |
| Liver | 0.90 ± 0.16 | 0.80 ± 0.06 | 0.75 ± 0.19 | 0.88 ± 0.04 |
| Spleen | 0.41 ± 0.10 | 0.39 ± 0.04 | 0.34 ± 0.05 | 0.47 ± 0.04 |
| Kidneys | 4.50 ± 1.59 | 4.20 ± 0.35 | 3.13 ± 1.69 | 7.24 ± 0.55 |
| Intestine | 1.29 ± 0.13 | 1.95 ± 0.97 | 3.76 ± 0.17 | 3.94 ± 0.91 |
| Stomach | 0.62 ± 0.14 | 0.64 ± 0.09 | 0.62 ± 0.09 | 0.61 ± 0.11 |
| Muscle | 0.17 ± 0.01 | 0.13 ± 0.01 | 0.12 ± 0.05 | 0.11 ± 0.00 |
| Urine | 28.98 ± 7.22 | 28.16 ± 2.49 | 34.58 ± 10.09 | 24.91 ± 1.00 |

TABLE 12

Biodistribution studies of the radio labeled RGD peptide complex 9 in tumor bearing mice at 120 min post injection (data are expressed as % IA/g).

| Organs | Complex 9 [$^{99m}$Tc(N)(PNP3OHXCys-cRGDfK)]$^+$ |
| --- | --- |
| Blood | 0.03 ± 0.01 |
| Heart | 0.44 ± 0.09 |
| Lungs | 1.22 ± 0.25 |
| Liver | 3.87 ± 0.81 |
| Spleen | 1.51 ± 0.22 |
| Kidney | 3.19 ± 0.18 |
| Stomach | 0.96 ± 0.20 |
| Intestine | 5.05 ± 1.24 |
| Muscle | 0.20 ± 0.07 |
| M21 | 4.38 ± 0.69 |
| M21L | 1.05 ± 0.62 |
| M21/blood | 146 |
| M21/liver | 1.13 |
| M21/lung | 3.59 |
| M21/muscle | 21.9 |

The invention claimed is:

1. A compound of formula (I)

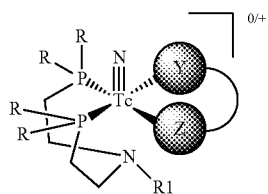

(I)

wherein:

Tc is $^{99m}$Tc;

R is hydrogen (—H) or a group of formula —(CH$_2$)$_n$-A, wherein n is an integer of 1 or 2 and A is selected from the group consisting of hydrogen (—H), hydroxyl (—OH), methyl (—CH$_3$), carboxyl (—COOH), sodium carbonyl (—COONa), amino (—NH$_2$), cyanide (—CN), sulfonyl (—SO$_3$H) and sodium sulfonyl (—SO$_3$Na);

R$_1$ is a group of formula —(CH$_2$)$_m$—R$_2$, wherein m is an integer of 1 to 6 and R$_2$ is selected from the group consisting of alkoxyl (—O-Ak), hydroxyl (—OH), carboxyl (—COOH), and amino (—NH$_2$); and ZY is a bidentate ligand, coordinated with Tc through a combination of electron-donating atoms selected from the group consisting of [O$^-$,S$^-$], [S–,S$^-$], [O$^-$,S], [O,S$^-$], [N,S$^-$], [N$^-$,S], and [N$^-$,S$^-$], wherein ZY is not coordinated with Tc through [N,S$^-$] if R is —CH$_3$ and R$_1$ is —(CH$_2$)$_2$—OCH$_3$.

2. The compound according to claim 1, wherein R is selected from the group consisting of hydrogen (—H), methyl (—CH$_3$), hydroxymethyl (—CH$_2$OH), ethyl (—CH$_2$CH$_3$), and carboxyethyl (—CH$_2$CH$_2$COOH).

3. The compound according to claim 1, wherein m is 2 and R$_2$ is methoxyl (—OCH$_3$).

4. The compound according to claim 1, wherein n is 1 and A is hydroxyl (—OH).

5. The compound according to claim 1, wherein ZY is selected from the group consisting of CysNAc, CysOEt, CysGly, DT-OEt, DT-OH, Cys, Abu-Cys, Cys-Gly-Lys-Gly (SEQ ID NO: 1), and HDTCZ.

6. The compound according to claim 1 selected from the group consisting of:

[$^{99m}$Tc(N)(PNP3OH)(CysNAc)];
[$^{99m}$Tc(N)(PNP3OH)(CysOEt)]$^+$;
[$^{99m}$Tc(N)(PNP3OH)(CysGly)]$^+$;
[$^{99m}$Tc(N)(PNP3OH)(DT-OEt)];
[$^{99m}$Tc(N)(PNP43)(DT-OEt];
[$^{99m}$Tc(N)(PNP3OH)(DT-OH)];
[$^{99m}$Tc(N)(PNP43)(DT-OH)];
[$^{99m}$Tc(N)(PNP3OH)(Cys)]$^{0/+}$;
[$^{99m}$Tc(N)(PNP43)(Cys)];
[$^{99m}$Tc(N)(PNP3OH)(Abu-Cys)]; and
[$^{99m}$Tc(N)(PNP3OH)(Cys-Gly-Lys-Gly)]$^+$ ("Cys-Gly-Lys-Gly" disclosed as SEQ ID NO: 1).

7. The compound according to claim 1, wherein ZY is linked to, or is a part of a bioactive molecule.

8. The compound according to claim 7 selected from the group consisting of:

[$^{99m}$Tc(N)(PNP3OH)(Cys-cRGDfK)]$^+$; [$^{99m}$Tc(N)(PNP3OH)(Biot-Abu-Cys)]; and
[99mTc(N)(PNP3OH)(Glu-Urea-Lys-2-naphthyl-L-Ala-Amc-Cys)]$^+$.

9. A radiopharmaceutical composition suitable for protein-targeted SPECT imaging comprising the compound of formula (I), according to claim 1 and at least one physiologically acceptable excipient.

10. A process for preparation of a compound of formula (I)

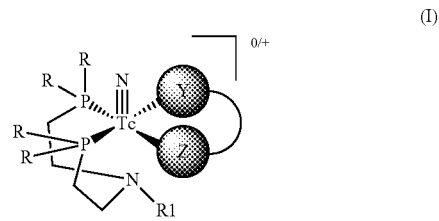

(I)

wherein:

Tc is $^{99m}$Tc;

R is hydrogen (—H) or a group of formula —(CH$_2$)$_n$-A, wherein n is an integer of 1 or 2 and A is selected from the group consisting of hydrogen (—H), hydroxyl (—OH), methyl (—CH$_3$), carboxyl (—COOH), sodium carboxyl (—COONa), amino (—NH$_2$), cyanide (—CN), sulfonyl (—SO$_3$H) and sodium sulfonyl (—SO$_3$Na);

R$_1$ is a group of formula —(CH$_2$)$_m$—R$_2$, wherein m is an integer of 1 to 6 and R$_2$ is selected from the group consisting of alkoxyl (—O-Ak), hydroxyl (—OH), carboxyl (—COOH), and amino (—NH$_2$); and ZY is a bidentate ligand, coordinated with Tc through a combination of electron-donating atoms selected from the group consisting of [O$^-$,S$^-$], [S$^-$,S$^-$], [O$^-$,S], [O,S$^-$], [N$^-$,S], and [N$^-$, S$^-$], wherein ZY is not coordinated with Tc through [N,S$^-$] if R is —CH$_3$ and R$_1$ is —(CH$_2$)$_2$—OCH$_3$, comprising:

reacting, at a temperature of from 15° C. to 60° C., $^{99m}$Tc-pertechnetate, a reducing agent, a nitrido nitrogen donor, and a bidentate ligand ZY having a combination of electron-donating atoms selected from the group consisting of [O$^-$,S$^-$], [S$^-$,S$^-$], [O$^-$,S], [O,S$^-$], [N,S$^-$], [N$^-$,S], and [N$^-$,S$^-$] with a bisphosphinoamine compound of formula (VII)

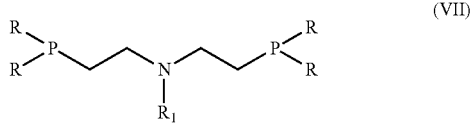

(VII)

wherein R is hydrogen (—H) or a group of formula —(CH$_2$)$_n$-A, wherein n is an integer of 1 or 2 and A is selected from the group consisting of hydrogen (—H), hydroxyl (—OH), methyl (—CH$_3$), carboxyl (—COOH), sodium carboxyl (—COONa), amino (—NH$_2$), cyanide (—CN), sulfonyl (—SO$_3$H) and sodium sulfonyl (—SO$_3$Na) and wherein R$_1$ is a group of formula —(CH$_2$)$_m$—R$_2$, wherein m is an integer of 1 to 6 and R$_2$ is selected from the group consisting of alkoxyl (—O-Ak), hydroxyl (—OH), carboxyl (—COOH), and amino (—NH$_2$), or formula (VIII)

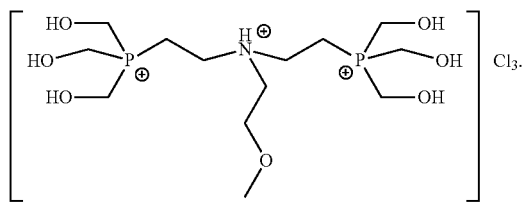

(VIII)

11. The process according to claim 10, wherein the reducing agent is selected from the group consisting of stannous chloride, sodium hydrogen sulfite, sodium borohydride, tertiary phosphines, and tris(m-sulfonatophenyl) phosphine.

12. The process according to claim 10, wherein the nitrido nitrogen donor is selected from the group consisting of dithiocarbazic acid, dithiocarbazic acid derivatives, hydrazine, hydrazine derivatives, and hydrazides derivatives.

13. The process according to claim 10, wherein the nitrido nitrogen donor is succinic dihydrazide.

14. The process according to claim 10, wherein the reacting includes a) mixing the $^{99m}$Tc-pertechnetate, the reducing agent, and the nitrido nitrogen donor; and b) at a pH of from 5.5 to 9.0, adding a buffer solution containing the bidentate ligand ZY and the bisphosphinoamine compound of formula (VII) or formula (VIII), wherein the buffer solution is selected from the group consisting of phosphate buffers, sodium phosphate buffers, phosphate buffered saline, and sodium carbonate buffers.

15. The process according to claim 14, wherein the buffer solution is sodium phosphate buffer 0.2 M pH 7.4 or phosphate buffered saline 0.01 M pH 7.4.

16. The process according to claim 10, wherein the bidentate ligand ZY is linked to, or is a part of a bioactive molecule.

17. The process according to claim 16, wherein the bioactive molecule is selected from the group consisting of polypeptides, proteins, antibodies, and aptamers.

18. The process according to claim 10, wherein the temperature is room temperature.

19. A two- or a three-container kit, wherein the two-container kit comprises container 1 and container 2, and the three-container kit comprises container 3, container 4, and container 5; wherein the container 1 comprises a reducing agent and a nitrido nitrogen donor, the container 2 comprises a bidentate ligand ZY having a combination of electron-donating atoms selected from the group consisting of [O$^-$, S$^-$], [S$^-$ S$^-$], [O$^-$,S], [O,S$^-$], [N,S$^{31}$], [N$^-$,S], and [N$^-$,S$^-$] and a bisphosphinoamine compound of formula (VII):

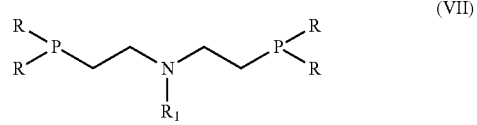

(VII)

wherein R is hydrogen (-H) or a group of formula -(CH$_2$)$_n$-A, wherein n is an integer of 1 or 2 and A is selected from the group consisting of hydrogen (—H), hydroxyl (—OH), methyl (—CH$_3$), carboxyl (—COOH), sodium carboxyl (—COONa), amino (—NH$_2$), cyanide (—CN), sulfonyl (—SO$_3$H) and sodium sulfonyl (—SO$_3$Na) and wherein R$_1$ is a group of formula —(CH$_2$)$_m$—R$_2$, wherein m is an integer of 1 to 6 and R$_2$ is selected from the group consisting of alkoxyl (—O-Ak), hydroxyl (—OH), carboxyl (—COOH), and amino (—NH$_2$); or formula (VIII):

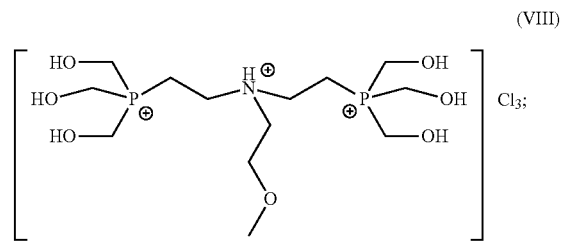

(VIII)

and wherein the container 3 comprises the reducing agent and the nitrido nitrogen donor, the container 4 comprises the bidentate ligand ZY, and the container 5 comprises the bisphosphinoamine compound of formula (VII) or formula (VIII).

20. The kit according to claim 19, wherein the bidentate ligand ZY is linked to or is a part of a bioactive molecule.

* * * * *